(12) United States Patent
Anthony et al.

(10) Patent No.: US 6,358,985 B1
(45) Date of Patent: Mar. 19, 2002

(54) INHIBITORS OF PRENYL-PROTEIN TRANSFERASE

(75) Inventors: Neville J. Anthony, Hatfield; Ian M. Bell, Harleysville; Douglas C. Beshore, Lansdale; Terrence M. Ciccarone, Telford; S. Jane de Solms, Norristown; Christopher J. Dinsmore, Schwenksville; Gerald E. Stokker, Gwynedd Valley, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/342,577

(22) Filed: Jun. 29, 1999

Related U.S. Application Data

(60) Provisional application No. 60/091,513, filed on Jul. 2, 1998.

(51) Int. Cl.[7] .................. A61K 31/4164; C07D 487/08
(52) U.S. Cl. ...................... 514/393; 514/393; 540/455; 540/456; 540/468
(58) Field of Search .......................... 514/393; 540/455, 540/456, 468

(56) References Cited

U.S. PATENT DOCUMENTS 5,756,528 A    5/1998   Anthony et al. ............ 514/399

FOREIGN PATENT DOCUMENTS

| WO | WO 95/10515 | 4/1995 |
|----|-------------|--------|
| WO | WO 96/30363 | 10/1996 |
| WO | WO 96/31111 | 10/1996 |
| WO | WO 96/31477 | 10/1996 |
| WO | WO 96/31478 | 10/1996 |
| WO | WO 97/27752 | 8/1997 |
| WO | WO 97/27852 | 8/1997 |
| WO | WO 97/27853 | 8/1997 |
| WO | WO 97/27854 | 8/1997 |
| WO | WO 97/36583 | 10/1997 |
| WO | WO 97/36584 | 10/1997 |
| WO | WO 98/11091 | 3/1998 |

OTHER PUBLICATIONS

J. Med. Chem. vol. 42 No. 19 1999 3779–3784 Williams et al "N–Arylpiperazinone Inhibitors of Farnesyltransferase: Discovery and Biological Activity".
Exp. Opin. Ther. Patents (1998) 8(5):553–569 Williams "Inhibitors of Protein Farnesylation 1998".
Exp. Opin. Ther. Patents (1999) 9(9):1263–1280 Williams "Inhibitors of protein prenylation 1999".
Nature Medicine, vol. 1, No. 8, 792–796 1995 Kohl et al "Inhibition of farnesyltransferase induces regression of mammary and salivary carcinomas in ras transgenic mice".
Proc. Natl. Acad. Sci. USA, vol. 91, 9141–9145 1994 Kohl et al "Protein farnesyltransferase ingibitors block the growth of ras–dependent tumors in nude mice".
Exp. Opin. Ther. Patents (1996) 6(12):1295–1304 Graham et al "Oncologic, Endocrine & Metabolic. Inhibitors of protein farnesylation".
Exp. Opin. Ther. Patents (1995) 5(12):1269–1285 Graham "Oncologic, Endocrine & Metabolic. Inhibitors of protein farnesylation: a new approach to cancer chemotherapy".
Cancer research 55 5302–5309 (1995) Sepp–Lorenzino et al "A Peptidomimetic Inhibitor of Farnesyl:Protein Transferase Blocks the Anchorage–dependent and –independent Growth of Human Tumor Cell Lines".

*Primary Examiner*—Mukund J. Shah
*Assistant Examiner*—Ben Schroeder
(74) *Attorney, Agent, or Firm*—David A. Muthard; Mark R. Daniel

(57) ABSTRACT

The present invention is directed to peptidomimetic macrocyclic compounds which inhibit prenyl-protein transferase and the prenylation of the oncogene protein Ras. The invention is further directed to chemotherapeutic compositions containing the compounds of this invention and methods for inhibiting prenyl-protein transferase and the prenylation of the oncogene protein Ras.

26 Claims, No Drawings

SEQUENCE LISTING

<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: completely synthetic sequence

<400> SEQUENCE: 1

Cys Val Leu Leu
 1

<210> SEQ ID NO 2
<211> LENGTH: 4
<212> TYPE: PRT
<213> ORGANISM: Artificial Sequence
<220> FEATURE:
<223> OTHER INFORMATION: completely synthetic sequence

<400> SEQUENCE: 2

Cys Val Leu Ser
 1

<210> SEQ ID NO 3
<211> LENGTH: 15
<212> TYPE: PRT
<213> ORGANISM: Artificial Sequence
<220> FEATURE:
<223> OTHER INFORMATION: completely synthetic sequence

<400> SEQUENCE: 3

Gly Lys Lys Lys Lys Lys Ser Lys Thr Lys Cys Val Ile Met
 1               5                  10                  15

<210> SEQ ID NO 4
<211> LENGTH: 52
<212> TYPE: DNA
<213> ORGANISM: Artificial Sequence
<220> FEATURE:
<223> OTHER INFORMATION: completely synthetic sequence

<400> SEQUENCE: 4
gagagggaat tcgggccctt cctgcatgct gctgctgctg ctgctgctgg gc        52

<210> SEQ ID NO 5
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 5
gagagagctc gaggttaacc cgggtgcgcg gcgtcggtgg t              41

<210> SEQ ID NO 6
<211> LENGTH: 42
<212> TYPE: DNA
<213> ORGANISM: Artificial Sequence
<220> FEATURE:
<223> OTHER INFORMATION: completely synthetic sequence

<400> SEQUENCE: 6
gagagagtct agagttaacc cgtggtcccc gcgttgcttc ct             42

```
<210> SEQ ID NO 7
<211> LENGTH: 43
<212> TYPE: DNA
<213> ORGANISM: Artificial Sequence
<220> FEATURE:
<223> OTHER INFORMATION: completely synthetic sequence

<400> SEQUENCE: 7
gaagaggaag cttggtaccg ccactgggct gtaggtggtg gct                   43

<210> SEQ ID NO 8
<211> LENGTH: 27
<212> TYPE: DNA
<213> ORGANISM: Artificial Sequence
<220> FEATURE:
<223> OTHER INFORMATION: completely synthetic sequence

<400> SEQUENCE: 8
ggcagagctc gtttagtgaa ccgtcag                                     27

<210> SEQ ID NO 9
<211> LENGTH: 27
<212> TYPE: DNA
<213> ORGANISM: Artificial Sequence
<220> FEATURE:
<223> OTHER INFORMATION: completely synthetic sequence

<400> SEQUENCE: 9
gagagatctc aaggacggtg actgcag                                     27

<210> SEQ ID NO 10
<211> LENGTH: 86
<212> TYPE: DNA
<213> ORGANISM: Artificial Sequence
<220> FEATURE:
<223> OTHER INFORMATION: completely synthetic sequence

<400> SEQUENCE: 10
tctcctcgag gccaccatgg ggagtagcaa gagcaagcct aaggacccca gccagcgccg  60
gatgacagaa tacaagcttg tggtgg                                      86

<210> SEQ ID NO 11
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 11
cacatctaga tcaggacagc acagacttgc agc                              33

<210> SEQ ID NO 12
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 12
tctcctcgag gccaccatga cagaatacaa gcttgtggtg g                     41

<210> SEQ ID NO 13
<211> LENGTH: 38
<212> TYPE: DNA
```

<213> ORGANISM: Artificial Sequence
<220> FEATURE:
<223> OTHER INFORMATION: completely synthetic sequence

<400> SEQUENCE: 13
cactctagac tggtgtcaga gcagcacaca cttgcagc    38

<210> SEQ ID NO 14
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 14
gagagaattc gccaccatga cggaatataa gctggtgg    38

<210> SEQ ID NO 15
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 15
gagagtcgac gcgtcaggag agcacacact tgc    33

<210> SEQ ID NO 16
<211> LENGTH: 22
<212> TYPE: DNA
<213> ORGANISM: Artificial Sequence
<220> FEATURE:
<223> OTHER INFORMATION: completely synthetic sequence

<400> SEQUENCE: 16
ccgccggcct ggaggagtac ag    22

<210> SEQ ID NO 17
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 17
gagagaattc gccaccatga ctgagtacaa actggtgg    38

<210> SEQ ID NO 18
<211> LENGTH: 32
<212> TYPE: DNA
<213> ORGANISM: Artificial Sequence
<220> FEATURE:
<223> OTHER INFORMATION: completely synthetic sequence

<400> SEQUENCE: 18
gagagtcgac ttgttacatc accacacatg gc    32

<210> SEQ ID NO 19
<211> LENGTH: 21
<212> TYPE: DNA
<213> ORGANISM: Artificial Sequence
<220> FEATURE:
<223> OTHER INFORMATION: completely synthetic sequence

<400> SEQUENCE: 19
gttggagcag ttggtgttgg g                                           21

<210> SEQ ID NO 20
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 20
gagaggtacc gccaccatga ctgaatataa acttgtgg                         38

<210> SEQ ID NO 21
<211> LENGTH: 36
<212> TYPE: DNA
<213> ORGANISM: Artificial Sequence
<220> FEATURE:
<223> OTHER INFORMATION: completely synthetic sequence

<400> SEQUENCE: 21
ctctgtcgac gtatttacat aattacacac tttgtc                           36

<210> SEQ ID NO 22
<211> LENGTH: 24
<212> TYPE: DNA
<213> ORGANISM: Artificial Sequence
<220> FEATURE:
<223> OTHER INFORMATION: completely synthetic sequence

<400> SEQUENCE: 22
gtagttggag ctgttggcgt aggc                                        24

<210> SEQ ID NO 23
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 23
gagaggtacc gccaccatga ctgaatataa acttgtgg                         38

<210> SEQ ID NO 24
<211> LENGTH: 45
<212> TYPE: DNA
<213> ORGANISM: Artificial Sequence
<220> FEATURE:
<223> OTHER INFORMATION: completely synthetic sequence

<400> SEQUENCE: 24
ctctgtcgac agattacatt ataatgcatt ttttaattttt cacac                45

<210> SEQ ID NO 25
<211> LENGTH: 24
<212> TYPE: DNA
<213> ORGANISM: Artificial Sequence
<220> FEATURE:
<223> OTHER INFORMATION: completely synthetic sequence

<400> SEQUENCE: 25
gtagttggag ctgttggcgt aggc                                        24

INHIBITORS OF PRENYL-PROTEIN TRANSFERASE

The application claims the benefit of U.S. provisional application Ser. No. 06/091,531 filed Jul. 2, 1998.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The term prenyl-protein transferase may be used to generally refer to farnesyl-protein transferase and geranylgeranyl-protein transferase. The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit prenyl-protein transferase and thus, the post-translational prenylation of proteins. It is a further object of this invention to develop chemotherapeutic compositions containing the compounds of this invention and methods for producing the compounds of this invention.

SUMMARY OF THE INVENTION

The present invention comprises peptidomimetic macrocyclic compounds which inhibit the prenyl-protein transferase. Further contained in this invention are chemotherapeutic compositions containing these prenyl-protein transferase inhibitors and methods for their production.

The compounds of this invention are illustrated by the formula A:

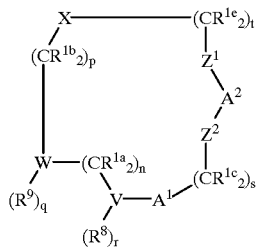

DETAILED DESCRIPTION OF THE INVENTION

The compounds of this invention are useful in the inhibition of prenyl-protein transferase and the prenylation of the oncogene protein Ras. In a first embodiment of this invention, the inhibitors of prenyl-protein transferase are illustrated by the formula A:

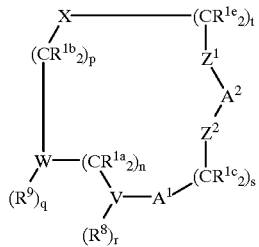

wherein:

$R^{1a}$, $R^{1b}$, $R^{1c}$ and $R^{1e}$ are independently selected from:
a) hydrogen,
b) aryl, heterocycle, cycloalkyl, alkenyl, alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

or two $R^{1a}$s, two $R^{1b}$s, two $R^{1c}$s or two $R^{1e}$s, on the same carbon atom may be combined to form —$(CH_2)_v$—;
$R^4$ is selected from $C_{1-4}$ alkyl, $C_{3-6}$ cycloalkyl, heterocycle, aryl, unsubstituted or substituted with:
a) $C_{1-4}$ alkoxy,
b) aryl or heterocycle,
c) halogen,
d) HO,
e) 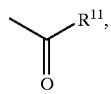
f) —$SO_2R^{11}$
g) $N(R^{10})_2$, or
h) $C_{1-4}$ perfluoroalkyl;

$R^6$ and $R^7$ are independently selected from:
1) hydrogen,
2) $R^{10}C(O)$—, or $R^{10}OC(O)$—, and
3) $C_1$–$C_6$ alkyl, $C_2$–$C_6$ alkenyl, $C_2$–$C_6$ alkynyl, $C_{3-6}$ cycloalkyl, heterocycle, aryl, aroyl, heteroaroyl, arylsulfonyl, heteroarylsulfonyl, $C_6$–$C_{10}$ multicyclic alkyl ring, unsubstituted or substituted with one or more substituents selected from:
a) $R^{10}O$—,
b) aryl or hetrocycle,
c) halogen,
d) $R^{10}C(O)NR^{10}$—,
e) 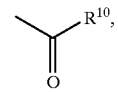
f) —$SO_2R^{11}$
g) $N(R^{10})_2$,
h) $C_{3-6}$ cycloalkyl,
i) $C_6$–$C_{10}$ multicyclic alkyl ring,
j) $C_1$–$C_6$ perfluoroalkyl,
k) $(R^{10})_2N$—$C(NR^{10})$—,
l) $R^{10}OC(O)$—,
m) $R^{11}OC(O)NR^{10}$—,
n) CN, and
o) $NO_2$; or
$R^6$ and $R^7$ may be joined in a ring;
$R^8$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{10}C(O)$—, $R^{10}OC(O)$—, $N_3$, —$N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl, unsubstituted or substituted benzyl, unsubstituted or substituted aryl and unsubstituted or substituted heterocycle;
$R^{11}$ is independently selected from $C_1$–$C_6$ alkyl unsubstituted or substituted aryl and unsubstituted or substituted heterocycle;
$R^{12}$ is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond, —C(O)—, —C(O)$NR^{10}$—, —$NR^{10}$C(O)—, O, —N($R^{10}$)—, —S(O)$_2$N($R^{10}$)—, —N($R^{10}$)S(O)$_2$—, and S(O)$_m$;

$A^2$ is selected from a bond, —C(O)—, —C(O)$NR^{10}$—, —$NR^{10}$C(O)—, O, —N($R^{10}$)—, —S(O)$_2$N($R^{10}$)—, —N($R^{10}$)S(O)$_2$—, S(O)$_m$ and —C($R^{1d}$)$_2$—;

W is heteroaryl;

V is selected from:
a) heteroaryl, and
b) aryl;

X is independently selected from —C(O)—, —C(O)$NR^{10}$—, —$NR^{10}$C(O)—, —$NR^{10}$C(O)—O—, —O—C(O)$NR^{10}$—, —$NR^{10}$C(O)$NR^{10}$—, —C(O)$NR^{10}$C(O)—, O, —N($R^{10}$)—, —S(O)$_2$N($R^{10}$)—, —N($R^{10}$)S(O)$_2$— and S(O)$_m$;

$Z^1$ is selected from unsubstituted or substituted aryl and unsubstituted or substituted heterocycle, wherein the substituted aryl or substituted heterocycle is substituted with one or more of:
1) $C_{1-8}$ alkyl, $C_{2-8}$ alkenyl or $C_{2-8}$ alkynyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —S(O)$_m R^4$,
   g) —C(O)$NR^6R^7$,
   h) —Si($C_{1-4}$ alkyl)$_3$, or
   i) $C_{1-4}$ perfluoroalkyl;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) —S(O)$_m R^4$,
10) —OS(O)$_2 R^4$,
11) —C(O)$NR^6R^7$,
12) —C(O)$OR^6$, or
13) $C_3$–$C_6$ cycloalkyl;

$Z^2$ is selected from a bond, unsubstituted or substituted aryl and unsubstituted or substituted heteroaryl, wherein the substituted aryl or substituted heteroaryl is substituted with one or more of:
1) $C_{1-8}$ alkyl, $C_{2-8}$ alkenyl or $C_{2-8}$ alkynyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —S(O)$_m R^4$,
   g) —C(O)$NR^6R^7$,
   h) —Si($C_{1-4}$ alkyl)$_3$, or
   i) $C_{1-4}$ perfluoroalkyl;
2) substituted or unsubstituted aryl or substituted or unsubstituted heterocycle, 3) halogen,
4) $OR^6$,
5) $NR^6R^7$,
6) CN,
7) $NO_2$,
8) $CF_3$,
9) —S(O)$_m R^4$,
10) —OS(O)$_2 R^4$,
11) —C(O)$NR^6R^7$,
12) —C(O)$OR^6$, or
13) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3;
t is 1, 2, 3 or 4; and
v is 2 to 6;

or a pharmaceutically acceptable salt or stereoisomer thereof.

In a second embodiment of this invention, the inhibitors of prenyl-protein transferase are illustrated by the formula A:

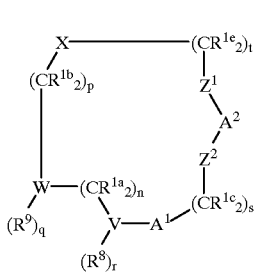

A wherein:

$R^{1a}$, $R^{1b}$, $R^{1c}$, $R^{1d}$ and $R^{1e}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}$O—, $R^{11}$S(O)$_m$—, $R^{10}$C(O)$NR^{10}$—, ($R^{10}$)$_2$N—C(O)—, CN, $NO_2$, ($R^{10}$)$_2$N—C($NR^{10}$)—, $R^{10}$C(O)—, $R^{10}$OC(O)—, $N_3$, —N($R^{10}$)$_2$, or $R^{11}$OC(O)$NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}$O—, $R^{11}$S(O)$_m$—, $R^{10}$C(O)$NR^{10}$—, ($R^{10}$)$_2$N—C(O)—, CN, ($R^{10}$)$_2$N—C($NR^{10}$)—, $R^{10}$C(O)—, $R^{10}$OC(O)—, $N_3$, —N($R^{10}$)$_2$, and $R^{11}$OC(O)—$NR^{10}$—;

$R^4$ is selected from $C_{1-4}$ alkyl, $C_{3-6}$ cycloalkyl, heterocycle, aryl, unsubstituted or substituted with:
a) $C_{1-4}$ alkoxy,
b) aryl or heterocycle, c) halogen,
d) HO, e) 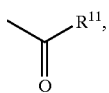

f) —SO$_2$R$^{11}$, or
g) N(R$^{10}$)$_2$;

R$^6$ and R$^7$ are independently selected from H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
   a) C$_{1-4}$ alkoxy,
   b) aryl or heterocycle,
   c) halogen,
   d) HO, e) 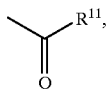

f) —SO$_2$R$^{11}$, or
g) N(R$^{10}$)$_2$; or

R$^6$ and R$^7$ may be joined in a ring;
R$^8$ is independently selected from:
   a) hydrogen,
   b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
   c) C$_1$–C$_6$ alkyl unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{10}$OC(O)NH—;

R$^9$ is selected from:
   a) hydrogen,
   b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
   c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl, unsubstituted or substituted aryl and unsubstituted or substituted heterocycle;
R$^{11}$ is independently selected from C$_1$–C$_6$ alkyl unsubstituted or substituted aryl and unsubstituted or substituted heterocycle;
A$^1$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, and S(O)$_m$;

A$^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, S(O)$_m$ and —C(R$^{1d}$)$_2$—;

W is heteroaryl;
V is selected from:
   a) heteroaryl, and
   b) aryl;
X is selected from —C(O)—, —C(O)NR$^{10}$—, —NR$^{10}$C(O)—, —NR$^{10}$C(O)—O—, —O—C(O)NR$^{10}$—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$— and S(O)$_m$;

Z$^1$ is selected from unsubstituted or substituted aryl and unsubstituted or substituted heteroaryl, wherein the substituted aryl or substituted heteroaryl is substituted with one or more of:
   1) C$_{1-4}$ alkyl, unsubstituted or substituted with:
      a) C$_{1-4}$ alkoxy,
      b) NR$^6$R$^7$,
      c) C$_{3-6}$ cycloalkyl,
      d) aryl or heterocycle,
      e) HO,
      f) —S(O)$_m$R$^4$, or
      g) —C(O)NR$^6$R$^7$,
   2) aryl or heterocycle,
   3) halogen,
   4) OR$^6$,
   5) NR$^6$R$^7$,
   6) CN,
   7) NO$_2$,
   8) CF$_3$,
   9) —S(O)$_m$R$^4$,
   10) —C(O)NR$^6$R$^7$, or
   11) C$_3$–C$_6$ cycloalkyl;

Z$^2$ is selected from a bond, unsubstituted or substituted aryl and unsubstituted or substituted heteroaryl, wherein the substituted aryl or substituted heteroaryl is substituted with one or more of:
   1) C$_{1-4}$ alkyl, unsubstituted or substituted with:
      a) C$_{1-4}$ alkoxy,
      b) NR$^6$R$^7$,
      c) C$_{3-6}$ cycloalkyl,
      d) aryl or heterocycle,
      e) HO,
      f) —S(O)$_m$mR$^4$, or
      g) —C(O)NR$^6$R$^7$,
   2) aryl or heterocycle,
   3) halogen,
   4) OR$^6$,
   5) NR$^6$R$^7$,
   6) CN,
   7) NO$_2$,
   8) CF$_3$,
   9) —S(O)$_m$R$^4$,
   10) —C(O)NR$^6$R$^7$, or
   11) C$_3$–C$_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
t is 1, 2, 3 or 4;

or a pharmaceutically acceptable salt or stereoisomer thereof.

In a third embodiment of this invention, the inhibitors of prenyl-protein transferase are illustrated by the formula A:

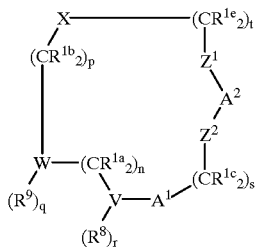

wherein:
$R^{1a}$ and $R^{1d}$ is independently selected from hydrogen and $C_1$–$C_6$ alkyl;

$R^{1b}$, $R^{1c}$ and $R^{1e}$ are independently selected from:
a) hydrogen,
b) aryl, heterocycle, cycloalkyl, $R^{10}O$—, —$N(R^{10})_2$ or $C_2$–$C_6$ alkenyl, and
c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, $R^{10}O$— and —$N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-4}$ alkyl, $C_{3-6}$ cycloalkyl, aryl and heterocycle, unsubstituted or substituted with:
a) $C_{1-4}$ alkoxy,
b) halogen, or
c) aryl or heterocycle;

$R^8$ is independently selected from:
a) hydrogen,
b) unsubstituted or substituted aryl, unsubstituted or substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by: unsubstituted or substituted aryl, unsubstituted or substituted heterocycle, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl unsubstituted or substituted by $C_1$–$C_6$perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, benzyl, unsubstituted or substituted aryl and unsubstituted or substituted heterocycle;

$R^{11}$ is independently selected from $C_1$–$C_6$ alkyl, unsubstituted or substituted aryl and unsubstituted or substituted heterocycle;

$A^1$ is selected from a bond, —C(O)—, —C(O)$NR^{10}$—, —$NR^{10}C(O)$—, O, —$N(R^{10})$—, —$S(O)_2N(R^{10})$—, —$N(R^{10})S(O)_2$—, and $S(O)_m$;

$A^2$ is selected from a bond, —C(O)—, —C(O)$NR^{10}$—, —$NR^{10}C(O)$—, O, —$N(R_{10})$—, —$S(O)_2N(R_{10})$—, —$N(R^{10})S(O)_2$—, $S(O)_m$ and —$C(R^{1d})_2$—;

V is selected from:
a) heteroaryl selected from imidazolyl, pyridinyl, thiazolyl, indolyl, quinolinyl, isoquinolinyl, and thienyl, and
b) aryl;

W is a heteroaryl selected from imidazolyl, pyridinyl, thiazolyl, indolyl, quinolinyl, or isoquinolinyl;

X is selected from —C(O)—, —C(O)$NR^{10}$—, —$NR^{10}C(O)$—, )-, —$NR^{10}C(O)NR^{10}$—, —$C(O)NR^{10}C(O)$—, O, —$N(R^{10})$—, —$S(O)_2N(R^{10})$—, —$N(R^{10})S(O)_2$—, and $S(O)_m$;

$Z^1$ is selected from unsubstituted or substituted aryl or unsubstituted or substituted heteroaryl, wherein the substituted aryl or substituted heteroaryl is independently substituted with one or two of:
1) $C_{1-4}$ alkyl, unsubstituted or substituted with:
 a) $C_{1-4}$ alkoxy,
 b) $NR^6R^7$,
 c) $C_{3-6}$ cycloalkyl,
 d) aryl or heterocycle,
 e) HO,
 f) —$S(O)_mR^4$, or
 g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C_6$ cycloalkyl;

$Z^2$ is selected from a bond, unsubstituted or substituted aryl and unsubstituted or substituted heteroaryl, wherein the substituted aryl or substituted heteroaryl is substituted independently with one or two of:
1) $C_{1-4}$ alkyl, unsubstituted or substituted with:
 a) $C_{1-4}$ alkoxy,
 b) $NR^6R^7$,
 c) $C_{3-6}$ cycloalkyl,
 d) aryl or heterocycle,
 e) HO,
 f) —$S(O)_mR^4$, or
 g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C_6$ cycloalkyl;

m is 0, 1 or 2;
n is 0, 1, 2, 3 or 4;

p is 0, 1, 2, 3 or 4;
q is 1 or 2;
r is 0 to 5;
s is independently 0, 1, 2 or 3; and
t is 1, 2, 3 or 4;
or a pharmaceutically acceptable salt or stereoisomer thereof.

In a fourth embodiment of this invention, the inhibitors of prenyl-protein transferase are illustrated by the formula B:

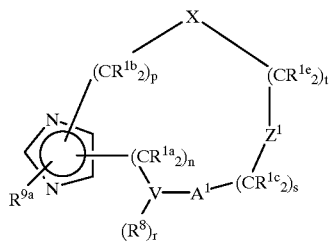

B wherein:
$R^{1a}$, $R^{1b}$ and $R^{1c}$ is independently selected from:
  a) hydrogen,
  b) aryl, heterocycle, cycloalkyl, $R^{10}O$—, —$N(R^{10})_2$ or $C_2$–$C_6$ alkenyl, and
  c) $C_1$–$C_6$ alkyl unsubstituted or substituted by aryl, heterocycle, cycloalkyl, alkenyl, $R^{10}O$—, or —$N(R^{10})_2$;
$R^{1e}$ is independently selected from:
  a) hydrogen,
  b) aryl, heterocycle, cycloalkyl, $R^{10}O$—, —$N(R^{10})_2$ or $C_2$–$C_6$ alkenyl, and
  c) $C_1$–$C_6$ alkyl unsubstituted or substituted by aryl, heterocycle, $R^{10}O$—, or —$N(R^{10})_2$;
$R^4$ is selected from $C_{1-4}$ alkyl and $C_{3-6}$ cycloalkyl, unsubstituted or substituted with:
  a) $C_{1-4}$ alkoxy,
  b) halogen, or
  c) aryl or heterocycle;
$R^6$ and $R^7$ are independently selected from H; $C_{1-6}$ alkyl, $C_{3-6}$ cycloalkyl, $C_6$–$C_{10}$ multicyclic alkyl ring, heterocycle, aryl, aroyl, heteroaroyl, arylsulfonyl, heteroarylsulfonyl, unsubstituted or substituted with one or two:
  a) $C_{1-4}$ alkoxy,
  b) aryl or heterocycle,
  c) halogen,
  d) HO,
  e) 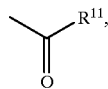
  f) —$SO_2R^{11}$,
  g) $N(R^{10})_2$,
  h) $C_{3-6}$ cycloalkyl,
  i) $C_6$–$C_{10}$ multicyclic alkyl ring; or
$R^8$ is independently selected from:
  a) hydrogen,
  b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;
$R^{9a}$ is hydrogen or methyl;
$R^{10}$ is independently selected from hydrogen, $C_1$–$C_6$ alkyl, benzyl and unsubstituted or substituted aryl;
$R^{11}$ is independently selected from $C_1$–$C_6$ alkyl and unsubstituted or substituted aryl;
$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;
$A^1$ is selected from a bond, —C(O)— and O;
V is selected from:
  a) heteroaryl selected from imidazolyl, pyridinyl, thiazolyl, indolyl, quinolinyl, isoquinolinyl, and thienyl, and
  b) aryl;
X is independently selected from —C(O)—, —C(O)$NR^{10}$—, —$NR^{10}C(O)$—, —$NR^{10}C(O)NR^{10}$—, —C(O)$NR^{10}C(O)$—, O, —$N(R^{10})$—, —$S(O)_2N(R^{10})$—, —$N(R^{10})S(O)_2$—, and $S(O)_m$;
$Z^1$ is selected from unsubstituted or substituted aryl or unsubstituted or substituted heterocycle, wherein the substituted aryl or substituted heterocycle is independently substituted with one or two of:
  1) $C_{1-8}$ alkyl, $C_{2-8}$ alkenyl or $C_{2-8}$ alkynyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —$S(O)_mR^4$,
    g) —$C(O)NR^6R^7$,
    h) —$Si(C_{1-4}$ alkyl$)_3$, or
    i) $C_{1-4}$ perfluoroalkyl;
  2) substituted or unsubstituted aryl or substituted or unsubstituted heterocycle,
  3) halogen,
  4) $OR^6$,
  5) $NR^6R^7$,
  6) CN,
  7) $NO_2$,
  8) $CF_3$,
  9) —$S(O)_mR^4$,
  10) —$OS(O)_2R^4$,
  11) —$C(O)NR^6R^7$,
  12) —$C(O)OR^6$, or
  13) $C_3$–$C_6$ cycloalkyl;
m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;
or a pharmaceutically acceptable salt or stereoisomer thereof.

In a fifth embodiment of this invention, the inhibitors of prenyl-protein transferase are illustrated by the formula B:

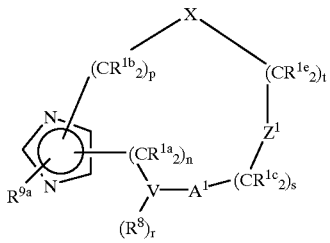

wherein:

$R^{1a}$ and $R^{1e}$ are independently selected from hydrogen or $C_1$–$C_6$ alkyl;

$R^{1b}$ and $R^{1c}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from:
a) hydrogen,
b) $C_1$–$C_6$ alkyl, $C_2$–$C_6$ alkenyl, $C_2$–$C_6$ alkynyl, $R^{10}C(O)$— or $R^{10}OC(O)$— and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by: unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R_{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —C(O)— and O;

V is selected from:
a) heteroaryl selected from imidazolyl, pyridinyl, thiazolyl, indolyl, quinolinyl, isoquinolinyl, and thienyl, and
b) aryl;

X is selected from —C(O)—, —C(O)$NR^{10}$—, —$NR^{10}C(O)$—, )-, —$NR^{10}C(O)NR^{10}$—, —C(O)$NR^{10}C(O)$—, O, —$N(R^{10})$—, —$S(O)_2N(R^{10})$—, —$N(R^{10})S(O)_2$—, and $S(O)_m$;

$Z^1$ is selected from unsubstituted or substituted aryl or unsubstituted or substituted heteroaryl, wherein the substituted aryl or substituted heteroaryl is independently substituted with one or two of:

1) $C_{1-4}$ alkyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) —$S(O)_mR^4$, or
g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

A preferred embodiment of the compounds of this invention is illustrated by the formula C-1:

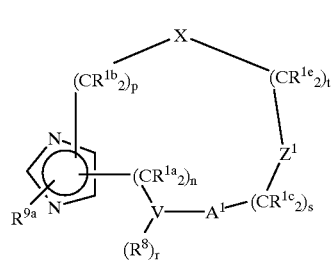

wherein:

$R^{1a}$, $R^{1b}$ and $R^{1c}$ are independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^{1e}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, $R^{10}O$—, or —$N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, heterocycle, aryl, aroyl, heteroaroyl, arylsulfonyl, heteroarylsulfonyl, unsubstituted or substituted with one or two:

a) $C_{1-4}$ alkoxy,
b) aryl or heterocycle,
c) halogen,
d) HO, e) 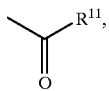

f) $-SO_2R^{11}$,
g) $N(R^{10})_2$,
h) $C_{3-6}$ cycloalkyl,
i) $C_6-C_{10}$ multicyclic alkyl ring; or $R^8$ is independently selected from:
a) hydrogen,
b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{12}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;
$R^{10}$ is independently selected from hydrogen, $C_1-C_6$ alkyl, unsubstituted or substituted benzyl and unsubstituted or substituted aryl;
$R^{11}$ is independently selected from $C_1-C_6$ alkyl and unsubstituted or substituted aryl;
$R^{12}$ is independently selected from hydrogen, $C_1-C_6$ alkyl, unsubstituted or substituted benzyl, unsubstituted or substituted aryl, unsubstituted or substituted heterocycle, and $C_1-C_6$ alkyl substituted with unsubstituted or substituted aryl or unsubstituted or substituted heterocycle;
$A^1$ is selected from a bond, $-C(O)-$ and O;
V is phenyl or pyridyl;
X is independently selected from $-C(O)-$, $-C(O)NR^{10}-$, $-NR^{10}C(O)-$, $-NR^{10}C(O)NR^{10}-$, $-C(O)NR^{10}C(O)-$, O, $-N(R^{10})-$, $-S(O)_2N(R^{10})-$, $-N(R^{10})S(O)_2-$, and $S(O)_m$;
$Z^1$ is selected from unsubstituted or substituted aryl or unsubstituted or substituted heterocycle, wherein the substituted aryl or substituted heterocycle is substituted with one or two of:
1) $C_{1-8}$ alkyl, $C_{2-8}$ alkenyl or $C_{2-8}$ alkynyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) $-S(O)_mR^4$,
   g) $-C(O)NR^6R^7$,
   h) $-Si(C_{1-4}$ alkyl$)_3$, or
   i) $C_{1-4}$ perfluoroalkyl;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) $-S(O)_mR^4$,
10) $-OS(O)_2R^4$,
11) $-C(O)NR^6R^7$,
12) $-C(O)OR^6$, or
13) $C_3-C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;
or a pharmaceutically acceptable salt or stereoisomer thereof.

In another embodiment of this invention, the inhibitors of prenyl-protein transferase are illustrated by the formula C:

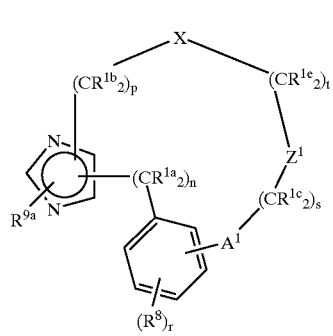

wherein:
$R^{1a}$ and $R^{1e}$ are independently selected from hydrogen and $C_1-C_6$ alkyl;
$R^{1b}$ and $R^{1c}$ is independently selected from:
a) hydrogen,
b) aryl, heterocycle, cycloalkyl, $R^{10}O-$, $-N(R^{10})_2$ or $C_2-C_6$ alkenyl, and
c) $C_1-C_6$ alkyl unsubstituted or substituted by aryl, heterocycle, cycloalkyl, alkenyl, $R^{10}O-$, or $-N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from:
a) hydrogen,
b) $C_1-C_6$ alkyl, $C_2-C_6$ alkenyl, $C_2-C_6$ alkynyl, $R^{10}C(O)-$ or $R^{10}OC(O)-$ and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;

$R^8$ is independently selected from:
a) hydrogen,
b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —C(O)— and O;

X is independently selected from —C(O)—, —C(O)NR$^{10}$—, —NR$^{10}$C(O)—, —NR$^{10}$C(O)NR$^{10}$, —C(O)NR$^{10}$C(O)—, O, —N(R$^{10}$)—, —S(O)$_2$N(R$^{10}$)—, —N(R$^{10}$)S(O)$_2$—, and S(O)m;

$Z^1$ is selected from unsubstituted or substituted aryl or unsubstituted or substituted heteroaryl, wherein the substituted aryl or substituted heteroaryl is substituted with one or two of:

1) $C_{1-4}$ alkyl, unsubstituted or substituted with:
  a) $C_{1-4}$ alkoxy,
  b) NR$^6$R$^7$,
  c) $C_{3-6}$ cycloalkyl,
  d) aryl or heterocycle,
  e) HO,
  f) —S(O)$_m$R$^4$, or
  g) —C(O)NR$^6$R$^7$,
2) aryl or heterocycle,
3) halogen,
4) OR$^6$,
5) NR$^6$R$^7$,
6) CN,
7) N$_2$,
8) CF$_3$,
9) —S(O)$_m$R$^4$,
10) —C(O)NR$^6$R$^7$, or
11) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

In another embodiment of this invention, the inhibitors of prenyl-protein transferase are illustrated by the formula D:

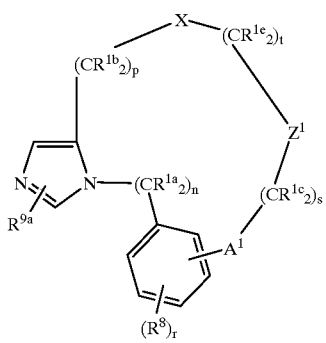

wherein:

$R^{1a}$, $R^{1b}$ and $R^{1c}$ are independently selected from:
  a) hydrogen,
  b) aryl, heterocycle, cycloalkyl, R$^{10}$O—, —N(R$^{10}$)$_2$ or $C_2$–$C_6$ alkenyl, and
  c) $C_1$–$C_6$ alkyl unsubstituted or substituted by aryl, heterocycle, cycloalkyl, alkenyl, R$^{10}$O—, or —N(R$^{10}$)$_2$;

$R^{1e}$ is independently selected from:
  a) hydrogen,
  b) aryl, heterocycle, cycloalkyl, R$^{10}$O—, —N(R$^{10}$)$_2$ or $C_2$–$C_6$ alkenyl, and
  c) $C_1$–$C_6$ alkyl unsubstituted or substituted by aryl, heterocycle, R$^{10}$O—, or —N(R$^{10}$)$_2$;

$R^4$ is selected from $C_{1-4}$ alkyl and $C_{3-6}$ cycloalkyl, unsubstituted or substituted with:
  a) $C_{1-4}$ alkoxy,
  b) halogen, or
  c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, aryl, aroyl, arylsulfonyl, unsubstituted or substituted with one or two:
  a) $C_{1-4}$ alkoxy,
  b) aryl,
  c) halogen,
  d) HO, e) 

f) —SO$_2$R$^{11}$,
  g) N(R$^{10}$)$_2$,
  h) $C_{3-6}$ cycloalkyl,
  i) $C_6$—$C_{10}$ multicyclic alkyl ring; or $R^8$ is independently selected from:
  a) hydrogen,
  b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) $C_1$–$C_6$ alkyl substituted by unsubstituted or substituted aryl, $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

$R^{9a}$ is hydrogen or methyl;

$R^{10}$ and $R^{12}$ are independently selected from hydrogen, $C_1$–$C_6$ alkyl, unsubstituted or substituted benzyl and unsubstituted or substituted aryl;

$R^{11}$ is independently selected from $C_1$–$C_6$ alkyl and unsubstituted or substituted aryl;

$A^1$ is selected from a bond, —C(O)— and O;

X is independently selected from —C(O)—, —C(O)NR$^{10}$—, —NR$^{10}$C(O)—, —NR$^{10}$C(O)NR$^{10}$, —C(O)NR$^{10}$C(O)—, O, —N(R$^{10}$)—, —S(O)$_2$N(R$^{10}$)—, —N(R$^{10}$)S(O)$_2$—, and S(O)$_m$;

$Z^1$ is selected from unsubstituted or substituted aryl or unsubstituted or substituted heterocycle, wherein the substituted aryl or substituted heterocycle is substituted with one or two of:

1) $C_{1-8}$ alkyl, $C_{2-8}$ alkenyl or $C_{2-8}$ alkynyl, unsubstituted or substituted with:
  a) $C_{1-4}$ alkoxy,
  b) NR$^6$R$^7$,
  c) $C_{3-6}$ cycloalkyl,
  d) aryl or heterocycle,
  e) HO,
  f) —S(O)$_m$R$^4$,
  g) —C(O)NR$^6$R$^7$, h) —Si($C_{1-4}$ alkyl)$_3$, or
i) $C_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;
or a pharmaceutically acceptable salt or stereoisomer thereof.

In still another embodiment of this invention, the inhibitors of prenyl-protein transferase are illustrated by the formula D:

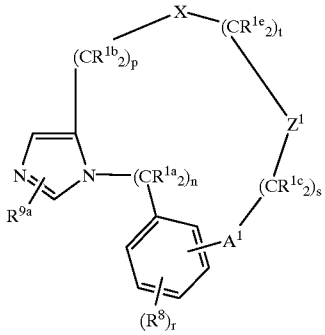

wherein:
R$^{1a}$ and R$^{1e}$ are independently selected from hydrogen and $C_1$–$C_6$ alkyl;
R$^{1b}$ and R$^{1c}$ is independently selected from:
a) hydrogen,
b) aryl, heterocycle, cycloalkyl, R$^{10}$O—, —N(R$^{10}$)$_2$ or $C_2$–$C_6$ alkenyl, and
c) $C_1$–$C_6$ alkyl unsubstituted or substituted by aryl, heterocycle, cycloalkyl, alkenyl, R$^{10}$O—, or —N(R$^{10}$)$_2$;
R$^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;
R$^6$ and R$^7$ are independently selected from:
a) hydrogen,
b) $C_1$–$C_6$ alkyl, $C_2$–$C_6$ alkenyl, $C_2$–$C_6$ alkynyl, R$^{10}$C(O)— or R$^{10}$OC(O)— and
c) $C_1$–$C_6$ alkyl substituted by $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;
R$^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl substituted by unsubstituted or substituted aryl, $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;
R$^{9a}$ is hydrogen or methyl;
R$^{10}$ is independently selected from hydrogen, $C_1$–$C_6$ alkyl, benzyl and unsubstituted or substituted aryl;
R$^{11}$ is independently selected from $C_1$–$C_6$ alkyl and unsubstituted or substituted aryl;
A$^1$ is selected from a bond, —C(O)— and O;
X is selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;
Z$^1$ is selected from unsubstituted or substituted aryl or unsubstituted or substituted heteroaryl, wherein the substituted aryl or substituted heteroaryl is substituted with one or two of:
1) $C_{1-4}$ alkyl, unsubstituted or substituted with:
a) $C_{1-4}$ alkoxy,
b) NR$^6$R$^7$,
c) $C_{3-6}$ cycloalkyl,
d) aryl or heterocycle,
e) HO,
f) —S(O)$_m$R$^4$, or
g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

In a further embodiment of this invention, the inhibitors of prenyl-protein transferase are illustrated by the formula E:

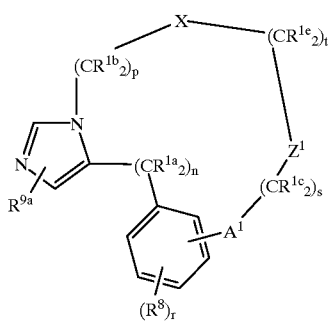

wherein:
$R^{1a}$, $R^{1b}$ and $R^{1c}$ are independently selected from:
 a) hydrogen,
 b) aryl, heterocycle, cycloalkyl, $R^{10}O-$, $-N(R^{10})_2$ or $C_2-C_6$ alkenyl, and
 c) $C_1-C_6$ alkyl unsubstituted or substituted by aryl, heterocycle, cycloalkyl, alkenyl, $R^{10}O-$, or $-N(R^{10})_2$;

$R^{1e}$ is independently selected from:
 a) hydrogen,
 b) aryl, heterocycle, cycloalkyl, $R^{10}O-$, $-N(R^{10})_2$ or $C_2-C_6$ alkenyl, and
 c) $C_1-C_6$ alkyl unsubstituted or substituted by aryl, heterocycle, $R^{10}O-$, or $-N(R^{10})_2$;

$R^4$ is selected from $C_{1-4}$ alkyl and $C_{3-6}$ cycloalkyl, unsubstituted or substituted with:
 a) $C_{1-4}$ alkoxy,
 b) halogen, or
 c) aryl or heterocycle;

$R^6$ and $R^7$ are independently selected from H; $C_{1-6}$ alkyl, $C_{3-6}$ cycloalkyl, $C_6-C_{10}$ multicyclic alkyl ring, aryl, aroyl, arylsulfonyl, unsubstituted or substituted with one or two:
 a) $C_{1-4}$ alkoxy,
 b) aryl,
 c) halogen,
 d) HO,
 e) 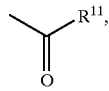
 f) $-SO_2R^{11}$,
 g) $N(R^{10})_2$,
 h) $C_{3-6}$ cycloalkyl,
 i) $C_6-C_{10}$ multicyclic alkyl ring; or $R^8$ is independently selected from:
 a) hydrogen,
 b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{12}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
 c) $C_1-C_6$ alkyl substituted by unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;

$R^{10}$ and $R^{12}$ are independently selected from hydrogen, $C_1-C_6$ alkyl, unsubstituted or substituted benzyl and unsubstituted or substituted aryl;

$R^{11}$ is independently selected from $C_1-C_6$ alkyl and unsubstituted or substituted aryl;

$A^1$ is selected from a bond, $-C(O)-$ and O;

X is independently selected from $-C(O)-$, $-C(O)NR^{10}-$, $-NR^{10}C(O)-$, $-NR^{10}C(O)NR^{10}-$, $-C(O)NR^{10}C(O)-$, O, $-N(R^{10})-$, $-S(O)_2N(R^{10})-$, $-N(R^{10})S(O)_2-$, and $S(O)_m$;

$Z^1$ is selected from unsubstituted or substituted aryl or unsubstituted or substituted heterocycle, wherein the substituted aryl or substituted heterocycle is substituted with one or two of:
 1) $C_{1-8}$ alkyl, $C_{2-8}$ alkenyl or $C_{2-8}$ alkynyl, unsubstituted or substituted with:
  a) $C_{1-4}$ alkoxy,
  b) $NR^6R^7$,
  c) $C_{3-6}$ cycloalkyl,
  d) aryl or heterocycle,
  e) HO,
  f) $-S(O)_mR^4$,
  g) $-C(O)NR^6R^7$,
  h) $-Si(C_{1-4}$ alkyl$)_3$, or
  i) $C_{1-4}$ perfluoroalkyl;
 2) substituted or unsubstituted aryl or substituted or unsubstituted heterocycle,
 3) halogen,
 4) $OR^6$,
 5) $NR^6R^7$,
 6) CN,
 7) $NO_2$,
 8) $CF_3$,
 9) $-S(O)_mR^4$,
 10) $-OS(O)_2R^4$,
 11) $-C(O)NR^6R^7$,
 12) $-C(O)OR^6$, or
 13) $C_3-C_6$ cycloalkyl;

m is 0, 1 or 2;
n is 0, 1, 2, 3 or 4;
p is 2, 3 or 4;
r is 0 to 5;
s is independently 0, 1, 2 or 3; and
t is 1, 2, 3 or 4;

or a pharmaceutically acceptable salt or stereoisomer thereof.

In a further preferred embodiment of this invention, the inhibitors of prenyl-protein transferase are illustrated by the formula E:

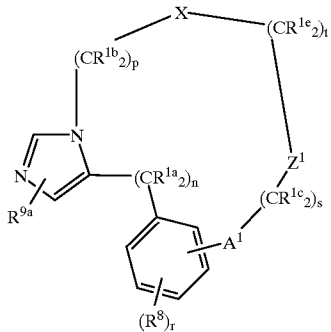

wherein:

R$^{1a}$ and R$^{1e}$ are independently selected from hydrogen and C$_1$–C$_6$ alkyl;

R$^{1b}$ and R$^{1c}$ is independently selected from:
a) hydrogen,
b) aryl, heterocycle, cycloalkyl, R$^{10}$O—, —N(R$^{10}$)$_2$ or C$_2$–C$_6$ alkenyl, and
c) C$_1$–C$_6$ alkyl unsubstituted or substituted by aryl, heterocycle, cycloalkyl, alkenyl, R$^{10}$O—, or —N(R$^{10}$)$_2$;

R$^4$ is selected from C$_{1-4}$ alkyl and C$_{3-6}$ cycloalkyl, unsubstituted or substituted with:
a) C$_{1-4}$ alkoxy,
b) halogen, or
c) aryl or heterocycle;

R$^6$ and R$^7$ are independently selected from:
a) hydrogen,
b) C$_1$–C$_6$ alkyl, C$_2$–C$_6$ alkenyl, C$_2$–C$_6$ alkynyl, R$^{10}$C(O)— or R$^{10}$OC(O)— and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^8$ is independently selected from:
a) hydrogen,
b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;

R$^{10}$ is independently selected from hydrogen, C$_1$–C$_6$ alkyl, benzyl and unsubstituted or substituted aryl;

R$^{11}$ is independently selected from C$_1$–C$_6$ alkyl and unsubstituted or substituted aryl;

A$^1$ is selected from a bond, —C(O)— and O;

X is selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

Z$^1$ is selected from unsubstituted or substituted aryl or unsubstituted or substituted heteroaryl, wherein the substituted aryl or substituted heteroaryl is substituted with one or two of:

1) C$_{1-4}$ alkyl, unsubstituted or substituted with:
a) C$_{1-4}$ alkoxy,
b) NR$^6$R$^7$,
c) C$_{3-6}$ cycloalkyl,
d) aryl or heterocycle,
e) HO,
f) —S(O)$_m$R$^4$, or
g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) C$_3$–C$_6$ cycloalkyl;

m is 0, 1 or 2;
n is 0, 1, 2, 3 or 4;
p is 2, 3 or 4;
r is 0 to 5;
s is independently 0, 1, 2 or 3; and
t is 1, 2, 3 or 4;

or a pharmaceutically acceptable salt or stereoisomer thereof.

Preferably the compounds of the invention are selected from:

18,19-dihydro-19-oxo-5H,17H-6,10:12,16-dimetheno-1H-imidazo[4,3-c][1,11,4]dioxaazacyclononadecine-9-carbonitrile (1), 17,18-dihydro-18-oxo-5H-6,10:12,16-dimetheno-12H,20H-imidazo[4,3-c][1,11,4]dioxaazacyclooctadecine-9-carbonitrile (2), (±)-17,18,19,20-tetrahydro-19-phenyl-5H-6,10:12,16-dimetheno-21H-imidazo[3,4-h][1,8,11]oxadiazacyclononadecine-9-carbonitrile (3), 21,22-dihydro-5H-6,10:12,16-dimetheno-23H-benzo[g]imidazo[4,3-l][1,8,11]oxadiazacyclononadecine-9-carbonitrile (4), 22,23-dihydro-23-oxo-5H,21H-6,10:12,16-dimetheno-24H-benzo[g]imidazo[4,3-m][1,8,12]oxadiazaeicosine-9-carbonitrile (5), 22,23-dihydro-5H,21H-6,10:12,16-dimetheno-24H-benzo[g]imidazo[4,3-m][1,8,11]oxadiazaeicosine-9-carbonitrile (6), 22,23-dihydro-5H,21H-6,10:12,16-dimetheno-23-methyl-24H-benzo[g]imidazo[4,3-m][1,8,11]oxadiazaeicosine-9-carbonitrile (7), (±)-5-hydroxy-5-methyl-24-oxo-21,22,23,24-tetrahydro-5H-6,10:12,16-dimetheno-25H-benzo[o]imidazo[4,3-h][1,9,12]oxadiaza-cycloheneicosine-9-carbonitrile (8), 17-Oxo-17,18,23,24-tetrahydro-5H-6,10:12,16-dimetheno-25H,26H-benzo[n]imidazo[3,4-h][1,8,12,16]oxatriazacyclodocosine-9-carbonitrile (9)

3-Methyl-17-oxo-17,18,23,24-tetrahydro-5H-6,10:12,16-dimetheno-25H,26H-benzo[n]imidazo[3,4-h][1,8,12,16]-oxatriazacyclodocosine-9-carbonitrile (10)

24-tert-Butoxycarbonyl-3-methyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (11)

24-tert-Butoxycarbonyl-18-ethyl-3-methyl-17-oxo-17,18,23,24-tetrahydro-5H-6,10:12,16-dimetheno-25H,26H- benzo[n]imidazo[3,4-h][1,8,12,16]
oxatriazacyclodocosine-9-carbonitrile (12)
18-Ethyl-3-methyl-17-oxo-17,18,23,24-tetrahydro-5H-6,
10:12,16-dimetheno-25H,26H-benzo[n]imidazo[3,4-h]
[1,8,12,16]oxatriazacyclodocosine-9-carbonitrile (13)
24-Acetyl-3-methyl-17-oxo-17,18,23,24-tetrahydro-5H-6,
10:12,16-dimetheno-25H,26H-benzo[n]imidazo[3,4-h]
[1,8,12,16]oxatriazacyclodocosine-9-carbonitrile (14)
3-methyl-24-methylsulfonylethyl-17-oxo-17,18,23,24-
tetrahydro-5H-6,10:12,16-dimetheno-25H,26H-benzo[n]
imidazo[3,4-h][1,8,12,16]oxatriazacyclodocosine-9-
carbonitrile (15)
3,24-Dimethyl-17-oxo-17,18,23,24-tetrahydro-5H-6,10:12,
16-dimetheno-25H,26H-benzo[n]imidazo[3,4-h][1,8,12,
16]oxatriazacyclodocosine-9-carbonitrile (16)
17,18-Dihydro-15-iodo-3-methyl-17-oxo-5H-6,10:12,16-
dimetheno-19H,20H-imidazo[3,4-h][1,8,12]
oxadiazacyclooctadecine-9-carbonitrile (17)
17,18-Dihydro-3-methyl-17-oxo-15-phenyl-5H-6,10:12,16-
dimetheno-19H,20H-imidazo[3,4-h][1,8,12]oxadiaza-
cyclooctadecine-9-carbonitrile (18)
trans-15-[2-(3-Chlorophenyl)ethenyl]-17,18-dihydro-3-
methyl-17-oxo-5H-6,10:12,16-dimetheno-19H,20H-
imidazo[3,4-h][1,8,12]oxadiazacyclooctadecine-9-
carbonitrile (19)
18-Benzyl-17,18-dihydro-15-iodo-3-methyl-17-oxo-5H-6,
10:12,16-dimetheno-19H,20H-imidazo[3,4-h][1,8,12]
oxadiaza-cyclooctadecine-9-carbonitrile (20)

or a pharmaceutically acceptable salt or stereoisomer
thereof.
Specific examples of the compounds of the invention are:

22,23-dihydro-23-oxo-5H,21H-6,10:12,16-dimetheno-24H-
benzo[g]imidazo[4,3-m][1,8,12]oxadiazaeicosine-9-
carbonitrile (5),

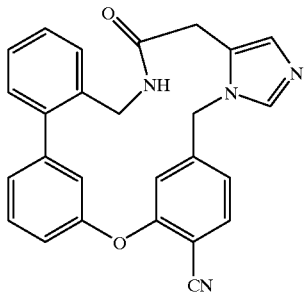

22,23-dihydro-5H,21H-6,10:12,16-dimetheno-24H-benzo
[g]imidazo[4,3-m][1,8,11]oxadiazaeicosine-9-
carbonitrile (6),

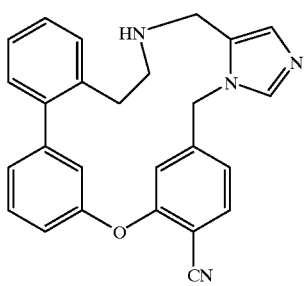

17-Oxo-17,18,23,24-tetrahydro-5H-6,10:12,16-dimetheno-
25H,26H-benzo[n]imidazo[3,4-h][1,8,12,16]oxatriaza-
cyclodocosine-9-carbonitrile (9)

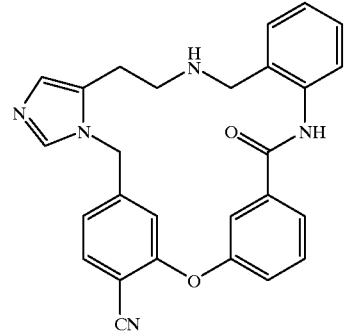

18-Ethyl-3-methyl-17-oxo-17,18,23,24-tetrahydro-5H-6,
10:12,16-dimetheno-25H,26H-benzo[n]imidazo[3,4-h]
[1,8,12,16]oxatriazacyclodocosine-9-carbonitrile (13)

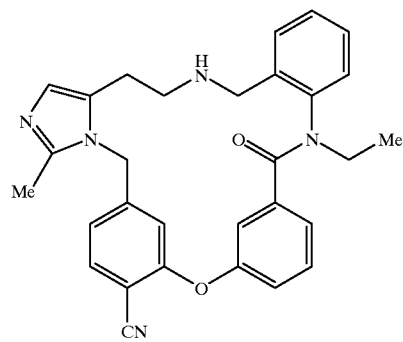

17,18-Dihydro-15-iodo-3-methyl-17-oxo-5H-6,10:12,16-
dimetheno-19H,20H-imidazo[3,4-h][1,8,12]
oxadiazacyclooctadecine-9-carbonitrile (17)

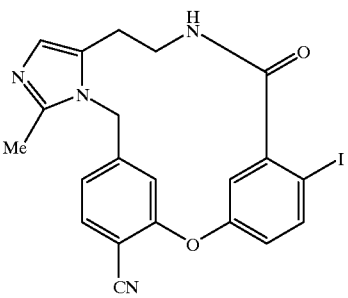

or a pharmaceutically acceptable salt or stereoisomer
thereof.
The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Sterochemistry of Carbon Compounds* (John Wiley and Sons, New York 1994), in particular pages 1119–1190). When any variable (e.g. aryl, heterocycle, $R^{1a}$, $R^6$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

Preferably, alkenyl is $C_2$–$C_6$ alkenyl.

Preferably, alkynyl is $C_2$–$C_6$ alkynyl.

As used herein, "cycloalkyl" is intended to include cyclic saturated aliphatic hydrocarbon groups having the specified number of carbon atoms. Preferably, cycloalkyl is $C_3$–$C_{10}$ cycloalkyl. Examples of such cycloalkyl elements include, but are not limited to, cyclopropyl, cyclobutyl, cyclopentyl, cyclohexyl and cycloheptyl.

As used herein, the term "$C_6$–$C_{10}$ multicyclic alkyl ring" in is intended to include polycyclic saturated and unsaturated aliphatic hydrocarbon groups having the specified number of carbon atoms. Examples of such cycloalkyl groups includes, but are not limited to:

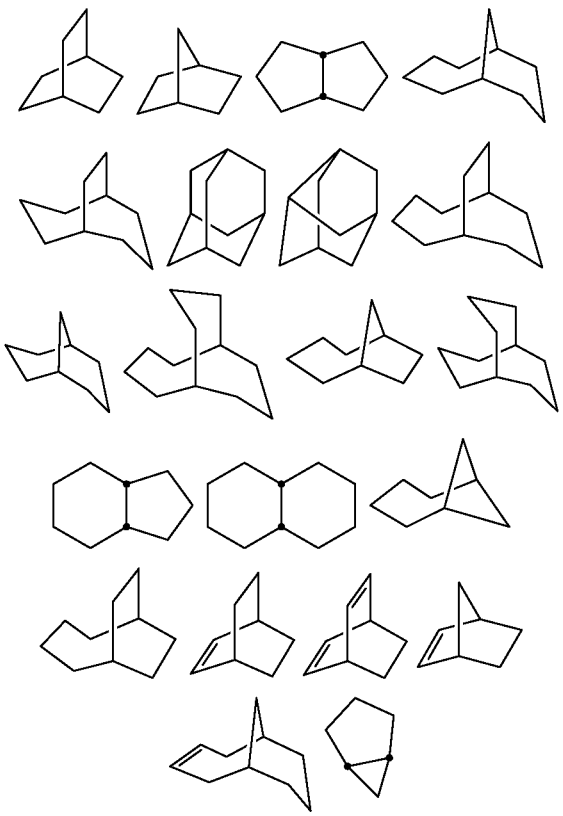

Preferably, $C_6$–$C_{10}$ multicyclic alkyl ring is adamantyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic, as used herein, includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroarylsulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1$–$C_6$ alkyl$)_2$, $NO_2$, CN, ($C_1$–$C_6$ alkyl)O—, (aryl)O—, —OH, ($C_1$–$C_6$ alkyl)S(O)$_m$—, ($C_1$–$C_6$ alkyl)C(O)NH—, $H_2$N—C(NH)—, ($C_1$–$C_6$ alkyl)C(O)—, ($C_1$–$C_6$ alkyl)OC(O)—, $N_3$, ($C_1$–$C_6$ alkyl)OC(O)NH—, phenyl, pyridyl, imidazolyl, oxazolyl, isoxazolyl, thiazolyl, thienyl, furyl, isothiazolyl and $C_1$–$C_{20}$ alkyl.

Preferably, as used herein in the definition of $R^6$ and $R^7$, the substituted $C_{1-6}$ alkyl, substituted $C_{2-6}$ alkenyl, substituted $C_{2-6}$ alkynyl, substituted $C_{3-6}$ cycloalkyl, substituted aroyl, substituted aryl, substituted heteroaroyl, substituted arylsulfonyl, substituted heteroarylsulfonyl, substituted heterocycle and substituted $C_{6-10}$ multicyclic alkyl ring, include moieties containing from 1 to 3 substitutents in addition to the point of attachment to the rest of the compound.

The moiety formed when, in the definition of $R^{1a}$, $R^{1b}$, $R^{1c}$, $R^{1d}$ and $R^{1e}$, two $R^{1a}$s, two $R^{1b}$s, two $R^{1c}$s, two $R^{1d}$s, or two $R^{1e}$s, on the same carbon atom are combined to form —$(CH_2)_r$— is illustrated by the following:

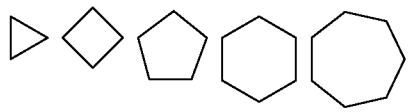

Lines drawn into the ring systems from substituents (such as from $R^8$, $R^9$ etc.) indicate that the indicated bond may be attached to any of the substitutable ring carbon atoms.

Preferably, $R^{1a}$ and $R^{1b}$ are independently selected from: hydrogen, —$N(R^{10})_2$, $R^{10}C(O)NR^{10}$— or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^{1c}$ is independently selected from: hydrogen, or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^4$ is unsubstituted or substituted $C_1$–$C_6$ alkyl, unsubstituted or substituted aryl and unsubstituted or substituted cycloalkyl.

Preferably, $R^6$ and $R^7$ is selected from: hydrogen, unsubstituted or substituted $C_1$–$C_6$ alkyl, unsubstituted or substituted aryl and unsubstituted or substituted cycloalkyl.

Preferably, $R^9$ is hydrogen or methyl.

Preferably, $R^{10}$ is selected from H, $C_1$–$C_6$ alkyl and benzyl.

Preferably, $A^1$ and $A^2$ are independently selected from a bond, —$C(O)NR^{10}$—, —$NR^{10}C(O)$—, O, —$N(R^{10})$—, —$S(O)_2N(R^{10})$— and —$N(R^{10})S(O)_2$—.

Preferably, V is selected from heteroaryl and aryl. More preferably, V is phenyl or pyridyl.

Preferably, X is selected from —$C(O)NR^{10}$—, —$NR^{10}C(O)$—, O, —$N(R^{10})$—, —$S(O)_2N(R^{10})$— and —$N(R^{10})S(O)_2$—.

Preferably, $Z^1$ and $Z^2$ are independently selected from unsubstituted or substituted aryl and unsubstituted or substituted heteroaryl. More preferably, $Z^1$ and $Z^2$ are independently selected from unsubstituted or substituted phenyl, unsubstituted or substituted naphthyl, unsubstituted or substituted pyridyl, unsubstituted or substituted furanyl and unsubstituted or substituted thienyl. Still more preferably, $Z^1$ is selected from unsubstituted or substituted phenyl and unsubstituted or substituted naphthyl. Still more preferably, $Z^2$ is selected from a bond and unsubstituted or substituted phenyl.

Preferably, W is selected from imidazolinyl, imidazolyl, oxazolyl, pyrazolyl, thiazolyl and pyridyl. Still more preferably, W is selected from imidazolyl and pyridyl.

Preferably, n is 0, 1, or 2.

Preferably, r is 1 or 2.

Preferably p is 1, 2 or 3.

Preferably s is 0 or 1.

Preferably, the moiety

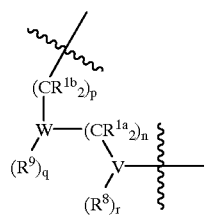

is selected from:

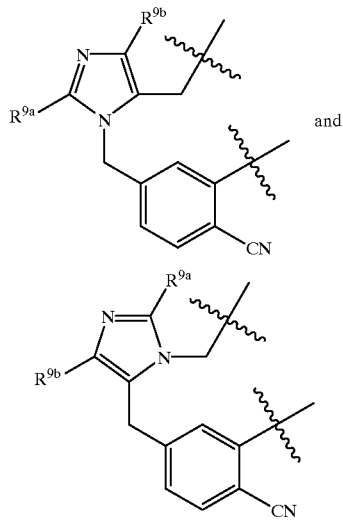

wherein $R^{9a}$ and $R^{9b}$ are independently selected from hydrogen or methyl.

Preferably, X is selected from —C(O)—, —OC(O)—, —C(O)—, —C(O)NR$^{10}$—, —NR$^{10}$C(O)—, O, —N(R$^{10}$)— and $S(O)_m$.

It is intended that the definition of any substituent or variable (e.g., $R^{1a}$, $R^9$, n, etc.) at a particular location in a molecule be independent of its definitions elsewhere in that molecule. Thus, —$N(R^{10})_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–11, in addition to other standard manipulations such as ester hydrolysis, cleavage of protecting groups, etc., as may be known in the literature or exemplified in the experimental procedures. Substituents $R^{sub}$ and $R^{sub'}$, as shown in the Schemes, represent the substituents and substituents on $Z^1$ and $Z^2$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 1–11

The requisite intermediates are in some cases commercially available, or can be prepared according to literature procedures. For example, syntheses of instant compounds wherein the linker "X" is an sulfonamido linkage is illustrated in Scheme 1. Thus, a suitably substituted benzylimidazolyl containing amine I is prepared as illustrated. A suitably substituted benzyl alcohol II is converted to the corresponding benzylsulfinylchloride III. Reaction of intermediate III with the primary amine I provides the sulfinamido intermediate IV. That intermediate can be oxidized to the sulfonamide, the alcohol moiety can then be deprotected and previously described intramolecular cyclization provides compound V of the instant invention.

Instant compounds wherein the variable "V" is other than a phenyl moiety can be prepared as illustrated in Scheme 2. Thus, a suitably substituted fluoronaphthylmethyl bromide VII may be reacted with an imidazolyl alkylacetate to provide intermediate VIII. The alcohol moiety of intermediate VIII can be deprotected and then reacted with a suitably substituted phenyl isocyanate to provide the carbamate IX, which may then be optionally N-alkylated, followed by deprotection and intramolecular cyclization to provide compound XI of the instant invention.

Synthesis of compounds of the instant invention wherein variables "$Z^1$" and "$Z^2$" are both phenyl moieties and the linker "X" is a amido moiety is illustrated in Scheme 3. Scheme 4 illustrates preparation of the corresponding instant compound wherein linker "X" is a urea moiety by reacting the isocyanate derived from intermediate I and the phenoxyanaline XIII described in Scheme 3. Synthesis of compounds of the instant invention wherein variable "$Z^1$" is a naphthyl moiety and the linker "X" is a amido moiety is illustrated in Scheme 5.

Scheme 10 illustrates the synthetic strategy that is employed when the $R^8$ substituent is not an electronic withdrawing moiety either ortho or para to the fluorine atom. In the absence of the electronic withdrawing moiety, the intramolecular cyclization can be accomplished via an Ullmann reaction. Thus, the aldehyde XIV can be converted to the homologous amine XV. Amine XV is then reacted with the previously described benzyloxybenzoic acid XVI to provide intermediate XVII. Intramolecular cyclization may then be affected under Ullmann reaction conditions to provide the amido macrocycle of the instant invention XVIII.

Schemes 7–10 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

Scheme 11 depicts the synthesis of compounds of the instant invention having an imidazolyl moiety incorporated into the macrocyclic ring via different points of attachement. Activated zinc is added to a fluoroaryl methylhalide in THF to form the arylmethyl zinc halide, which is subsequently coupled to an N-protected 4-iodoimidazole to give compound XIX. Regiospecfic alkylation of the imidazole ring is accomplished with ethyl bromoacetate, with subsequent methanolysis of the intermediate imidazolium salt giving XX. Elaboration of XX to the primary amine proceeds through standard chemistry. Acylation of the amine with suitably substituted aryl carboxylic acid (similar to the reaction illustrated in Scheme 5) provides the intermediate amide, which can then undergo cyclization as described above to provide the compound of the instant invention XXI.

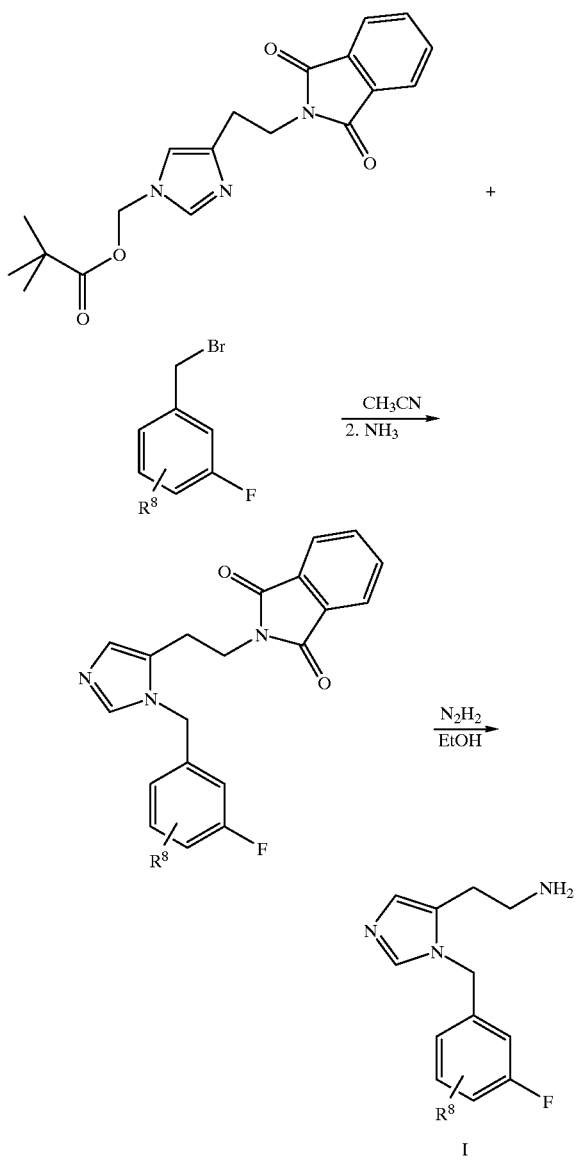

SCHEME 1

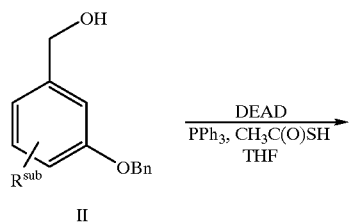
II
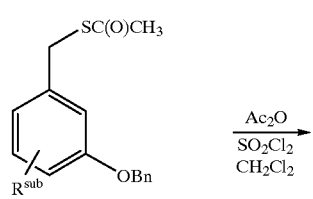
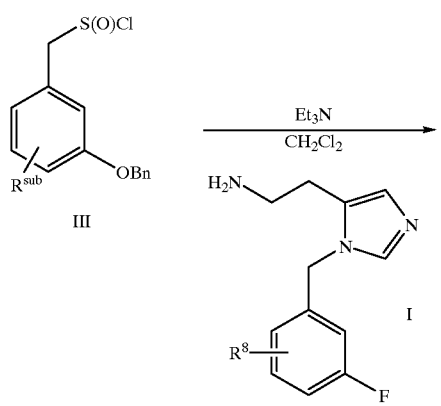
III
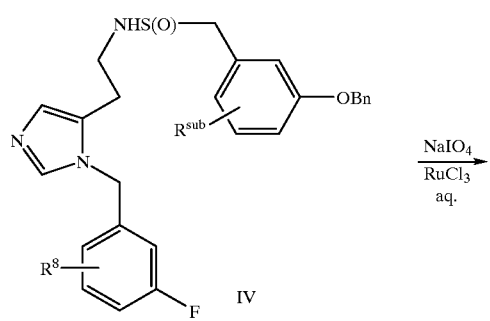
IV
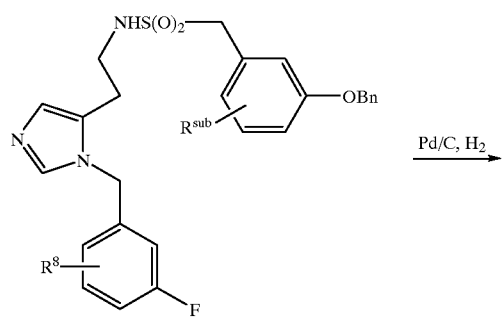
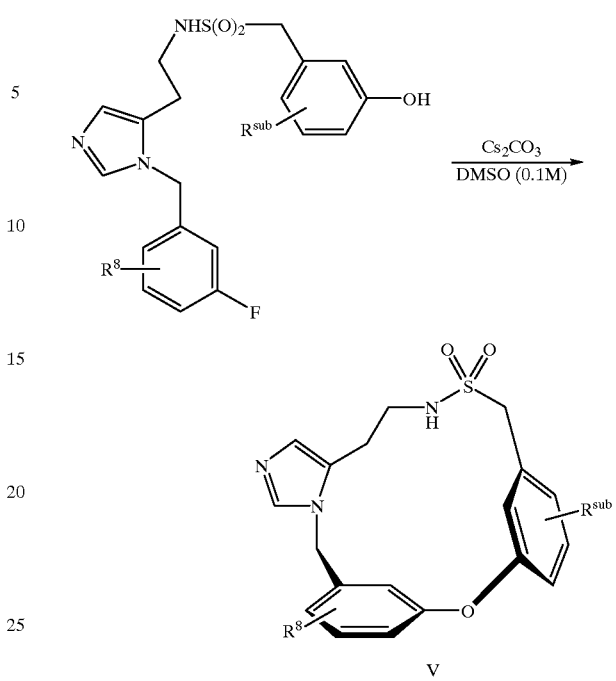
V
SCHEME 2
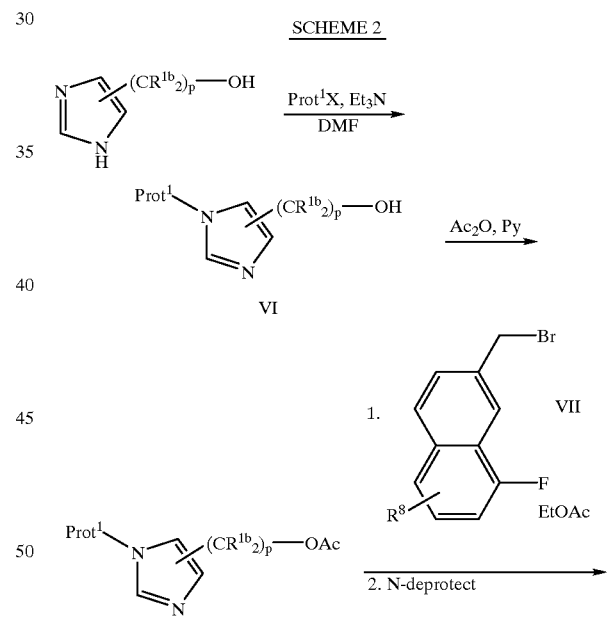

-continued
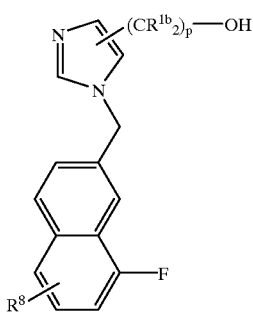
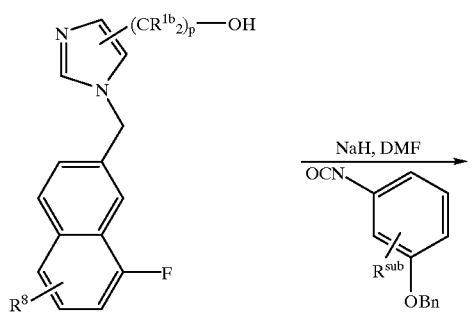
NaH, DMF
OCN—[ArRsub(OBn)]
→
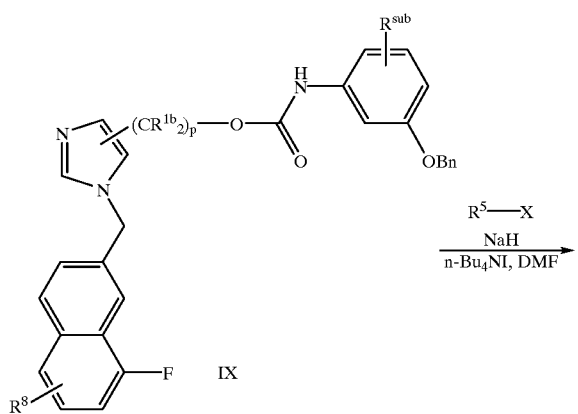
IX
R5—X
NaH
n-Bu4NI, DMF
→
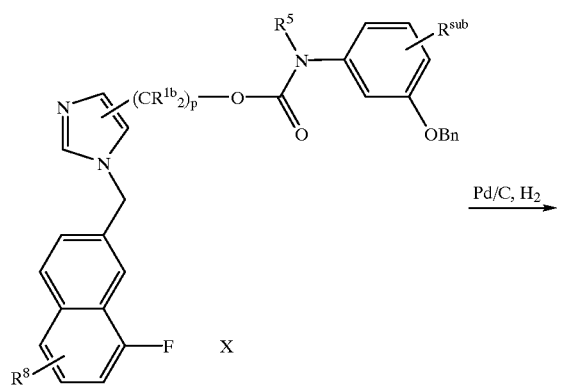
X
Pd/C, H2
→
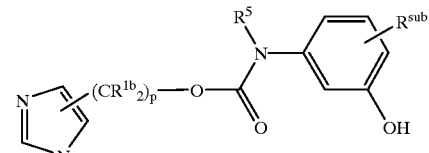
Cs2CO3
DMSO (0.1M)
→
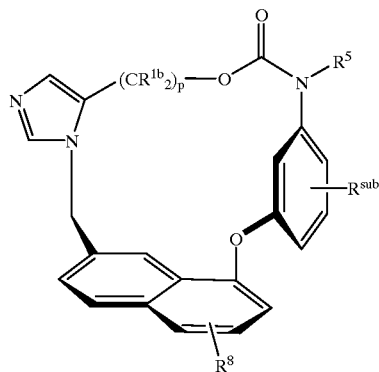
XI
SCHEME 3
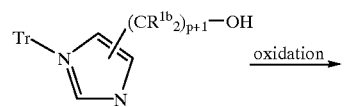
TrCl, Et3N
DMF
→
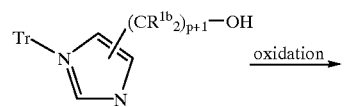
oxidation
→
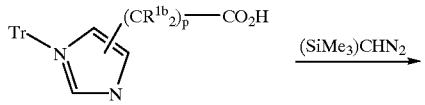
(SiMe3)CHN2
→
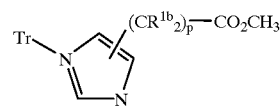
1. [BrCH2-Ar(R6)-F]
   EtOAc
2. MeOH
→

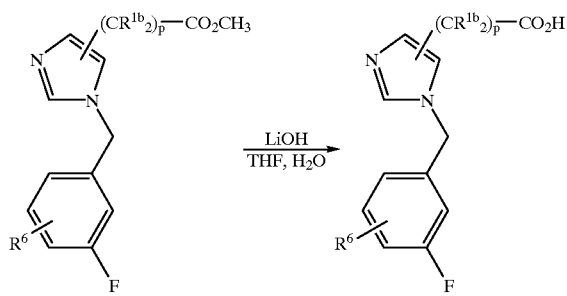
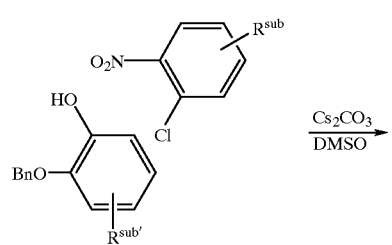
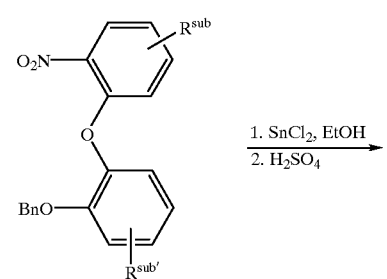
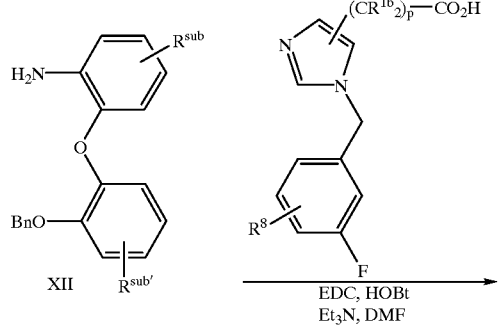
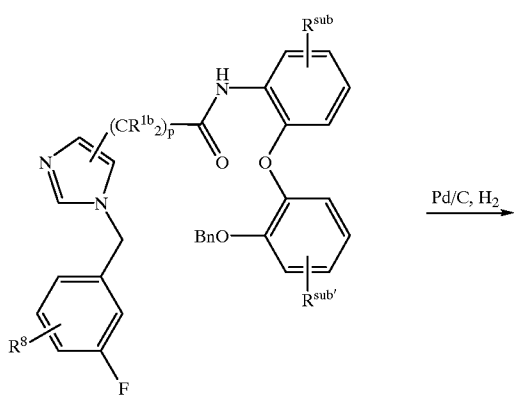
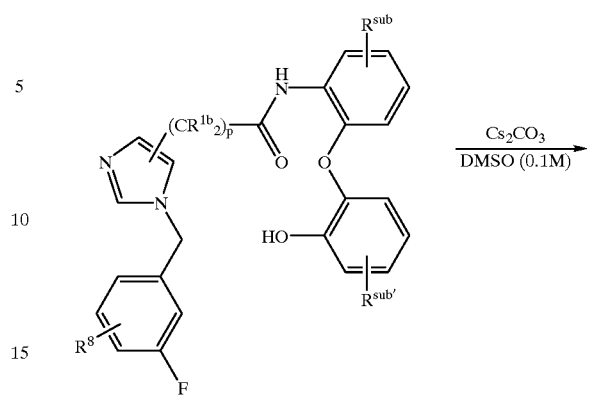
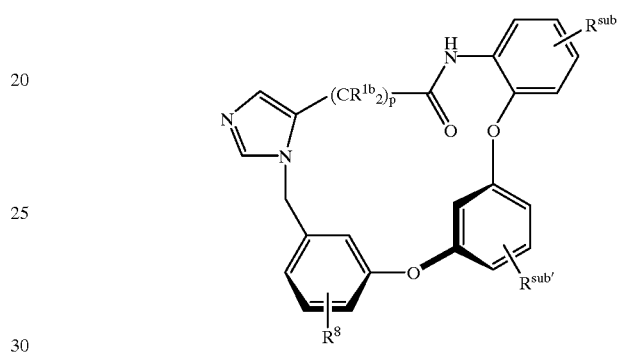
SCHEME 4
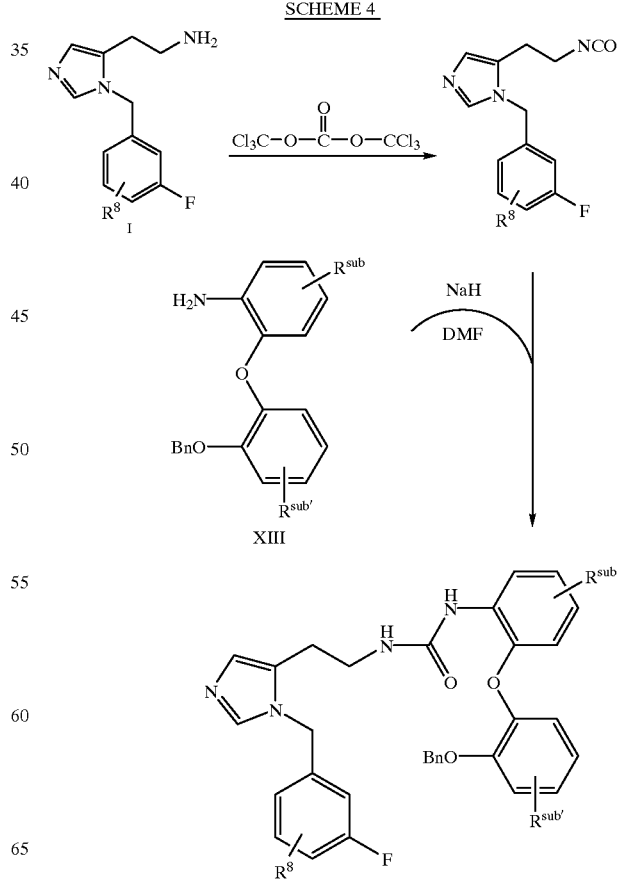

-continued
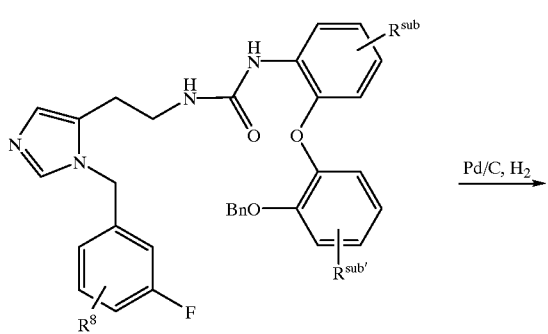
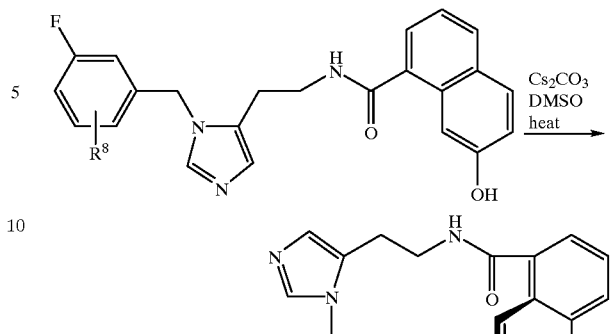
SCHEME 6
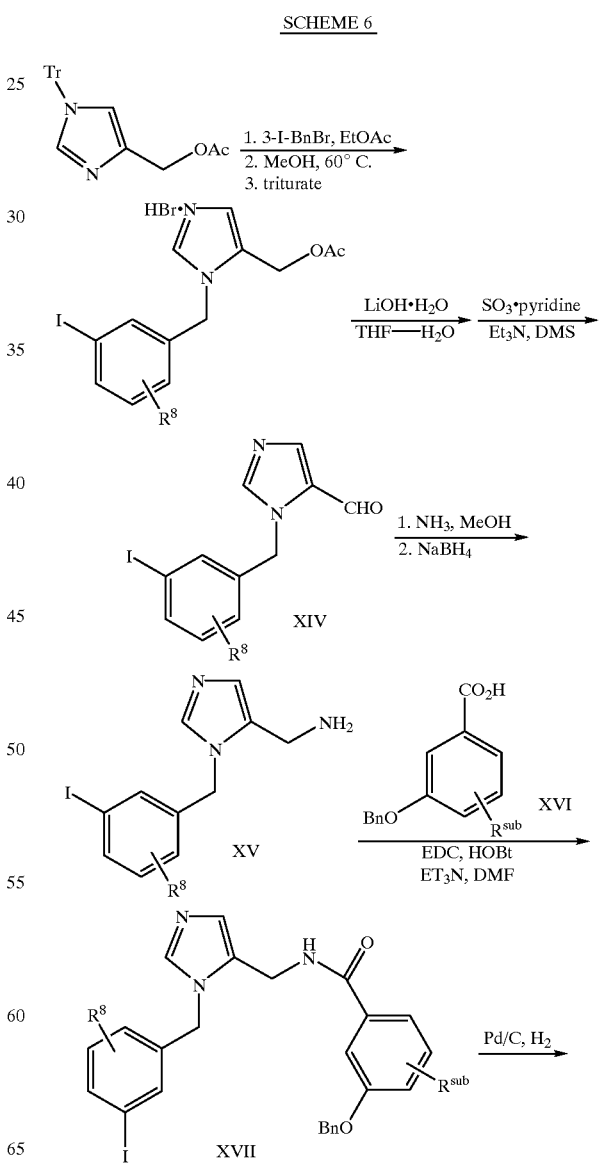
SCHEME 5
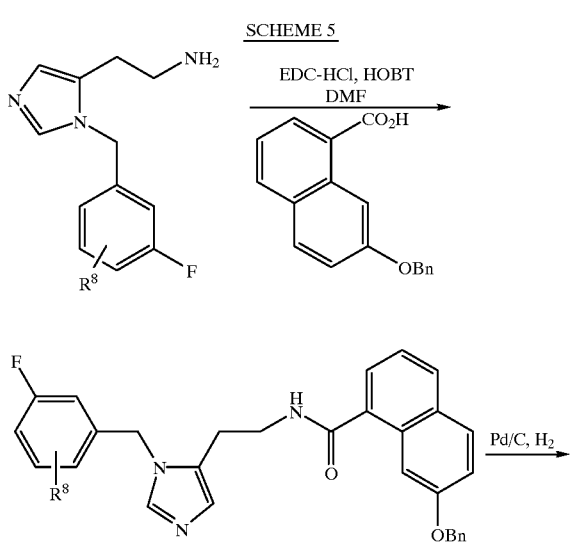

-continued
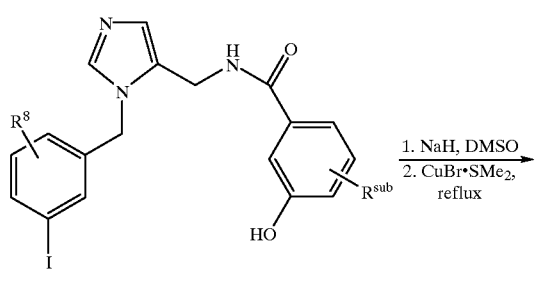
SCHEME 7
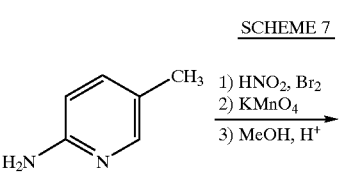
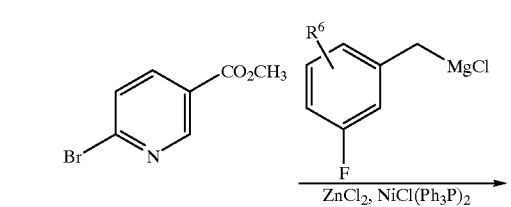
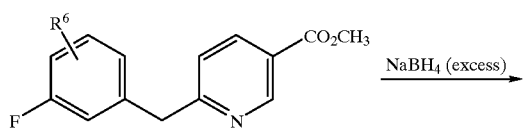
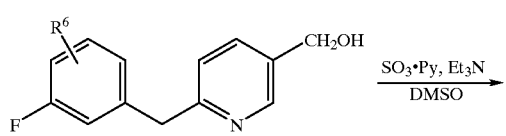
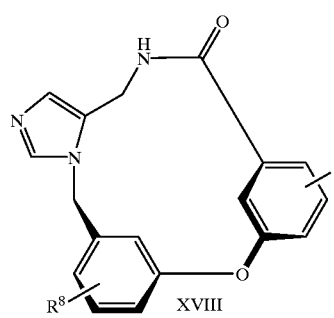
SCHEME 8
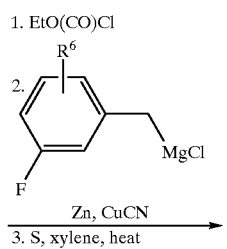
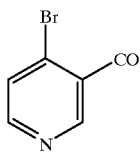
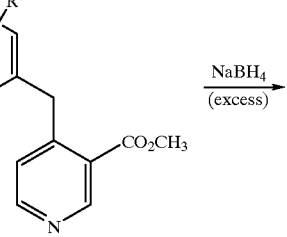
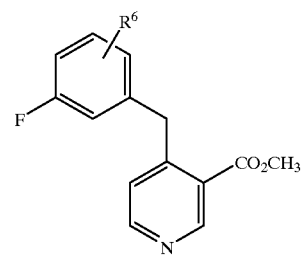
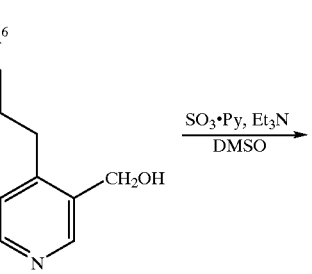
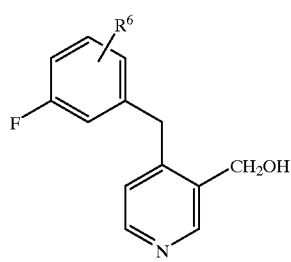
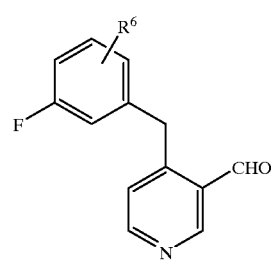
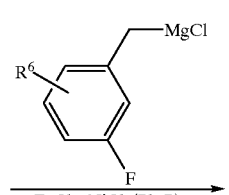
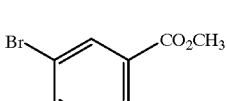
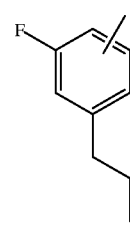

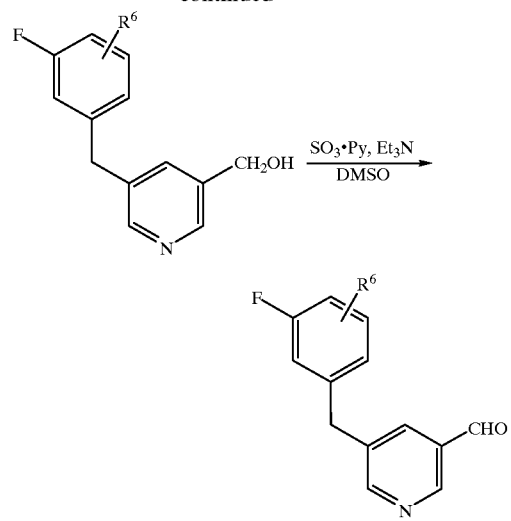
SCHEME 9
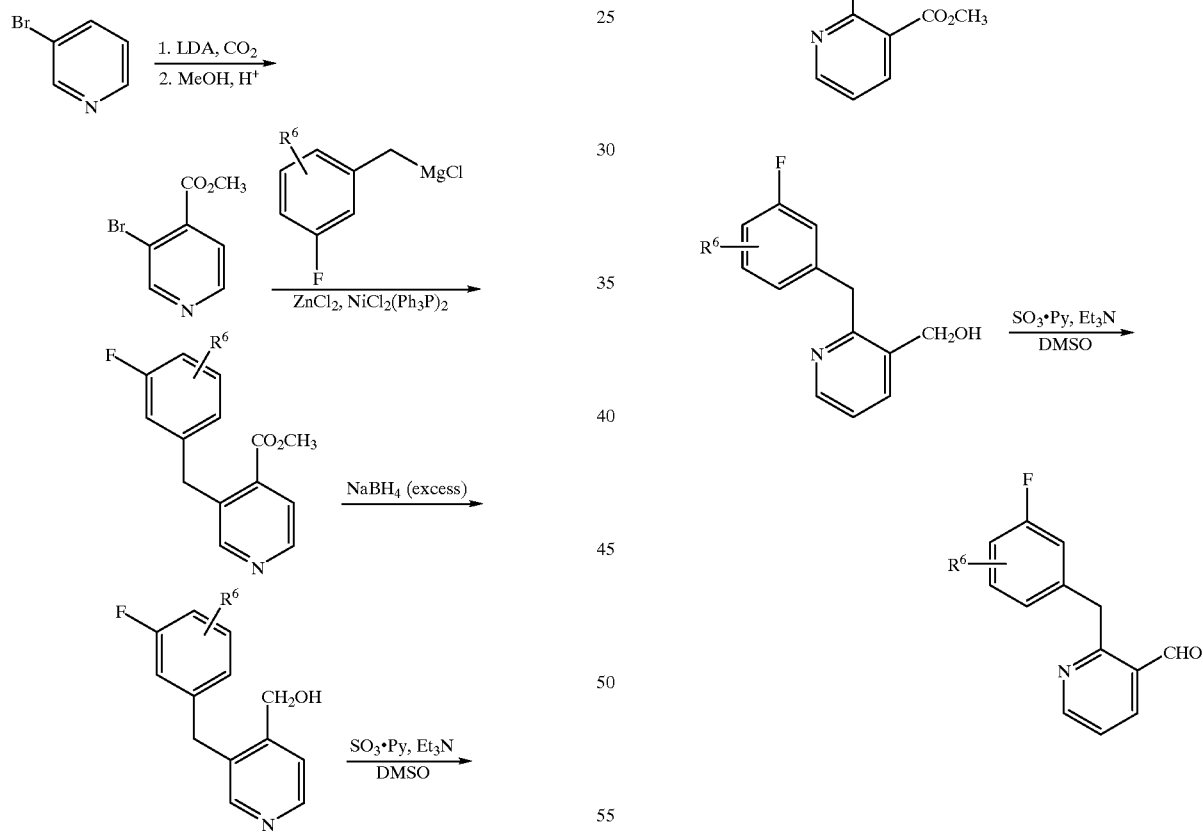
SCHEME 10
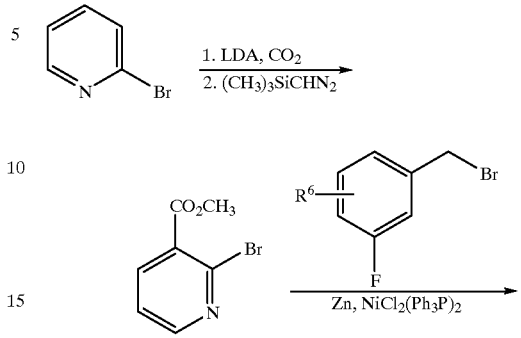
SCHEME 11
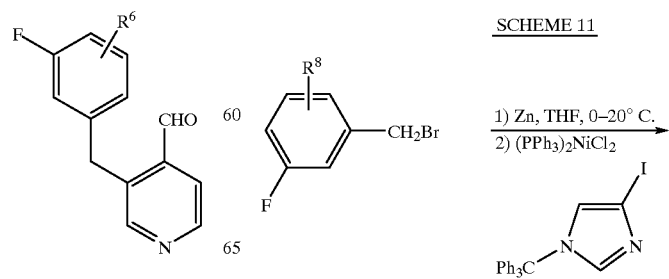

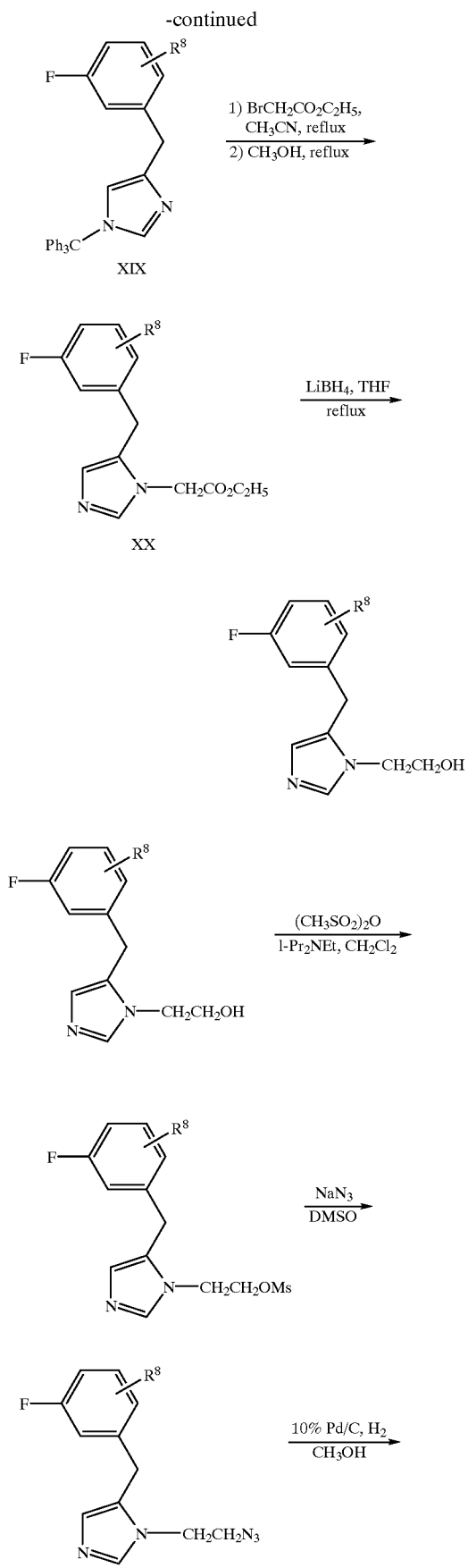
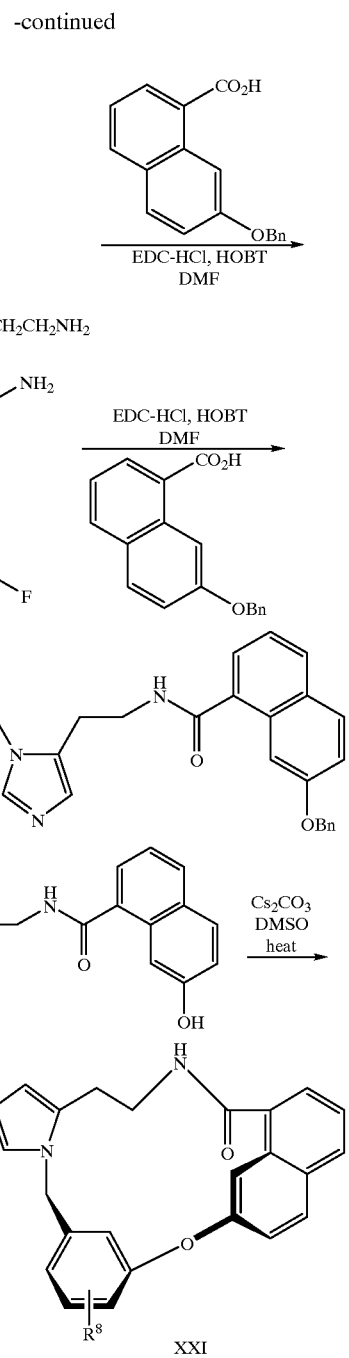

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 21, is at least 100 times greater than the in vitro activity of the same compound against geranylgeranyl-protein transferase-type I in the assay described in Example 22. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:

a) an $IC_{50}$ (a measure of in vitro inhibitory activity) for inhibition of the prenylation of newly synthesized K-Ras protein more than about 100-fold higher than the $EC_{50}$ for the inhibition of the farnesylation of hDJ protein.

When measuring such $IC_{50}$s and $EC_{50}$s the assays described in Example 26 may be utilized.

It is also preferred that the selective inhibitor of farnesyl-protein transferase is further characterized by:

b) an $IC_{50}$ (a measurement of in vitro inhibitory activity) for inhibition of K4B-Ras dependent activation of MAP kinases in cells at least 100-fold greater than the $IC_{50}$ for inhibition of the farnesylation of the protein hDJ in cells.

It is also preferred that the selective inhibitor of farnesyl-protein transferase is further characterized by:

c) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 25 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Examples 25, it is preferred that the dual inhibitor compound has an in vitro inhibitory activity ($IC_{50}$) that is less than about 12 $\mu$M against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 25.

In yet another embodiment, a compound of the instant invention may be a more potent inhibitor of geranylgeranyl-protein transferase-type I than it is an inhibitor of farnesyl-protein transferase.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit prenyl-protein transferase and the prenylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al.*FASEB Journal*, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug.

These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that such a combination of antineoplastic agent and inhibitor of prenyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents, haematopoietic growth factors and antibodies (such as trastuzumab (Herceptin™)).

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase.

In particular, if the compound of the instant invention is a selective inhibitor of farnesyl-protein transferase, co-administration with a compound(s) that is a selective inhibitor of geranylgeranyl protein transferase may provide an improved therapeutic effect.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the α1β1, α2β1, α5β1, α6β1 and α6β4 integrins. The term also refers to antagonists of any combination of αvβ3 integrin, αvβ5 integrin, α1β1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immuno-logical, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of 18,19-dihydro-19-oxo-5H,17H-6, 10:12,16-dimetheno-1H-imidazo[4,3-c][1,11,4] dioxaazacyclononadecine-9-carbonitrile (1), hydrochloride salt

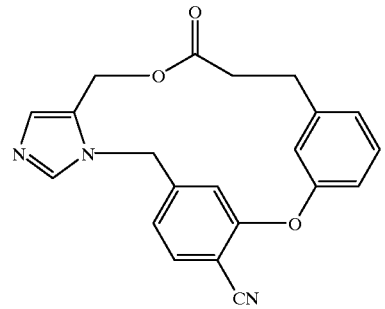

1

Step A: Preparation of 1-triphenylmethyl-4-(hydroxymethyl)imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next reaction.

Step C: Preparation of 4-cyano-3-fluorotoluene

To a degassed solution of 4-bromo-3-fluorotoluene (50.0 g, 264 mmol) in 500 mL of DMF was added Zn(CN)$_2$ (18.6 g, 159 mmol) and Pd(PPh$_3$)$_4$ (6.1 g, 5.3 mmol). The reaction was stirred at 80° C. for 6 hours, then cooled to room temperature. The solution was poured into EtOAc, washed with water, sat. aq. NaHCO$_3$, and brine, then dried (Na$_2$SO$_4$), filtered, and concentrated in vacuo to provide the crude product. Purification by silica gel chromatography (0–5% EtOAc/hexane) provided the titled product.

Step D: Preparation of 4-cyano-3-fluorobenzylbromide

To a solution of the product from Step C (22.2 g, 165 mmol) in 220 mL of carbontetrachloride was added N-bromosuccinimide (29.2 g, 164 mmol) and benzoylperoxide (1.1 g). The reaction was heated to reflux for 30 minutes, then cooled to room temperature. The solution was concentrated in vacuo to one-third the original volume, poured into EtOAc, washed with water, sat. aq. NaHCO$_3$, and brine, then dried (Na$_2$SO$_4$), filtered, and concentrated in vacuo to provide the crude product. Analysis by $^1$H NMR indicated only partial conversion, so the crude material was resubjected to the same reaction conditions for 2.5 hours, using 18 g (102 mmol) of N-bromosuccinimide. After workup, the crude material was purified by silica gel chromatography (0–10% EtOAc/hexane) to provide the desired product.

Step E: Preparation of 1-(4-cyano-3-fluorobenzyl)-5-(acetoxymethyl)-imidazole hydrobromide A solution of the product from Step B (36.72 g, 96.14 mmol) and the product from Step D (20.67 g, 96.14 mmol) in 250 mL of EtOAc was stirred at 60° C. for 20 hours, during which a white precipitate formed. The reaction was cooled to room temperature and filtered to provide the solid imidazolium bromide salt. The filtrate was concentrated in vacuo to a volume 100 mL, reheated at 60° C. for two hours, cooled to room temperature, and filtered again. The filtrate was concentrated in vacuo to a volume 40 mL, reheated at 60° C. for another two hours, cooled to room temperature, and concentrated in vacuo to provide a pale yellow solid. All of the solid material was combined, dissolved in 300 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step F: Preparation of 1-(4-cyano-3-fluorobenzyl)-5-(hydroxymethyl)imidazole

To a solution of the product from Step E (31.87 g, 89.77 mmol) in 300 mL of 2:1 THF/water at 0° C. was added lithium hydroxide monohydrate (7.53 g, 179 mmol). After two hours, the reaction was concentrated in vacuo to a 100 mL volume, stored at 0° C. for 30 minutes, then filtered and washed with 700 mL of cold water to provide a brown solid. This material was dried in vacuo next to P$_2$O$_5$ to provide the titled product as a pale brown powder which was sufficiently pure for use in the next step without further purification.

Step G: Preparation of 1-(4-cyano-3-fluorobenzyl)-5-[((3-(3-hydroxyphenyl)propionyl)oxy)methyl]imidazole To a solution of the alcohol from Step F (79.7 mg, 0.345 mmol) and triphenylphosphine (90.0 mg, 0.345 mmol) in 0.5 mL of THF was added a solution of diethylazodicarboxylate (0.054 mL, 0.345 mmol) and 3-(3-hydroxyphenyl)propionic acid (57 mg, 0.34 mmol) in 0.5 mL of THF. After 10 minutes, HPLC analysis indicated 60% conversion. Additional triphenylphosphine (45 mg, 0.17 mmol) and diethylazodicarboxylate (0.027 mL, 0.17 mmol) were added, and the reaction was stirred for 10 more minutes. The solution was concentrated in vacuo, then purified by silica gel chromatography (3% MeOH/CH$_2$Cl$_2$) to provide the desired product as a white foam.

Step H: Preparation of Compound 1, hydrochloride salt

To a solution of the phenol from Step G (54 mg, 0.14 mmol) in 1.0 mL of DMSO was added cesium carbonate (92 mg, 0.28 mmol). The reaction was warmed to 55° C. for 20 minutes, then cooled to room temperature. The solution was poured into EtOAc, washed with sat. aq. NaHCO$_3$ and brine, dried (Na$_2$SO$_4$), filtered, and concentrated in vacuo. The resulting product was purified by silica gel chromatography (3–4% MeOH/CH$_2$Cl$_2$), taken up in CH$_2$Cl$_2$ and treated with excess 1 M HCl/ether solution, and concentrated in vacuo to provide the titled product hydrochloride as a white powder.

FAB mass spectrum m/e 360.1 (M+1).

Analysis calculated for C$_{21}$H$_{17}$N$_3$O$_3$.1.00 HCl.1.00 H$_2$O: C, 60.95; H, 4.87; N, 10.15;

Found: C, 60.84; H, 4.88; N, 10.12.

Example 2

Preparation of 17,18-dihydro-18-oxo-5H-6,10:12,16-dimetheno-12H,20H-imidazo[4,3-c][1,11,4]dioxaazacyclooctadecine-9-carbonitrile (2), hydrochloride salt

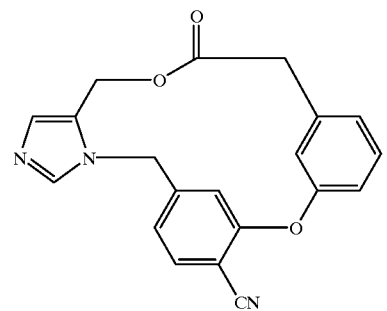

The titled product was prepared from the alcohol prepared in step F of Example 1 and (3-hydroxyphenyl)acetic acid using the procedures described in Steps G and H of Example 1.

FAB mass spectrum m/e 346.0 (M+1).

Analysis calculated for C$_{20}$H$_{15}$N$_3$O$_3$.1.60 HCl.1.30 H$_2$O: C, 56.24; H, 4.53; N, 9.84;

Found: C, 56.37; H, 4.51; N, 9.32.

Example 3

Preparation of (±)-17,18,19,20-tetrahydro-19-phenyl-5H-6,10:12,16-dimetheno-21H-imidazo[3,4-h][1,8,11]oxadiazacyclononadecine-9-carbonitrile (3), hydrochloride salt

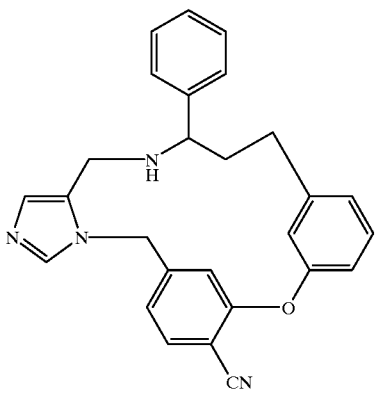

3

Step A: Preparation of 3-(3-methoxypheny)-1-phenylpropanol

To a solution of benzaldehyde (920 μl, 9 mmol) in dry THF (20 mL) was added slowly a solution of 2-(3-methoxyphenyl) ethylmagnesium bromide prepared from 2-(3-methoxyphenyl) ethyl bromide (2.1 g. 9.77 mmol) and magnesium (300 mg, 12 mmol). The mixture was stirred at room temperature for ½ hour then quenched with saturated $NH_4Cl$. The mixture was then extracted into EtOAc, washed with $H_2O$, dried ($Na_2SO_4$), filtered and concentrated in vacuo, then purified by silica gel chromatography (30% EtOAc/Hexane) to provide the desired product as a colorless viscous oil.

Step B: Preparation of 1-azido-3-(3-methoxyphenyl)-1-phenylpropane

To a solution of the product from Step A (1.36 g, 5.6 mmol) in 20 mL of THF at 0° C. under Ar was added triphenylphosphine (1.8 g, 6.9 mmol), diethylazodicarboxylate (1.12 mL, 6.9 mmol) and diphenylphosphoryl azide (1.52 mL, 6.9 mmol). The ice-bath was removed and the reaction mixture was stirred at ambient temperature for 20 hours. The reaction was concentrated in vacuo and purified by silica gel chromatography (2% EtOAc/Hexane) to provide the desired product as a nearly colorless gum.

Step C: Preparation of 3-(3-methoxyphenyl)-1-phenylpropylamine

A solution of the product from Step B (1.08 g, 3.7 mmol) in 30 mL of EtOH containing Pd/C (10%, 100 mg) was stirred at ambient temperature under 1 Atm. of $H_2$ for 20 hours. The reaction mixture was filtered to provide the title product as a clear colorless oil which was sufficiently pure for use in the next step.

Step D: Preparation of 3-(3-amino-3-phenylpropyl) phenol

A mixture of the product from Step C (920 mg), HOAc (2 mL) and 48% HBr (3 mL) was stirred while heating at reflux. After 2–3 hours, the solution was concentrated in vacuo to provide a pale beige sticky solid which was triturated with $Et_2O$. Removal of residual solvents in vacuo provided the titled product hydrobromide as a pale beige froth.

Step E: Preparation of 3-(4-cyano-3-fluorobenzyl)-4-[3-(3-hydroxyphenyl)-1-phenylpropylaminomethyl]imidazole A solution of the product from Step D (185 mg. 600 μmol) and aldehyde from Example Z (100 mg. 500 μmol) in 3 mL of MeOH was treated with 4-methylmorpholine (55 μL) to adjust pH to ~7.5–8.0 at room temperature. After 20 hours $NaBH_4$ (60 mg, 1.5 mmol) was added and stirring was continued for an additional hour. The reaction mixture was then passed down a silica gel column with (1–10% $CH_3H$/$CHCl_3$) to provide the desired product.

Step F: Preparation of Compound 3 hydrochloride

The compound was prepared from the product of Step E (78 mg, 175 μmol) using the method described in Example 1 Step H provided the title product as a white solid.

Example 4

Preparation of 21,22-dihydro-5H-6,10:12,16-dimetheno-23H-benzo[g]imidazo[4,3-1][1,8,11]oxadiazacyclononadecine-9-carbonitrile (4), hydrochloride salt

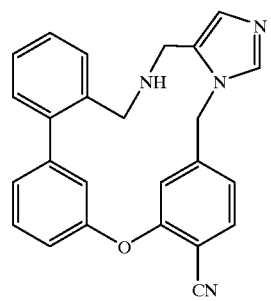

4

Step A: Preparation of ethyl 2-(3'-methoxyphenyl) benzoate

To a stirred solution of ethyl 2-bromobenzoate (13.7 g, 59.8 mmol) and tetrakis(triphenylphosphine)palladium(0) (3.46 g, 3.0 mmol) in 1,2-dimethoxyethane (600 mL) was added 2 M aq. $Na_2CO_3$ (60 mL, deoxygenated). 3-Methoxyphenylboronic acid (10.0 g, 65.8 mmol) was added in 1,2-dimethoxyethane (80 mL) and the mixture was heated to 100° C. for 36 hours, under argon atmosphere. The mixture was cooled, diluted with water (1 L) and extracted with EtOAc (2×800 mL). The combined organic extracts were washed with sat. aq. $NaHCO_3$, then brine, then dried over $Na_2SO_4$, filtered and concentrated under reduced pressure. The residue was purified by flash column chromatography, eluting with a gradient of 0–10% EtOAc in hexane, to give the titled product as a colorless oil.

Step B: Preparation of 2-(3'-methoxyphenyl) benzoic acid

To a stirred solution of ethyl 2-(3-methoxyphenyl) benzoate from Step A (7.33 g, 28.6 mmol) in MeOH (200 mL) and water (30 mL) was added 1.0 N aq. NaOH (63 mL, 63 mmol) dropwise. The mixture was heated to reflux for 3 hours, then allowed to cool overnight. The solution was concentrated to remove most of the MeOH, cooled on ice, and 10% aq. citric acid (300 mL) was added. The resulting mixture was extracted with $CH_2Cl_2$ (3×250 mL), and the combined organic extracts were dried over $Na_2SO_4$, filtered, and concentrated under reduced pressure to give the titled product as a white solid.

Step C: Preparation of 2-(3'-hydroxyphenyl)benzoic acid 2-(3-Methoxyphenyl)benzoic acid from Step B (6.53 g, 28.6 mmol) was dissolved in dry $CH_2Cl_2$ (100 mL) under argon and cooled to −78° C. Boron tribromide (62.9 mL of a 1.0 M solution in $CH_2Cl_2$, 62.9 mmol) was added dropwise and the solution was stirred overnight and allowed to warm slowly to ambient temperature. The resulting mixture was cooled in an ice bath and quenched carefully with water (200 mL), then extracted with $CH_2Cl_2$ (3×250 mL). The combined organic extracts were dried over $Na_2SO_4$, filtered, and concentrated under reduced pressure to give the titled product which was sufficiently pure for use in the next step.

Step D: Preparation of benzyl 2-(3'-benzyloxyhenyl)benzoate

To a stirred solution of 2-(3-hydroxyphenyl)benzoic acid from Step C (28.6 mmol, prepared above) in acetone (100 mL) were added $K_2CO_3$ (8.7 g, 63 mmol) and benzyl bromide (10.8 g, 63 mmol). The mixture was stirred under argon, overnight, then heated to reflux for 7 hours. The acetone was removed under reduced pressure and the residue was partitioned between water (100 mL) and $CH_2Cl_2$ (250 mL). The aqueous layer was extracted further with $CH_2Cl_2$ (2×250 mL). The combined organic extracts were dried over $Na_2SO_4$, filtered, and concentrated under reduced pressure. The residue was purified by flash column chromatography, eluting with a gradient of 70–0% hexane in $CH_2Cl_2$, to give the titled product as a colorless oil.

Step E: Preparation of (3'-benzyloxybiphenyl-2-yl) methanol

A solution of benzyl 2-(3'-benzyloxyphenyl)benzoate from Step D (1.35 g, 3.42 mmol) in dry THF (20+10 mL) was added dropwise to a stirred suspension of $LiAlH_4$ (0.26 g, 6.84 mmol) in THF (30 mL) at 0° C., under argon. Stirring was continued for 1 hour at 0° C., then the reaction was quenched with wet ether, followed by water, then aq. $NH_4Cl$. The resulting mixture was extracted with EtOAc (2×100 mL), and the combined organic extracts were dried over $Na_2SO_4$, filtered, and concentrated under reduced pressure to give a crude product which contained benzyl alcohol. Vacuum distillation (1 mm Hg, 80° C.) allowed removal of most of the benzyl alcohol to give the titled product as a pale solid.

Step F: Preparation of 2-azidomethyl-3'-benzyloxybiphenyl

To a stirred solution of (3'-benzyloxybiphenyl-2yl) methanol from Step E (0.994 g, 3.42 mmol) and diphenylphosphoryl azide (1.13 g, 4.10 mmol) in dry toluene (6 mL) at 0° C., under argon, was added 1,8-diazabicyclo [5.4.0]undec-7-ene (0.62 g, 4.10 mmol) dropwise. The resulting mixture was stirred and allowed to warm to ambient temperature overnight. Toluene (6 mL) was added and the mixture was washed with water (2×5 mL), then 1.0 N aq. HCl (5 mL), then dried over $Na_2SO_4$, filtered, and concentrated under reduced pressure. The residue was purified by flash column chromatography, eluting with 5% EtOAc in hexane, to give the titled product as a colorless oil.

Step G: Preparation of 2-{N-(tert-butyloxycarbonyl) aminomethyl}-3'-hydroxybiphenyl A mixture of 2-azidomethyl-3'-benzyloxybiphenyl from Step F (0.882 g, 2.80 mmol), di-tert-butyl dicarbonate (0.64 g, 2.93 mmol), and 10% Pd-C (0.18 g) in EtOAc (28 mL) was stirred under an atmosphere of hydrogen (ca. 1 atm) for 10 hours. The reaction mixture was filtered through a celite pad, washing with EtOAc, and the filtrate was concentrated under reduced pressure. The residue was purified by flash column chromatography, eluting with a gradient of 10–30% EtOAc in hexane, to give the titled product.

Step H: Preparation of 2-aminomethyl-3'-hydroxybiphenyl hydrochloride

A solution of 2-{N-(tert-butyloxycarbonyl) aminomethyl}-3'-hydroxybiphenyl from Step G (0.732 g, 2.45 mmol) in EtOAc (30 mL) at 0° C. was saturated with HCl gas. The mixture was aged at 0° C. for 5 min, then concentrated to dryness in vacuo to provide the titled compound as a white solid.

Step I: Preparation of 2-fluoro-4-(5-{[(3'-hydroxybiphenyl-2-ylmethyl)amino] methyl}imidazol-1-ylmethyl)benzonitrile 2-Aminomethyl-3'-hydroxybiphenyl hydrochloride from Step H (129 mg, 0.548 mmol) and 1-(4-cyano-3-fluorobenzyl)-5-imidazolecarboxaldehyde from Example 3, Step G (132 mg, 0.576 mmol) were stirred in MeOH (2 mL) for 30 min, then $NaCNBH_3$ (38 mg, 0.60 mmol) was added. The reaction mixture was adjusted to pH 5 with AcOH, as judged from wetted pH paper, and stirring was continued at ambient temperature for 3 days. The reaction was quenched with 10% aq. citric acid and stirred for 20 min. Sat. aq. $NaHCO_3$ (10 mL) was added and the mixture was extracted with $CH_2Cl_2$ (4×20 mL). The combined organic extracts were dried over $Na_2SO_4$, filtered, and concentrated under reduced pressure. The titled product was crystallized from $CH_2Cl_2$-hexane and the first crop of white needles used for the next reaction.

Step J: Preparation of Compound 4, hydrochloride

A stirred mixture of 2-fluoro-4-(5-{[(3'-hydroxybiphenyl-2-ylmethyl)amino]methylimidazol-1-ylmethyl)benzonitrile from Step I (91 mg, 0.221 mmol) and $Cs_2CO_3$ (108 mg, 0.331 mmol) in dry, degassed DMF (4 mL) under argon was heated to 45° C. for 23 hours, then poured into aq. $NaHCO_3$ and extracted with EtOAc (3×25 mL). The combined organic extracts were dried over $Na_2SO_4$, filtered, and concentrated under reduced pressure. The residue was purified by flash column chromatography, eluting with a gradient of 1–7% MeOH in 0.5% $NH_4OH/CH_2Cl_2$ to give the desired product which was treated with HCl in EtOAc to give the hydrochloride salt as a white powder.

FAB mass spectrum m/e 393.4 (M+1).

Analysis calculated for $C_{25}H_{20}N_4O$.2 HCl.0.7 $H_2O$.0.3 EtOAc: C, 62.38; H, 5.16; N, 11.11;

Found: C, 62.34; H, 4.93; N, 11.09.

Example 5

Preparation of 22,23-dihydro-23-oxo-5H,21H-6,
10:12,16-dimetheno-24H-benzo[g]imidazo[4,3-m]
[1,8,12]oxadiazaeicosine-9-carbonitrile (5),
hydrochloride salt

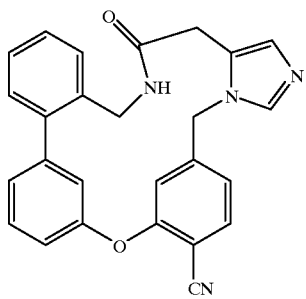

Step A: Preparation of methyl imidazol-4-ylacetate hydrochloride

A solution of 4-imidazoleacetic acid hydrochloride (4.0 g, 24.6 mmol) in MeOH (100 mL) was saturated with HCl gas at ambient temperature. Trimethyl orthoformate (10 mL) was added, and the mixture was stirred at ambient temperature overnight then concentrated to dryness in vacuo. The solid was redissolved in MeOH (100 mL) and the above procedure repeated to yield the titled compound as a white solid.

Step B: Preparation of methyl 1-(triphenylmethyl)imidazol-4-ylacetate

To a stirred solution of methyl imidazol-4-ylacetate hydrochloride from Step A (4.30 g, 24.3 mmol) in dry DMF (50 mL) under argon were added triethylamine (5.41 g, 53.5 mmol) and triphenylmethyl bromide (8.64 g, 26.7 mmol). The reaction mixture was stirred at ambient temperature overnight, then partitioned between water (250 mL) and EtOAc (250 mL). The organic layer was dried over $Na_2SO_4$, filtered, and concentrated under reduced pressure. The residue was purified by flash column chromatography, eluting with 50% hexane in EtOAc to remove nonpolar impurities, then EtOAc to elute the titled product as a white solid.

Step C: Preparation of methyl 1-(4-cyano-3-fluorobenzyl)imidazol-5-ylacetate A solution of methyl 1-(triphenylmethyl)imidazol-4-ylacetate from Step B (0.536 g, 1.40 mmol) and 4-cyano-3-fluoro-benzylbromide from Example 1, Step D (0.300 g, 1.40 mmol) in dry acetonitrile (3 mL) was heated at 50° C. under argon for 2 hours, then the precipitate was collected by filtration. The filtrate was concentrated to a volume of 1 mL and then heated at 50° C. for a further 2 hours. The precipitate formed was collected and combined with the first crop to give a white solid (0.63 g). This solid was dissolved in MeOH (30 mL) and heated to reflux for 2 hours. The MeOH was removed under reduced pressure and the residue was partitioned between sat. aq. $NaHCO_3$ (20 mL) and $CHCl_3$ (30 mL). The aqueous layer was extracted further with $CHCl_3$ (2×15 mL). The combined organic extracts were dried over $Na_2SO_4$, filtered, and concentrated under reduced pressure. The residue was purified by flash column chromatography, eluting with 3% MeOH/0.3% $NH_4OH$ in $CHCl_3$ to give the titled product as a white solid.

Step D: Preparation of lithium 1-(4-cyano-3-fluorobenzyl)-imidazol-5-ylacetate To a stirred solution of methyl 1-(4-cyano-3-fluorobenzyl)imidazol-5-ylacetate from Step C (260 mg, 0.95 mmol) in THF (5 mL) and water (1 mL) was added LiOH (40 mg, 0.95 mmol). The reaction mixture was stirred at ambient temperature for 1 hour, then the solution was adjusted to pH 7 with 1 N aq. HCl and concentrated to dryness in vacuo to provide the titled product as a white solid which was sufficiently pure for use in the next step.

Step E: Preparation of N-(3'-hydroxybiphenyl-2-ylmethyl)-2-[3-(4-cyano-3-fluorobenzyl)-3H-imidazol-4-yl]acetamide A solution of lithium 1-(4-cyano-3-fluorobenzyl)imidazol-5-ylacetate from Step D (143 mg, 0.55 mmol), 2-aminomethyl-3'-hydroxybiphenyl hydrochloride from Example 4, Step H (118 mg, 0.50 mmol), 1-hydroxybenzotriazole hydrate (74 mg, 0.55 mmol), EDC (105 mg, 0.55 mmol), and diisopropylethylamine (129 mg, 1.00 mmol) in dry, degassed DMF (2 mL) was stirred at ambient temperature overnight. The solvent was removed under reduced pressure and the residue was partitioned between sat. aq. $NaHCO_3$ (3 mL) and $CHCl_3$ (5 mL). The aqueous layer was extracted further with $CHCl_3$ (2×5 mL). The combined organic extracts were dried over $Na_2SO_4$, filtered, and concentrated under reduced pressure. The residue was purified by flash column chromatography, eluting with a gradient of 3–5% MeOH/0.3–0.5% $NH_4OH$ in $CHCl_3$ to give the titled product as a white foam.

Step F: Preparation of Compound 5 hydrochloride

A stirred mixture of N-(3'-hydroxybiphenyl-2-ylmethyl)-2-[3-(4-cyano-3-fluorobenzyl)-3H-imidazol-4-yl]acetamide from Step E (200 mg, 0.454 mmol) and $Cs_2CO_3$ (222 mg, 0.681 mmol) in dry, degassed DMF (4 mL) under argon was heated to 50° C. for 18 hours. The solvent was removed under reduced pressure and the residue was partitioned between sat. aq. $NaHCO_3$ (10 mL) and $CH_2Cl_2$ (15 mL). The aqueous layer was extracted further with $CH_2Cl_2$ (2×5 mL). The combined organic extracts were dried over $MgSO_4$, filtered, and concentrated under reduced pressure. The residue was purified by flash column chromatography, eluting with 3% MeOH/0.2% $NH_4OH$ in $CH_2Cl_2$ to give the desired product, which was treated with HCl in acetonitrile—water and lyophilized to give the titled compound as a white solid.

FAB mass spectrum m/e 421 (M+1).

Analysis calculated for $C_{26}H_{20}N_4O_2 \cdot 0.6$ HCl$\cdot 2.0$ $H_2O$: C, 65.52; H, 5.19; N, 11.76;

Found: C, 65.49; H, 5.18; N, 11.70.

Example 6

Preparation of 22,23-dihydro-5H,21H-6,10:12,16-dimetheno-24H-benzo[g]imidazo[4,3-m][1,8,11]oxadiazaeicosine-9-carbonitrile (6), hydrochloride salt

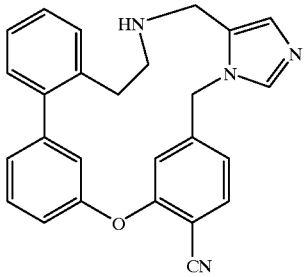

6

Step A: Preparation of 2-chloromethyl-3'-benzyloxybiphenyl

To a solution of (3'-benzyloxybiphenyl-2-yl)methanol from Example 4, Step E (247 mg, 0.851 mmol) in dry CH₂Cl₂ (5 mL) was added thionyl chloride (1.01 g, 8.51 mmol). The reaction mixture was stirred at ambient temperature for 2 hours, then concentrated to dryness in vacuo. The residue was concentrated twice from cyclohexane in vacuo to yield the titled compound.

Step B: Preparation of (3'-benzyloxybiphenyl-2-yl)acetonitrile

To a stirred solution of 2-chloromethyl-3'-benzyloxybiphenyl from Step A (188 mg, 0.61 mmol) in EtOH (4 mL) was added a solution of NaCN (60 mg, 1.22 mmol) in water (4 mL). The resulting solution was heated to reflux for 12 h, stood at ambient temperature for 48 h, then concentrated under reduced pressure. The residue was partitioned between sat. aq. NaHCO₃ (10 mL) and CH₂Cl₂ (20 mL). The aqueous layer was extracted further with CH₂Cl₂ (2×10 mL). The combined organic extracts were dried over Na₂SO₄, filtered, and concentrated under reduced pressure. The residue was purified by flash column chromatography, eluting with a gradient of 2–10% EtOAc in hexane to give the titled product.

Step C: Preparation of 1-amino-2-(3'-hydroxybiphenyl-2-yl)ethane hydrochloride A mixture of (3'-benzyloxybiphenyl-2-yl)acetonitrile from Step B (140 mg, 0.47 mmol), conc. HCl (0.060 mL, 0.73 mmol), and 10% Pd-C (30 mg) in MeOH (15 mL) was shaken under an atmosphere of hydrogen (ca. 50 atm) for 48 hours. The reaction mixture was filtered through a celite pad, washing with MeOH, and the filtrate was concentrated under reduced pressure to give the titled product, which was sufficiently pure for use in the next step.

Step D: Preparation of 2-fluoro-4-(5-{[2-(3'-hydroxybiphenyl-2-yl)ethylamino]methyl}imidazol-1-ylmethyl)benzonitrile 1-amino-2-(3'-hydroxybiphenyl-2-yl)ethane hydrochloride from Step C (0.47 mmol) and 1-(4-cyano-3-fluorobenzyl)-5-imidazolecarboxaldehyde from Example 3, Step G (112 mg, 0.49 mmol) were stirred in MeOH (1 mL) for 20 min, then NaCNBH₃ (38 mg, 0.60 mmol) was added. The reaction mixture was adjusted to pH 5 with AcOH, as judged from wetted pH paper, and stirring was continued at ambient temperature for 18 hours. The reaction was quenched with 10% aq. citric acid and stirred for 20 min. Sat. aq. NaHCO₃ (10 mL) was added and the mixture was extracted with CH₂Cl₂ (3×20 mL).

The combined organic extracts were dried over Na₂SO₄, filtered, and concentrated under reduced pressure. The residue was purified by flash column chromatography, eluting with a gradient of 1–5% MeOH/0.1–0.5% NH₄OH in CH₂Cl₂ to give the titled product.

Step E: Preparation of Compound 6 hydrochloride

A stirred mixture of 2-fluoro-4-(5-{[2-(3'-hydroxybiphenyl-2-yl)ethylamino]methyl}imidazol-1-ylmethyl)benzonitrile from Step D (76 mg, 0.178 mmol) and Cs₂CO₃ (87 mg, 0.267 mmol) in dry, degassed DMF (10 mL) under argon was heated to 50° C. for 18 hours, then concentrated in vacuo. The residue was partitioned between sat. aq. NaHCO₃ (10 mL) and CH₂Cl₂ (15 mL). The aqueous layer was extracted further with CH₂Cl₂ (2×10 mL). The combined organic extracts were dried over Na₂SO₄, filtered, and concentrated under reduced pressure. The residue was purified by flash column chromatography, eluting with a gradient of 1–5% EtOH/0.1–0.5% NH₄OH in CHCl₃ to give the desired product, which was treated with HCl in EtOAc to give the hydrochloride salt as a white powder.

FAB mass spectrum m/e 407.2 (M+1).

Analysis calculated for $C_{26}H_{22}N_4O \cdot 2 \, HCl \cdot 0.25 \, H_2O$: C, 64.53; H, 5.10; N, 11.58;

Found: C, 64.59; H, 4.98; N, 11.49.

Example 7

Preparation of 22,23-dihydro-5H,21H-6,10:12,16-dimetheno-23-methyl-24H-benzo[g]imidazo[4,3-m][1,8,11]oxadiazaeicosine-9-carbonitrile (7), hydrochloride

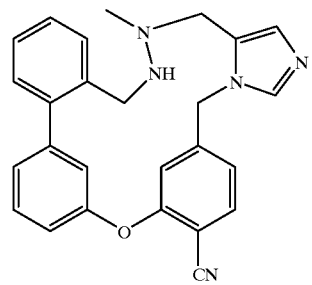

7

Step A: Preparation of Compound 7 hydrochloride

To a solution of Compound 6 hydrochloride from Example 6, Step E (40 mg, 0.083 mmol) in MeOH (1 mL) was added 1.0 N aqueous NaOH (0.167 mL, 0.167 mmol), then formaldehyde (0.025 mL of a 37 wt % solution in water, 0.31 mmol) was added and the reaction mixture was adjusted to pH 5 with AcOH, as judged from wetted pH paper. The mixture was stirred for 20 min at ambient temperature, then NaCNBH₃ (0.25 mL of a 1 M solution in THF, 0.25 mmol) was added, and stirring was continued at ambient temperature for 2 hours. The solvent was removed in vacuo, then sat. aq. NaHCO₃ (10 mL) was added and the mixture was extracted with CH₂Cl₂ (2×20 mL). The combined organic extracts were dried over $Na_2SO_4$, filtered, and concentrated under reduced pressure. The residue was purified by flash column chromatography, eluting with a gradient of 1–4% MeOH/0.1–0.4% $NH_4OH$ in $CH_2Cl_2$ to give the titled product, which was treated with HCl in EtOAc to give the hydrochloride salt as a white powder.

FAB mass spectrum m/e 421.2 (M+1).

Analysis calculated for $C_{27}H_{24}N_4O$.2 HCl.0.6 $H_2O$.0.25 EtOAc: C, 63.79; H, 5.60; N, 10.63;

Found: C, 63.79; H, 5.73; N, 10.62.

Example 8

Preparation of (±)-5-hydroxy-5-methyl-24-oxo-21,22,23,24-tetrahydro-5H-6,10:12,16-dimetheno-25H-benzo[o]imidazo[4,3-h][1,9,12]oxadiaza-cycloheneicosine-9-carbonitrile (8), hydrochloride

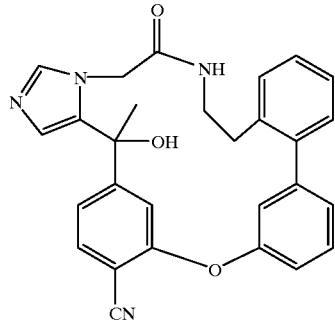

8

Step A: Preparation of 4-cyano-3-fluorotoluene

To a deoxygenated solution of 4-bromo-3-fluorotoluene (25.0 g, 132 mmol) in DMF (500 mL) was added $Zn(CN)_2$ (10.1 g, 86 mmol) and $Pd(PPh_3)_4$ (15 g, 13 mmol). The reaction was stirred at 100° C. for 18 hrs, then cooled to room temperature. The solution was poured into toluene (1 L), washed with 30% aq. $NH_4OH$ (2×1 L), then brine (800 mL), then dried ($Na_2SO_4$), filtered, and concentrated in vacuo to provide the crude product. Purification by silica gel chromatography, eluting with a gradient of hexane—0% to 7% EtOAc, yielded the titled product.

Step B: Preparation of α,α-dibromo-4-cyano-3-fluorotoluene

To a solution of 4-cyano-3-fluorotoluene from Step A (4.0 g, 29.6 mmol) in carbon tetrachloride (250 mL) was added N-bromosuccinimide (10.5 g, 59.2 mmol) and 2,2'-azobisisobutyronitrile (490 mg, 3.0 mmol). The reaction mixture was heated to reflux under argon for 24 hrs, then cooled to room temperature, filtered, and concentrated under reduced pressure. The residue was purified by silica gel chromatography, eluting with a gradient of hexane—3% to 7% EtOAc, to yield the titled product as a yellow-brown solid.

Step C: Preparation of 4-cyano-3-fluorobenzaldehyde

To a solution of α,α-dibromo-4-cyano-3-fluorotoluene, as described above in Step B, (5.60 g, 19.1 mmol) in EtOH (255 mL) and water (45 mL) was added $AgNO_3$. The mixture was heated to reflux for 3 hrs, then stood at ambient temperature for 18 hrs, then the solid was removed by filtration and the filtrate was concentrated under reduced pressure to a volume of approximately 20 mL. Water (30 mL) was added, and the mixture was concentrated to dryness in vacuo. The residue was partitioned between sat. aq. $NaHCO_3$ (20 mL) and $CH_2Cl_2$ (50 mL). The aqueous layer was extracted further with $CH_2Cl_2$ (2×50 mL). The combined organic extracts were dried over $Na_2SO_4$, filtered, and concentrated in vacuo. The residue was dried for several days at ca. 0.5 mm Hg to yield the desired aldehyde as a pale solid.

Step D: Preparation of (4-cyano-3-fluorophenyl)[1-(triphenylmethyl)imidazol-4-yl]methanol To a solution of 4-iodo-1-(triphenylmethyl)imidazole (2.93 g, 6.71 mmol) in dry $CH_2Cl_2$ (30 mL), under argon, was added MeMgBr (2.35 mL of a 3.0 M solution in $Et_2O$, 7.05 mmol), dropwise. The resulting solution was stirred at ambient temperature for 1 hr, then transferred dropwise into a stirred solution of 4-cyano-3-fluorobenzaldehyde from Step C (1.00 g, 6.71 mmol) in dry THF (30 mL), under argon, at −78° C. After 30 min, the reaction mixture was quenched with sat. aq. $NH_4Cl$ (50 mL) and extracted with $CH_2Cl_2$ (3×50 mL). The combined organic extracts were dried over $Na_2SO_4$, filtered, and concentrated in vacuo. The residue was triturated with EtOAc to yield the desired aldehyde as a white solid of sufficient purity for use in the next step.

Step E: Preparation of 4-cyano-3-fluorophenyl 1-(triphenylmethyl)imidazol-4-yl ketone To a solution of (4-cyano-3-fluorophenyl)[1-(triphenylmethyl)imidazol-4-yl]methanol from Step D (10.0 g, 21.8 mmol) in $CH_2Cl_2$ (300 mL) was added $MnO_2$ (18.9 g, 218 mmol) and the resulting mixture was heated to reflux for 18 hrs. The mixture was allowed to cool, then filtered through a pad of celite, washing with $CH_2Cl_2$. The filtrate was concentrated under reduced pressure to provide the titled product as a white solid that was sufficiently pure for use in the next step.

Step F: Preparation of 1-(4-cyano-3-fluorophenyl)-1-[1-(triphenylmethyl)imidazol-4-yl]ethanol To a solution of 4-cyano-3-fluorophenyl 1-(triphenylmethyl)imidazol-4-yl ketone from Step E (7.0 g, 15.3 mmol) in dry THF (280 mL), under argon, at −78° C., was added MeMgBr (5.3 mL of a 3.0 M solution in $Et_2O$, 15.9 mmol), dropwise. After 1 hr, the reaction mixture was quenched with sat. aq. $NH_4Cl$ (100 mL) and extracted with $CH_2Cl_2$ (2×150 mL). The combined organic extracts were dried over $MgSO_4$, filtered, and concentrated in vacuo. The residue was purified by silica gel chromatography, eluting with a gradient of hexane—30% to 50% EtOAc, to yield the titled product as pale solid.

Step G: Preparation of {5-[1-(4-cyano-3-fluorophenyl)-1-hydroxyethyl]imidazol-1-yl}acetic acid methyl ester To a stirred solution of 1-(4-cyano-3-fluorophenyl)-1-[1-(triphenylmethyl)imidazol-4-yl]ethanol from Step F (200 mg, 0.42 mmol), methyl glycolate (35 mg, 0.39 mmol), and N,N-diisopropylethylamine (65 mg, 0.51 mmol) in dry $CH_2Cl_2$ (10 mL), under argon, at −78° C., was added trifluoromethanesulfonic anhydride (110 mg, 0.39 mmol) dropwise. The mixture was allowed to warm slowly to ambient temperature, then the solvent was removed in vacuo. The residue was dissolved in MeOH (10 mL) and the solution was heated to reflux for 1 hr, then concentrated to dryness. The residue was purified by silica gel chromatography, eluting with 4% MeOH—0.4% $NH_4OH$ in $CHCl_3$, to yield the titled product as a white solid.

Step H: Preparation of {5-[1-(4-cyano-3-fluorophenyl)-1-hydroxyethyl]imidazol-1-yl}acetic acid, lithium salt A mixture of {5-[1-(4-cyano-3-fluorophenyl)-1-hydroxyethyl]imidazol-1-yl}acetic acid methyl ester from Step G (50 mg, 0.165 mmol) and LiOH (7.3 mg, 0.174 mmol) was stirred in THF (1.7 mL) and $H_2O$ (0.3 mL) at ambient temperature for 2 hrs. The solution was adjusted to pH≈7 by the addition of 1.0 N aq. HCl and then concentrated in vacuo to give the desired product.

Step I: Preparation of 2-{5-[1-(4-cyano-3-fluorophenyl)-1-hydroxyethyl]imidazol-1-yl}-N-[2-(3'-hydroxybiphenyl-2-yl)ethyl]acetamide A solution of {5-[1-(4-cyano-3-fluorophenyl)-1-hydroxyethyl]imidazol-1-yl}acetic acid, lithium salt from Step H (40 mg, 0.145 mmol), 1-amino-2-(3'-hydroxybiphenyl-2-yl)ethane from Example 6, Step C (33 mg, 0.155 mmol), 1-hydroxybenzotriazole hydrate (23 mg, 0.17 mmol), EDC (33 mg, 0.17 mmol), and N,N-diisopropylethylamine (40 mg, 0.31 mmol) in dry, degassed DMF (1 mL) was stirred at ambient temperature for 18 hrs. The solvent was removed under reduced pressure and the residue was partitioned between sat. aq. $NaHCO_3$ (1 mL) and $CHCl_3$ (3 mL). The aqueous layer was extracted further with $CHCl_3$ (2×2 mL). The combined organic extracts were dried over $Na_2SO_4$, filtered, and concentrated under reduced pressure. The crude product was purified by preparative thin layer chromatography, eluting with 6% MeOH/0.6% $NH_4OH$ in $CH_2Cl_2$ to give the titled product as a white solid.

Step J: Preparation of Compound 8 hydrochloride

A stirred mixture of 2-{5-[1-(4-cyano-3-fluorophenyl)-1-hydroxyethyl]imidazol-1-yl}-N-[2-(3'-hydroxybiphenyl-2-yl)ethyl]acetamide from Step I (13 mg, 0.027 mmol) and $Cs_2CO_3$ (13 mg, 0.040 mmol) in dry, degassed DMF (2 mL) under argon was heated to 50° C. for 18 hours. After addition of more $Cs_2CO_3$ (5 mg, 0.015 mmol), the mixture was heated to 60° C. for 4 hrs. The solvent was removed under reduced pressure and the residue was purified by flash column chromatography, eluting with 5% MeOH/0.5% $NH_4OH$ in $CH_2Cl_2$ to give the desired product, which was treated with HCl in acetonitrile—water and lyophilized to give the titled compound as a white solid.

FAB mass spectrum m/e 465 (M+1).

Analysis calculated for $C_{28}H_{24}N_4O_3 \cdot HCl \cdot 1.2 \ H_2O \cdot 1.1 \ CH_2Cl_2$: C, 60.64; H, 4.99; N, 9.74;

Found: C, 60.64; H, 5.01; N, 9.88.

Example 9

Preparation of 17-Oxo-17,18,23,24-tetrahydro-5H-6,10:12,16-dimetheno-25H, 26H-benzo[n]imidazo[3,4-h][1,8,12,16]oxatriaza-cyclodocosine-9-carbonitrile (9)

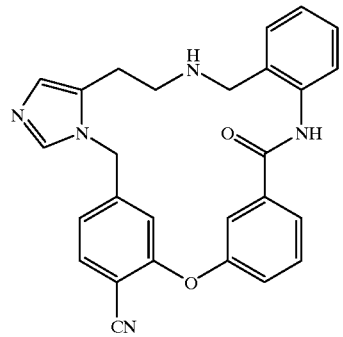

Step A: Preparation of 4-bromo-3-fluorobenzoic acid

4-Bromo-3-fluorotoluene(40.0 g, 0.212 mol) was heated at 90° C. in $H_2O$ (200 mL) and pyridine (200 mL) with mechanical stirring under Ar. Potassium permanganate ($KMnO_4$) (67 g, 0.424 mol) was added portionwise over 3 h. After 4 h, an HPLC of a filtered sample indicated 50% conversion to the acid. An additional 30 g of $KMnO_4$ was added and heating continued overnight. HPLC indicated 81% conversion. Further $KMnO_4$ was added portionwise with reaction monitoring by HPLC until >95% conversion was obtained. The reaction mixture was filtered through Celite, the filter pad washed with $H_2O$, aq NaOH and EtOH. The filtrate was concentrated to a small volume, then partitioned between 3N NaOH solution and diethyl ether. The aqueous basic layer was separated, cooled in an ice-$H_2O$ bath and acidified slowly with 6N HCl solution to precipitate the white solid product. This was collected by suction filtration and dried at 40° C. in a vacuum oven overnight to give the title compound. mp 190–192° C.

1H NMR (CDCl3) d 7.83 (dd, 1H, J=2, 9 Hz), 7.78 (dd, 1H, J=2, 8 Hz), 7.67–7.71 (m, 1H).

Step B: Preparation of 4-bromo-3-fluorobenzyl alcohol

4-Bromo-3-fluorobenzoic acid (40.8 g, 0.187 mol) was dissolved in THF (250 ml) with magnetic stirring under Ar in an ice-$H_2O$ bath. The cloudy solution was treated dropwise with borane-THF complex (1 M) (374 mL, 0.374 mol) over a 1 h period maintaining the internal temperature at <10° C. The reaction mixture was left to warm to ambient temperature overnight, then cooled in an ice $H_2O$ bath and treated dropwise with $H_2O$ (150 mL). The THF was removed on a rotary evaporator, and the residue partitioned between EtOAc and $H_2O$. The aqueous layer was extracted with EtOAc (3×100 mL), the organic layers combined, washed with brine, and dried ($Na_2SO_4$), filtered, and concentrated to give the title compound as an oil which solidified on standing.

$^1$H NMR (CDCl3) d 7.52 (t, 1H, J=8 Hz), 7.16 (d, 1H, J=9 Hz), 7.02 (d, 1H, J=8 Hz), 4.67 (s, 2H), 1.47 ( br s, 1H).

Step C: Preparation of 2-fluoro-4-hydroxymethylbenzonitrile

4-Bromo-3-fluorobenzyl alcohol( 20 g, 0.097 mol) was dissolved in DMF (100 mL) and then placed under high vacuum for 15 min. The solution was then purged with Ar for 15 min. While purging continued, zinc cyanide ( 8 g, 0.068 mol) and the catalyst, Pd[(PPh$_3$)]4, (5.63 g, 0.0049 mol) were added. The reaction mixture was heated at 95° C. under Ar for 18 h, then cooled to ambient temperature and added to H$_2$O. The mixture was extracted with EtOAc, then washed with 1 M HCl, H$_2$O, brine, and dried (Na$_2$SO$_4$). Filtration and concentration to dryness gave the title compound as a white solid after chromatography (silica gel, hexane: EtOAc, 6.5:3.5).

$^1$H NMR (CDCl$_3$) d 7.61 (t, 1H, J=8 Hz), 7.23–7.29 (m, 2H), 4.80 (d, 2H, J=6 Hz), 1.93 (t, 1H, J=6 Hz).

Step D: Preparation of 4-bromomethyl-2-fluoro-benzonitrile

N-Bromosuccinimide (6.6 g, 0.037 mol) was dissolved in CH$_2$Cl$_2$ (150 mL), cooled to 0° C. and treated with dimethylsulfide (3.27 mL, 0.0446 mol). The solution was cooled to −20° C. and then treated dropwise with a solution of 2-fluoro-4-hydroxymethylbenzonitrile (3.74 g, 0.0248 mol) in CH$_2$Cl$_2$ (30 mL). After the addition, the reaction mixture was stirred at 0° C. for 2 h then left to warm to ambient temperature overnight. The reaction mixture was added to ice/H$_2$O, extracted with EtOAc, the organic layer separated, washed with brine and dried (MgSO$_4$). Filtration and concentration to dryness gave the title compound which was purified by chromatography (silica gel, 5–10% EtOAc/hexane.

$^1$H NMR (CDCl3) d 7.61 (dd, 1H, J=8, 8 Hz), 7.26–7.30 (m, 2H), 4.45 (s, 2H).

Step E: Preparation of {2-[3-(4-cyano-3-fluoro-benzyl)-3H-imidazol-4-yl]-ethyl}-carbamic acid tert-butyl ester To a solution of N$^T$-pivaloyloxymethyl-N$^\alpha$-phthaloyl-histamine (J. C. Emmett, F. H. Holloway, and J. L. Turner, *J. Chem. Soc., Perkin Trans.* 1, 1341, (1979)) ( 4.59 g, 0.0124 mol) in acetonitrile (40 mL) was added 4-bromomethyl-2-fluorobenzonitrile (2.8 g, 0.013 mol) and the mixture was heated to reflux for 18 hr. A white solid precipitate formed, which after cooling to 0° C., was collected by filtration to obtain the quaternary salt. This intermediate was dissolved in EtOH (100 mL), hydrazine (1.46 mL, 0.046 mol) was added, and the mixture was heated at reflux for 4 hr. A white precipitate was observed and the reaction was cooled to 25° C. Dimethylphthalate (11.4 mL, 0.0699 mol) was added and the mixture was again refluxed for 18 hr. After cooling to 25° C. the precipitate was removed by filtration and washed with EtOAc. The filtrate was evaporated in vacuo and the residue was dissolved in THF (125 mL) and H$_2$O (25 mL). To this solution was added solid Na$_2$CO$_3$ (4.0 g, 0.0377 mol) and BOC$_2$O (4.47 g, 0.020 mol) and the reaction was stirred for 18 hr. The THF was removed in vacuo and the mixture was partitioned with EtOAc and saturated NaHCO$_3$. The EtOAc layer was washed with brine, dried with MgSO$_4$, and evaporated in vacuo to obtain the title product after chromatography (silica gel, CH$_2$Cl$_2$:MeOH:NH$_4$OH/97:3:0.3.

Step F: Preparation of 4-[5-(2-amino-ethyl)-imidazol-1-ylmethyl]-2-fluoro-benzonitrile dihydrochloride A solution of {2-[3-(4-cyano-3-fluoro-benzyl)-3H-imidazol-4-yl]-ethyl}-carbamic acid tert-butyl ester (1.0 g, 0.0029 mol) in EtOAc (30 mL) was cooled to −20° C. and saturated with HCl gas. The cooling bath was removed and the reaction was stirred for 2 h. The solvent was removed in vacuo to obtain the title compound which was used without further purification.

Step G: Preparation of N-(2-methoxycarbonylphenyl)-3-phenylmethoxybenzyl amide To a solution of 3-phenylmethoxybenzoyl chloride (11.1 g, 45.1 mmol) in CHCl$_3$ (125 mL) at 0° C. was added NEt$_3$ (12.5 mL, 90.3 mmol) and methyl 2-aminobenzoate (5.26 mL, 40.6 mmol) and the mixture was stirred for 1 h. The solvents were removed in vacuo and the resulting solid residue was triturated with hexane/EtOAc (85/15) to obtain the title compound which was used without further purification.

Step H: Preparation of N-(2-hydroxymethylphenyl)-3-phenylmethoxybenzyl amide To a solution of N-(2-methoxycarbonylphenyl)-3-phenylmethoxybenzyl amide (15.9 g, 44.0 mmol) in THF (300 mL) at 0° C. was added LiBH$_4$ (2.0 M in THF, 33.0 mL, 66.0 mmol). The cooling bath was removed and stirring was continued for 216 h. The reaction was quenched with MeOH (100 mL) and stirred for 2 h. The solvents were removed in vacuo, and the residue was partitioned between EtOAc and saturated NaHCO$_3$. The organic layer was separated, washed with 10% HCl, H$_2$O, brine, and dried (MgSO$_4$). Filtration and concentration in vacuo gave the title compound which was used without further purification.

Step I: Preparation of N-(2-hydroxymethylphenyl)-3-hydroxybenzyl amide

To a solution of N-(2-hydroxymethylphenyl)-3-phenylmethoxybenzyl amide (10.0 g, 41.1 mmol) in EtOH (100 mL) was added 10% Pd/C (1.5 g) and the mixture was placed in a Paar apparatus under 50 psi H$_2$ and shaken for 18 h. The mixture was filtered and the solvents were removed in vacuo to obtain the title compound which was used without further purification.

Step J: Preparation of N-(2-formyl-phenyl)-3-hydroxy-benzamide

To a solution of N-(2-hydroxymethylphenyl)-3-hydroxybenzyl amide (6.5 g, 26.7 mmol) in CH$_2$Cl$_2$ (120 ml) at 0° C. was added NEt$_3$ (13.0 ml, 93.4 mmol) and pyridine.SO$_3$ complex (12.7 g, 80.1 mmol ) in DMSO, 50 mL) and the solution was stirred 4 h at 25° C. The reaction was poured into ice and 10% HCl, and the layers were partitioned. The aqueous layer was washed 2× with CH$_2$Cl$_2$. All CH$_2$Cl$_2$ layers were combined and washed with H$_2$O, saturated NaHCO$_3$, brine, and dried (MgSO$_4$). The solution was filtered and concentrated in vacuo to obtain the crude product which was purified on SiO$_2$ gel using hexane/EtOAc 7/3 to obtain the title compound.

Step K: Preparation of N-[2-({2-[3-(4-cyano-3-fluoro-benzyl)-3H-imidazol-4-yl]-ethylamino}-methyl)-phenyl]-3-hydroxy-benzamide To a solution of 4-[5-(2-amino-ethyl)-imidazol-1-ylmethyl]-2-fluoro-benzonitrile dihydrochloride (Step F) (0.64 g, 2.03 mmol) in MeOH (15 mL) was added NEt$_3$ dropwise to pH=4.5. To this solution was added N-(2-formyl-phenyl)-3-hydroxy-benzamide (0.64 g, 2.64 mmol) and NaCNBH$_3$ (0.255 g, 4.06 mmol), and the reaction was stirred 18 h at 25° C. The MeOH was removed in vacuo, and the residue was partitioned with EtOAc and saturated NaHCO$_3$. The organic layer was separated and washed 3× with 10% HCl. The acidic layers were combined, made basic with Na$_2$CO$_3$, then extracted 3× with EtOAc. These layers were combined, washed with brine and dried (MgSO$_4$). Filtration and concentration in vacuo gave the crude product which was purified by prep HPLC to obtain the title compound.

Step L: Preparation of compound 9

To a solution of N-[2-({2-[3-(4-cyano-3-fluoro-benzyl)-3H-imidazol-4-yl]-ethylamino}-methyl)-phenyl]-3-hydroxy-benzamide (0.18 g, 0.405 mmol) in DMSO (8 mL) was added $Cs_2CO_3$ (0.53 g, 1.62 mmol) and the reaction was stirred for 6 h at 25° C. The reaction was partitioned with EtOAc and saturated $NaHCO_3$. The aqueous layer was washed with EtOAc, the organics combined, washed with brine, and dried ($MgSO_4$). Filtration and concentration in vacuo gave the crude product which was purified on prep HPLC to obtain the title compound.

FAB mass spectrum m/e 450 (M+1).

Analysis calculated for $C_{27}H_{23}N_5O_2 \cdot 0.5\ H_2O$: C, 70.72; H, 5.28; N, 15.28;

Found: C, 70.73; H, 5.23; N, 15.12.

Example 10

Preparation of 3-Methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (10)

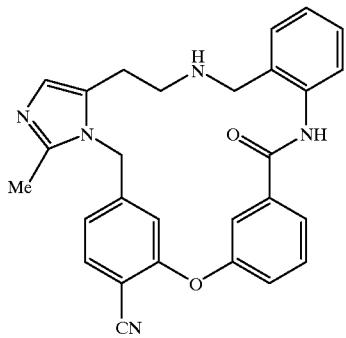

10

Step A: Preparation of 4-[5-(2-amino-ethyl)-2-(methyl)-imidazol-1-ylmethyl]-2-fluoro-benzonitrile dihydrochloride Using the procedures described in Example 9, Steps A–F, but substituting $N^T$-pivaloyloxymethyl-$N^{\alpha}$-phthaloyl-2-methyl-histamine in place of $N^T$-pivaloyloxymethyl-$N^{\alpha}$-phthaloyl-histamine in Step E, the title compound was prepared.

Step B: Preparation compound 10

Using the procedures described in Example 9, Steps K and L, but substituting 4-[5-(2-amino-ethyl)-2-(methyl)-imidazol-1-ylmethyl]-2-fluoro-benzonitrile dihydrochloride (2.0 g, 6.04 mmol) in place of 4-[5-(2-amino-ethyl)-imidazol-1-ylmethyl]-2-fluoro-benzonitrile dihydrochloride in step K the title compound was prepared.

FAB mass spectrum m/e 464 (M+1).

Analysis calculated for $C_{28}H_{25}N_5O_2 \cdot 0.3\ EtOAc$: C, 71.57; H, 5.64; N, 14.29;

Found: C, 71.64; H, 5.42; N, 14.08.

Example 11

Preparation of 24-tert-Butoxycarbonyl-3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (11)

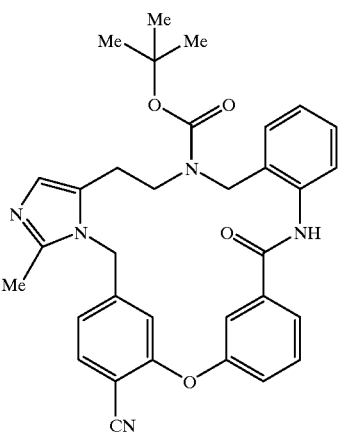

11

To a solution of 3-Methyl-17-oxo-17,18,23,24-tetrahydro-5H-6,10:12,16-dimetheno-25H, 26H-benzo[n]imidazo[3,4-h][1,8,12,16]-oxatriazacyclodocosine-9-carbonitrile (Example 10) (0.3 g, 0.647 mmol) in $CH_2Cl_2$ (20 mL) was added $NEt_3$ (0.18 mL, 1.29 mmol) and di-tert-butyl dicarbonate (0.28 g, 1.29 mmol). After stirring for 42 h the solution was partitioned between $CH_2Cl_2$ and saturated $NaHCO_3$ solution. The organic layer was separated, washed with $H_2O$, brine, and dried ($MgSO_4$). Filtration and concentration in vacuo gave the title compound which was used without further purification.

Example 12

Preparation of 24-tert-Butoxycarbonyl-18-ethyl-3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (12)

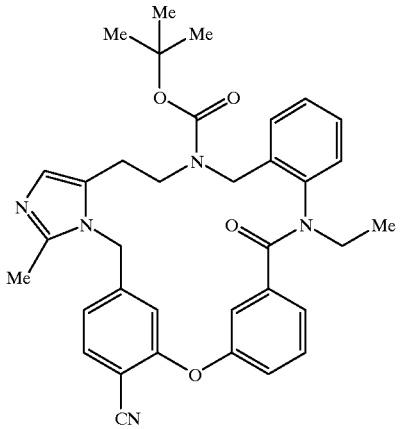

12

To a solution of 24-tert-Butoxycarbonyl-3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (0.2 g, 0.356 mmol)

in DMF (8.0 mL) at 0° C. was added NaH (0.028 g, 0.712 mmol) and the mixture was stirred for 20 min. To this was added ethyl iodide (0.056 mL, 0.70 mmol) and the reaction was stirred for 20 hr at 25° C. The DMF was removed in vacuo, and the residue was partitioned between EtOAc and saturated NaHCO$_3$ solution. The organic layer was separated, washed with H$_2$O, brine, and dried (MgSO$_4$). Filtration and concentration in vacuo gave the title compound which was used without further purification.

Example 13

Preparation of 18-Ethyl-3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (13)

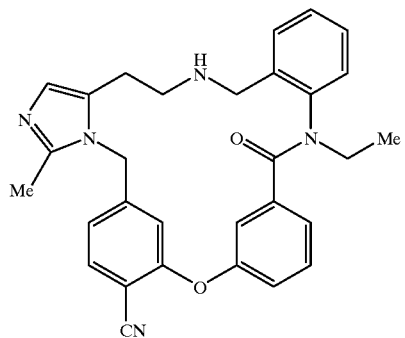

A solution of of 24-tert-butoxycarbonyl-18-ethyl-3-methyl-17-oxo-17,18,23,24-tetrahydro-5H-6,10:12,16-dimetheno-25H, 26H-benzo[n]imidazo[3,4-h][1,8,12,16] oxatriazacyclodocosine-9-carbonitrile (0.31 g) in TFA/CH$_2$Cl$_2$ 3/1 (8 mL) was stirred for 45 min. The solvents were removed in vacuo and the residue was purified by prep HPLC to obtain the title compound.

FAB mass spectrum m/e 492 (M+1)

Example 14

Preparation of of 24-Acetyl-3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (14)

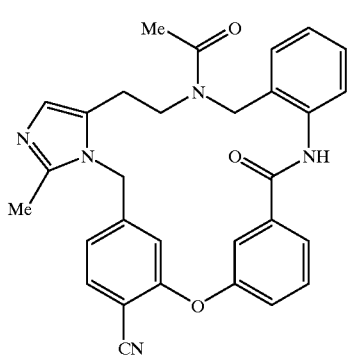

To a solution of of 3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (Example 10) (0.036 g, 0.078 mmol) in CH$_2$Cl$_2$ (3.0 mL) was added NEt$_3$ (0.032 mL) and acetyl chloride (0.0072 mL). After 2 h the reaction was partitioned between EtOAc and saturated NaHCO$_3$ solution. The organic layer was separated, washed with brine and dried (MgSO$_4$). Filtration and concentration in vacuo gave the title compound.

FAB mass spectrum m/e 506 (M+1).

Analysis calculated for C$_{30}$H$_{27}$N$_5$O$_3$.0.55 H$_2$O: C, 69.89; H, 5.49; N, 13.59;

Found: C, 70.11; H, 5.44; N, 13.19.

Example 15

Preparation of of 3-methyl-24-methylsulfonylethyl-17-oxo-17,18,23,24-tetrahydro-5H-6,10:12,16-dimetheno-25H, 26H-benzo[n]imidazo[3,4-h][1,8,12,16]oxatriazacyclodocosine -9-carbonitrile (15)

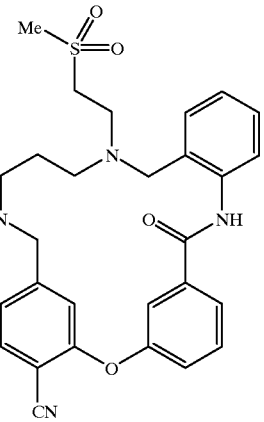

To a solution of 3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (Example 10) (0.04 g, 0.087 mmol) in CH$_3$CN (5.0 mL) was added NEt$_3$ (0.050 mL) and methyl vinylsulfone (0.023 mL, 0.261 mmol). The reaction was refluxed for 72 h, the solvents removed in vacuo, and the residue purified on prep HPLC to obtain the title compound.

FAB mass spectrum m/e 570 (M+1).

Example 16

Preparation of 3,24-Dimethyl-17-oxo-17,18,23,24-tetrahydro-5H-6,10:12,16-dimetheno-25H, 26H-benzo[n]imidazo[3,4-h][1,8,12,16] oxatriazacyclodocosine-9-carbonitrile (16)

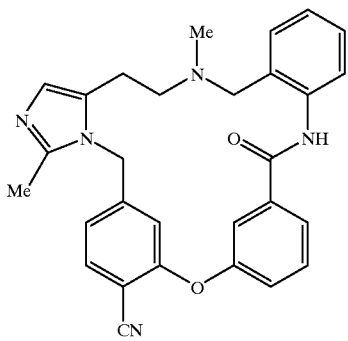

To a solution of 3-methyl-17-oxo-17,18,23,24-tetrahydro-5H-6,10:12,16-dimetheno-25H, 26H-benzo[n]imidazo[3,4-h][1,8,12,16]oxatriazacyclodocosine-9-carbonitrile (0.036 g, 0.078 mmol) in MeOH (5.0 mL) at pH=4–5 was added paraformaldehyde (0.020 g) and NaCNBH$_3$ (0.010 g). After stirring for 2 h the MeOH was removed in vacuo and the residue was partitioned between EtOAc and saturated NaHCO$_3$ solution. The organic layer was separated, washed with brine, and dried (MgSO$_4$). Filtration and concentration in vacuo gave the title compound.

FAB mass spectrum m/e 478 (M+1).

Example 17

Preparation of 17,18-Dihydro-15-iodo-3-methyl-17-oxo-5H-6,10:12,16-dimetheno-19H,20H-imidazo[3,4-h][1,8,12]oxadiazacyclooctadecine-9-carbonitrile (17)

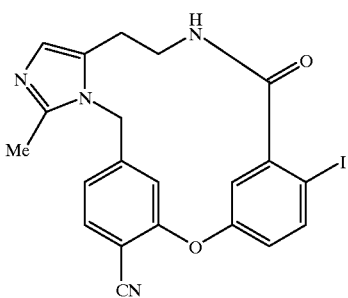

Step A: Preparation of 5-Hydroxy-2-iodobenzoic acid

The titled compound was prepared as in Robert A. Moss, K. W. Alwis, and Jae-Sup Shin, *J. Am. Chem. Soc.* 1984, 106, 2651–2655.

Step B: Preparation of N-{2-[3-(4-Cyano-3-fluoro-benzyl)-2-methyl-3H-imidazol-4-yl]-ethyl}-5-hydroxy-2-iodobenzamide A stirred mixture of 4-[5-(2-amino-ethyl)-2-(methyl)-imidazol-1-ylmethyl]-2-fluoro-benzonitrile dihydrochloride as prepared in Example 10, Step A (2.00 g, 6.038 mmol), 5-hydroxy-2-iodobenzoic acid (1.594 g, 6.038 mmol), 1-Hydroxybenzotriazole hydrate (816 mg, 6.038 mmol), and triethylamine (2.52 mL, 18.114 mmol) in dry DMF (12.0 mL) was cooled to 0° C., and EDC (1.158 g, 6.038 mmol) was added. After stirring at 0° C. for 15 minutes, the reaction mixture was stirred at ambient temperature overnight, then poured into water and extracted with EtOAc. The organic layer was dried (MgSO$_4$), filtered, and concentrated under reduced pressure. The residue was preabsorbed onto silica gel and purified by flash chromatography eluting with a gradient of 6–9% MeOH/CH$_2$Cl$_2$ to give the titled product.

$^1$H NMR: CD$_3$OD (δ, 400 MHz) 7.73 (1H,dd, J=6.8 and 7.9 Hz), 7.59(1H, d, J=8.6 Hz), 7.01(1H, d, J=9.9 Hz), 6.95(1H, d, J=8.0 Hz), 6.85(1H, s), 6.71(1H, d, J=2.9 Hz), 6.61(1H, dd, J=2.9 and 8.6 Hz), 5.37(2H, s), 3.47(2H, t, J=7.2 Hz), 2.78(2H, d, J=7.2 Hz), and 2.28(3H, s) ppm.

Step C: Preparation of compound 17

A flask containing cesium carbonate (3.23 g, 9.915 mmol) was purged with argon, DMF (40 mL) was added and the slurry was warmed to 60° C. with stirring. A solution of N-{2-[3-(4-cyano-3-fluoro-benzyl)-2-methyl-3H-imidazol-4-yl]-ethyl}-5-hydroxy-2-iodobenzamide from Step B (2.00 g, 3.966 mmol) in DMF (45 mL) was added via syringe pump over 8 hours. The reaction was heated for an additional hour and then allowed to cool to ambient temperature. The crude reaction was poured into water and extracted with EtOAc. The combined organic extracts were washed with water and brine, dried (MgSO$_4$), filtered, and concentrated under reduced pressure. The residue was purified by flash column chromatography eluting with 7% MeOH/CH$_2$Cl$_2$ to give the desired product as a white solid.

$^1$H NMR: CD$_3$OD(δ, 400 MHz) 7.96 (1H,d, J=8.6 Hz), 7.80(1H, d, J=8.1 Hz), 7.32(1H, d, J=8.1 Hz), 7.08(1H, dd, J=2.9 and 8.6 Hz), 7.03(1H,d, J=2.9 Hz), 6.50(1H, s), 6.13(1H, s), 5.50–5.00(2H, brs), 4.00–2.40(4H, m) and 2.21(3H, s) ppm.

FAB mass spectrum m/e 485.05 (M+1).

Example 18

Preparation of 17,18-Dihydro-3-methyl-17-oxo-15-phenyl-5H-6,10:12,16-dimetheno-19H,20H-imidazo[3,4-h][1,8,12]oxadiazacyclooctadecine-9-carbonitrile (18) trifluoroacetate salt

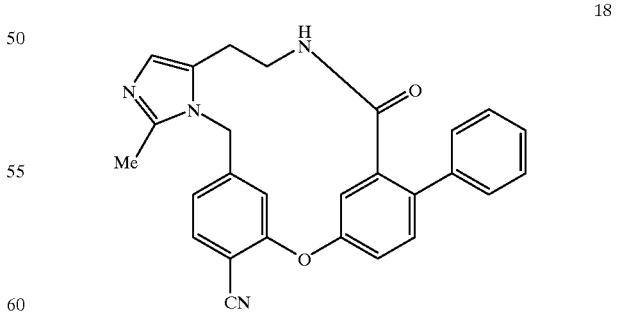

To a degassed solution of the iodide from Example 17, Step C (75 mg, 0.155 mmol) in dioxane (550 μL) was added tribasic potassium phosphate (65.8 mg, 0.310 mmol), phenylboronic acid (28.4 mg, 0.233 mmol), triphenylphosphine (2.4 mg, 0.0093 mmol), and palladium (II) acetate (1.1 mg, 0.0047 mmol). The reaction was heated at 90° C. overnight. Additional triphenylphosphine (4.8 mg, 0.0186 mmol) and palladium(II) acetate (2.2 mg, 0.0094 mmol) was added and heating continued overnight. Additional triphenylphosphine (4.8 mg, 0.0186 mmol) and palladium(II) acetate (2.2 mg, 0.0.0094 mmol) was added and heated overnight again. The crude reaction mixture was poured into EtOAc (25 mL) and washed with NaHCO$_3$ (40 mL). The combined organics were washed with brine, dried (MgSO$_4$), filtered, and concentrated under reduced pressure. The residue was purified by prep HPLC (5–95% acetonitrile/water+0.1% TFA gradient elution on C-18 column). Product fractions were lyophilized to give the desired product as a white solid.

$^1$H NMR: CD$_3$OD (δ, 300 MHz) 7.88 (1H,d, J=8.1 Hz), 7.57(1H, d, J=8.6 Hz), 7.54–7.32(7H,m), 7.26(1H, s), 7.09 (1H, d, J=2.4Hz), 6.43(1H, s), 5.70–5.30(2H, brs), 4.00–2.40(4H, m) and 2.53(3H, s) ppm.

FAB mass spectrum m/e 435.18 (M+1).

Analysis calculated for C$_{27}$H$_{22}$N$_4$O$_2$.1.20 TFA.1.90 H$_2$O: C, 58.31; H, 4.49; N, 9.25;

Found: C, 58.32; H, 4.50; N, 8.87.

Example 19

Preparation of trans-15-[2-(3-Chlorophenyl) ethenyl]-17,18-dihydro-3-methyl-17-oxo-5H-6, 10:12,16-dimetheno-19H,20H-imidazo[3,4-h][1,8, 12]oxadiazacyclooctadecine-9-carbonitrile (19) trifluoroacetate salt

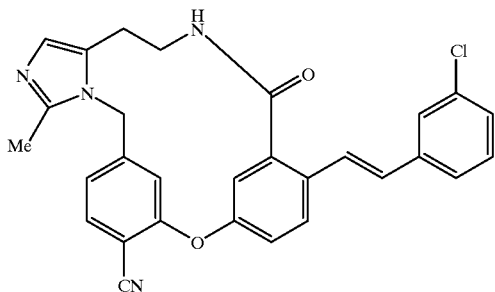

To a stirring mixture of the iodide from Example 17, Step C (75 mg, 0.155 mmol), tri-o-tolylphosphine (18.9 mg, 0.062 mmol), and palladium(II) acetate (7.0 mg, 0.031 mmol) in DMF (600 μL) under argon was added triethylamine (108 μL, 0.775 mmol) followed by 3-chlorostyrene (59.1 μL, 0.465 mmol). The reaction was degassed 3 times and then heated at 100° C. overnight. The reaction was cooled to ambient temperature and poured into NaHCO$_3$ and extracted with CH$_2$Cl$_2$. The combined organic extracts were dried (MgSO$_4$), filtered, and concentrated under reduced pressure. The residue was purified by prep HPLC (5–95% acetonitrile/water+0.1% TFA gradient elution on C-18 column). The product fractions were lyophilized to give the titled product as a white solid.

$^1$H NMR: CD$_3$OD (δ, 300 MHz) 7.98 (1H,d, J=8.8 Hz), 7.88(1H, d, J=8.1 Hz), 7.55(1H,brt, J=0.5 Hz), 7.50–7.10 (8H,m), 7.04(1H, d, J=2.7 Hz), 6.47(1H, s), 5.52(2H, brs), 4.00–2.40(4H, m) and 2.52(3H, s) ppm.

FAB mass spectrum m/e 495.16 (M+1).

Analysis calculated for C$_{29}$H$_{23}$N$_4$O$_2$Cl.1.40 TFA.1.60 H$_2$O: C, 55.88; H, 4.07; N, 8.20;

Found: C, 55.87; H, 4.05; N, 8.10.

Example 20

Preparation of 18-Benzyl-17,18-dihydro-15-iodo-3-methyl-17-oxo-5H-6,10:12,16-dimetheno-19H,20H-imidazo[3,4-h][1,8,12]oxadiazacyclooctadecine-9-carbonitrile (20)

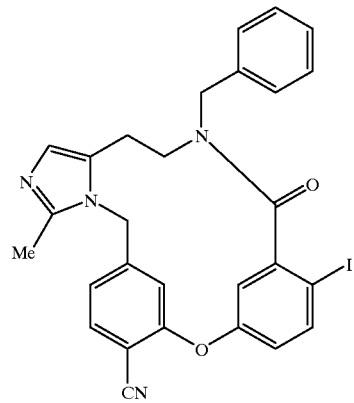

Sodium hydride (60% dispersion in mineral oil) (5.92 mg, 0.148 mmol) was washed with hexanes under argon. DMF (600 μL) was added and the mixture was cooled to 0° C. with stirring. A solution of the iodide from Example 17, Step C (55 mg, 0.114 mmol) in DMF (800 μL) was added. After 10 minutes, benzyl bromide (13.6 μL, 0.114 mmol) was added and the reaction was stirred at 0° C. for 15 minutes before allowing the reaction to stir at ambient temperature overnight. The reaction was quenched with NH$_4$Cl aq. and partitioned between water and EtOAc. The combined organic extracts were dried (MgSO$_4$), filtered, and concentrated under reduced pressure. The residue was purified by flash chromatography eluting with a gradient of 4–5% MeOH/CH$_2$Cl$_2$ to give the titled product.

$^1$H NMR: CDCl$_3$ (δ, 300 MHz) 7.86 (1H,d, J=8.6 Hz), 7.71(1H, d, J=8.1 Hz), 7.50–7.19(5H, m), 7.13(1H, d, J=8.6 Hz), 6.98(1H,dd, J=8.6 and 2.7 Hz), 6.71(1H, d, J=2.7 Hz), 6.43(1H, s), 6.14(1H,s), 5.41(1H,d, J=14 Hz), 5.13(1H, d, J=18 Hz), 4.83(1H,d, J=18 Hz). 4.13(1H, d, J=14 Hz) 3.65–3.40(1H,m), 3.30–2.90(2H,m), 2.24(3H,s), and 2.18–2.00 (1H,m) ppm.

FAB mass spectrum m/e 575.09 (M+1).

Analysis calculated for C$_{28}$H$_{23}$N$_4$O$_2$I.0.05 CH$_2$Cl$_2$.0.95 H$_2$O: C, 56.54; H, 4.23; N, 9.40;

Found: C, 56.54; H, 4.21; N, 9.25.

Example 21

In vitro Inhibition of Ras Farnesyl Transferase

Transferase Assays. Isoprenyl-protein transferase activity assays are carried out at 30° C. unless noted otherwise. A typical reaction contains (in a final volume of 50 μL): [$^3$H]farnesyl diphosphate, Ras protein, 50 mM HEPES, pH 7.5, 5 mM MgCl$_2$, 5 mM dithiothreitol, 10 μM ZnCl$_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) Biochemistry 32:5167–5176. After thermally pre-equilibrating the assay mixture in the absence of enzyme, reactions are initiated by the addition of isoprenyl-protein transferase and stopped at timed intervals (typically 15 min)

by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor $IC_{50}$ determinations are as follows: FTase, 650 nM Ras-CVLS (SEQ.ID.NO.: 1), 100 nM farnesyl diphosphate.

The compounds of the instant invention are tested for inhibitory activity against human FPTase by the assay described above.

The compounds of the instant invention described in the above Examples 1–20 were tested for inhibitory activity against human FPTase by the assay described above and were found to have $IC_{50}$ of <50 µM.

Example 22
Modified in vitro GGTase Inhibition Assay

The modified geranylgeranyl-protein transferase inhibition assay is carried out at room temperature. A typical reaction contains (in a final volume of 50 µL): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 µM $ZnCl_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 2). Reactions are initiated by the addition of GGTase and stopped at timed intervals (typically 15 min) by the addition of 200 µL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and substrate concentrations for inhibitor $IC_{50}$ determinations are as follows: 75 pM GGTase-I, 1.6 µM Ras peptide, 100 nM geranylgeranyl diphosphate.

The compounds of the instant invention are tested for inhibitory activity against human GGTase-type I by the assay described above.

Example 23
Cell-based in vitro Ras Farnesylation Assay

The cell line used in this assay is a v-ras line derived from either Rat1 or NIH3T3 cells, which expressed viral Ha-ras p21. The assay is performed essentially as described in DeClue, J. E. et al., Cancer Research 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 µCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 µl of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/ 0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 24
Cell-based in vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1×10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 25
Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of E. coli DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid, pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) J. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.

Sense strand N-terminal SEAP: 5'
GAGAGGGAATTCGGGCCCTTCCTGCAT GCTGCT-GCTGCTGCTGCTGGGC 3' (SEQ.ID.NO.:4)
Antisense strand N-terminal SEAP: 5'
GAGAGAGCTCGAGGTTAACCCGGGT GCGCG-GCGTCGGTGGT 3' (SEQ.ID.NO.:5)
Sense strand C-terminal SEAP: 5'
GAGAGAGTCTAGAGTTAACCCGTGGTCC CCGCGT-TGCTTCCT 3' (SEQ.ID.NO.:6)
Antisense strand C-terminal SEAP: 5'
GAAGAGGAAGCTTGGTACCGCCACTG GGCTGTAG-GTGGTGGCT 3' (SEQ.ID.NO.:7)

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 5) introduces an internal translation STOP codon within the SEAP gene along with the HpaI site. The C-terminal oligos (SEQ.ID.NO.: 6 and SEQ.ID.NO.: 7) were used to amplify a 412 bp C-terminal PCR product containing HpaI and HindIII restriction sites. The sense strand C-terminal oligo (SEQ.ID.NO.: 6) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electrophoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP-A

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand:
5' GGCAGAGCTCGTTTAGTGAACCGTCAG 3' (SEQ.ID.NO.: 8)
Antisense strand:
5' GAGAGATCTCAAGGACGGTGACTGCAG 3' (SEQ.ID.NO.: 9)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP-A (deposited in the ATCC under Budapest Treaty on Aug. 27, 1998, and designated ATCC), contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Alternative Construction of a Constitutively Expressing SEAP Plasmid pCMV-SEAP-B An expression plasmid constitutively expressing the SEAP protein can be created by placing the sequence encoding a truncated SEAP gene downstream of the cytomegalovirus (CMV) IE-1 promoter and upstream of the 3' unstranslated region of the bovine growth hormone gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter and bovine growth hormone poly-A sequence can be cut with EcoRI generating two fragments. The vector fragment can be isolated by agarose electrophoresis and religated. The resulting plasmid is named pCMV-AKI. The DNA sequence encoding the truncated SEAP gene can be inserted into the pCMV-AKI plasmid at a unique Bgl-II in the vector. The SEAP gene is cut out of plasmid pGEMzf(−)/SEAP (described above) using EcoRI and HindIII. The fragments are filled in with Klenow DNA polymerase and the 1970 base pair fragment is isolated from the vector fragment by agarose gel electrophoresis. The pCMV-AKI vector is prepared by digesting with Bgl-II and filling in the ends with Klenow DNA polymerase. The final construct is generated by blunt end ligating the SEAP fragment into the vector and transforming the ligation reaction into *E. coli* DH5αcells. Transformants can then be screened for the proper insert and mapped for restriction fragment orientation. Properly oriented recombinant constructs would be sequenced across the cloning junctions to verify the correct sequence. The resulting plasmid, named pCMV-SEAP-B contains a modified SEAP sequence downstream of the cytomegalovirus immediate early promoter, IE1, and upstream of a bovine growth hormone poly-A sequence. The plasmid would express SEAP in a constitutive nammer when transfected into mammalian cells.

Cloning of a Myristylated Viral-H-ras Expression Plasmid pSMS600

A DNA fragment containing viral-H-ras can be PCRed from plasmid "HB-11 (deposited in the ATCC under Budapest Treaty on Aug. 27, 1997, and designated ATCC 209,218) using the following oligos.
Sense strand:
5'TCTCCTCGAGGCCACCATGGGGAGTAG-CAAGAGCAAGCCTAA GGACCCCAGCCAGCGC-CGGATGACAGAATACAAGCTTGTGGTG G 3'. (SEQ.ID.NO.: 10)
Antisense:
5'CACATCTAGATCAGGACAGCACAGACTTGCAGC 3'. (SEQ.ID.NO.: 11)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid, pSMS600, in which the recombinant myr-viral-H-ras gene is constitutively transcribed from the CMV promoter of the pCI vector.

Cloning of a Viral-H-ras-CVLL Expression Plasmid pSMS601

A viral-H-ras clone with a C-terminal sequence encoding the amino acids CVLL can be cloned from the plasmid "HB-11" by PCR using the following oligos.
Sense strand:
5'TCTCCTCGAGGCCACCATGACAGAATACAAGCT-TGTGGTGG-3' (SEQ.ID.NO.: 12)
Antisense strand:
5' CACTCTAGACTGGTGTCAGAGCAGCACACACT-TGCAGC-3' (SEQ.ID.NO.: 13)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid, pSMS601, in which the mutated viral-H-ras-CVLL gene is constitutively transcribed from the CMV promoter of the pCI vector.

Cloning of Cellular-H-ras-Leu61 Expression Plasmid pSMS620

The human cellular-H-ras gene can be PCRed from a human cerebral cortex cDNA library (Clontech) using the following oligonucleotide primers.
Sense strand:
5'-GAGAGAATTCGCCACCATGACGGAATATAAGC-TGGTGG-3' (SEQ.ID.NO.: 14)
Antisense strand:
5'-GAGAGTCGACGCGTCAGGAGAGCACACACTT-GC-3' (SEQ.ID.NO.: 15)

The primers will amplify a c-H-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:
5'-CCGCCGGCCTGGAGGAGTACAG-3' (SEQ.ID.NO.: 16)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid, pSMS620, will constitutively transcribe c-H-ras-Leu61 from the CMV promoter of the pCI vector.

Cloning of a c-N-ras-Val-12 Expression Plasmid pSMS630

The human c-N-ras gene can be PCRed from a human cerebral cortex cDNA library (Clontech) using the following oligonucleotide primers.
Sense strand:
5'-GAGAGAATTCGCCACCATGACTGAGTACAAAC-TGGTGG-3' (SEQ.ID.NO.: 17)
Antisense strand:
5'-GAGAGTCGACTTGTTACATCACCACACATGGC-3' (SEQ.ID.NO.: 18)

The primers will amplify a c-N-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 19)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid, pSMS630, will constitutively transcribe c-N-ras-Val-12 from the CMV promoter of the pCI vector.

Cloning of a c-K4B-ras-Val-12 Expression Plasmid pSMS640

The human c-K4B-ras gene can be PCRed from a human cerebral cortex cDNA library (Clontech) using the following oligonucleotide primers.

Sense strand:
5'-GAGAGGTACCGCCACCATGACTGAATATAAACT-TGTGG-3' (SEQ.ID.NO.: 20)
Antisense strand:
5'-CTCTGTCGACGTATTTACATAATTACACACTTTG-TC-3' (SEQ.ID.NO.: 21)

The primers will amplify a c-K4B-Ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K4B-ras fragment can be ligated into a KpnI-Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 22)

After selection and sequencing for the correct nucleotide substitution, the mutated c-K4B-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K4B-ras-Val-12 from the CMV promoter of the pCI vector.

Cloning of c-K-ras4A-Val-12 Expression Plasmid pSMS650

The human c-K4A-ras gene can be PCRed from a human cerebral cortex cDNA library (Clontech) using the following oligonucleotide primers.

Sense strand:
5'-GAGAGGTACCGCCACCATGACTGAATATAAACT-TGTGG-3' (SEQ.ID.NO.: 23)
Antisense strand:
5'-CTCTGTCGACAGATTACATTATAATGCATTTTTT-AATTTTCACA C-3'(SEQ.ID.NO.: 24)

The primers will amplify a c-K4A-Ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K-ras4A fragment can be ligated into a KpnI-Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 25)

After selection and sequencing for the correct nucleotide substitution, the mutated c-K4A-ras-Val-12 can be excised from the pAlter-1 vector, using KpnI and Sal I, and be directly ligated into the vector pCI (Promega) which has been digested with KpnI and Sal I. The new recombinant plasmid, pSMS650, will constitutively transcribe c-K4A-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. (A ras expression plasmid is not included when the cell is transfected with the pCMV-SEAP plasmid.) For 10 cm plates 600 µl of $CaCl_2$-DNA solution is added dropwise while vortexing to 600 µl of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. No. 31053-028)+0.5% charcoal stripped calf serum+1×(Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1×(Pen/Strep, Glutamine and NEAA). Transfected cells are plated in a 96 well microtiter plate (100 µl/well) to which drug, diluted in media, has already been added in a volume of 100 µl. The final volume per well is 200 µl with each drug concentration repeated in triplicate over a range of half-log steps.

Incubation of cells and drugs is for 36 hrs at 37° C. under $CO_2$. At the end of the incubation period, cells are examined microscopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combined with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-$CaPO_4$ precipitate for 10 cm. plate of cell | |
|---|---|
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |
| 2M $CaCl_2$ | 74 µl |
| $dH_2O$ | 506 µl |

2×HBS Buffer
280 mM NaCl
10 mM KCl
1.5 mM $Na_2HPO_4$ $2H_2O$
12 mM dextrose
50 mM HEPES
Final pH=7.05

| Luminesence Buffer (26 ml) | |
| --- | --- |
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer
Add 0.05M $Na_2CO_3$ to 0.05M $NaHCO_3$ to obtain pH 9.5.
Make 1 mM in $MgCl_2$ Example 26

The processing assays employed are modifications of that described by DeClue et al [Cancer Research 51, 712–717, 1991].

K4B-Ras Processing Inhibition Assay

PSN-1 (human pancreatic carcinoma) or viral-K4B-ras-transformed Rat1 cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 $\mu$Ci/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 $\mu$g/ml AEBSF, 10 $\mu$g/ml aprotinin, 2 $\mu$g/ml leupeptin and 2 $\mu$g/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 $\mu$g of the pan Ras monoclonal antibody, Y13-259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 $\mu$g Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C. /5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to hDJ-2 (Neomarkers Cat. #MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of hDJ (the slower-migrating species) is calculated by densitometry. Dose-response curves and $EC_{50}$ values are generated using 4-parameter curve fits in SigmaPlot software.

Example 27

Rap1 Processing Inhibition Assay

Protocol A

Cells are labeled, incubated and lysed as described in Example 26.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 $\mu$g of the Rap1 antibody, Rap1/Krevl (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 $\mu$g Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C.

for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B

PSN-1 cells are passaged every 3–4 days in 10 cm plates, splitting near-confluent plates 1:20 and 1:40. The day before the assay is set up, $5 \times 10^6$ cells are plated on 15 cm plates to ensure the same stage of confluency in each assay. The media for these cells is RPM1 1640 (Gibco), with 15% fetal bovine serum and 1×Pen/Strep antibiotic mix.

The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in 1/2-log dilutions. The range of final concentrations to be assayed is generally 0.1–100 $\mu$M. Four concentrations per compound is typical. The compounds are diluted so that each concentration is 1000× of the final concentration (i.e., for a 10 $\mu$M data point, a 10 mM stock of the compound is needed).

2 $\mu$L of each 1000× compound stock is diluted into 1 ml media to produce a 2×stock of compound. A vehicle control solution (2 $\mu$L DMSO to 1 ml media), is utilized. 0.5 ml of the 2×stocks of compound are added to the cells.

After 24 hours, the media is aspirated from the assay plates. Each well is rinsed with 1 ml PBS, and the PBS is aspirated. 180 $\mu$L SDS-PAGE sample buffer (Novex) containing 5% 2-mercapto-ethanol is added to each well. The plates are heated to 100° C. for 5 minutes using a heat block containing an adapter for assay plates. The plates are placed on ice. After 10 minutes, 20 $\mu$L of an RNAse/DNase mix is added per well. This mix is 1 mg/ml DNaseI (Worthington Enzymes), 0.25 mg/ml Rnase A (Worthington Enzymes), 0.5 M Tris-HCl pH8.0 and 50 mM $MgCl_2$. The plate is left on ice for 10 minutes. Samples are then either loaded on the gel, or stored at –70° C. until use.

Each assay plate (usually 3 compounds, each in 4-point titrations, plus controls) requires one 15-well 14% Novex gel. 25 $\mu$l of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20 ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C

This protocol allows the determination of an $EC_{50}$ for inhibition of processing of Rap1a. The assay is run as described in Protocol B with the following modifications. 20 $\mu$l of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121;Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant® software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

Example 28

In vivo Tumor Growth Inhibition Assay (Nude Mouse)

In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995)) and N. E. Kohl et al. (Proc. Nat. Acad. Sci. U.S.A., 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound of the formula A:

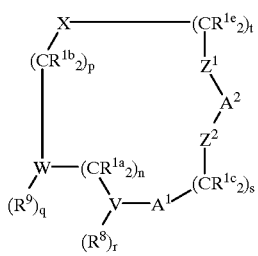

wherein:

$R^{1a}$, $R^{1b}$, $R^{1c}$ and $R^{1e}$ are independently selected from:

a) hydrogen, b) aryl, heterocycle, cycloalkyl, alkenyl, alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

or two $R^{1a}$s, two $R^{1b}$s, two $R^{1c}$s or two $R^{1e}$s, on the same carbon atom may be combined to form —$(CH_2)_v$—;

$R^4$ is selected from $C_{1-4}$ alkyl, $C_{3-6}$ cycloalkyl, heterocycle, aryl, unsubstituted or substituted with:

a) $C_{1-4}$ alkoxy, b) aryl or heterocycle, c) halogen, d) HO, e) 

f) —$SO_2R^{11}$, g) $N(R^{10})_2$, or h) $C_{1-4}$ perfluoroalkyl;

$R^6$ and $R^7$ are independently selected from:

1) hydrogen,

2) $R^{10}C(O)$—, or $R^{10}OC(O)$—, and

3) $C_1$–$C_6$ alkyl, $C_2$–$C_6$ alkenyl, $C_2$–$C_6$ alkynyl, $C_{3-6}$ cycloalkyl, heterocycle, aryl, aroyl, heteroaroyl, arylsulfonyl, heteroarylsulfonyl, $C_6$–$C_{10}$ multicyclic alkyl ring, unsubstituted or substituted with one or more substituents selected from:

a) $R^{10}O$—, b) aryl or heterocycle, c) halogen, d) $R^{10}C(O)NR^{10}$—, e) 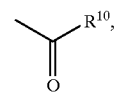

f) —$SO_2R^{11}$, g) $N(R^{10})_2$, h) $C_{3-6}$ cycloalkyl, i) $C_6$–$C_{10}$ multicyclic alkyl ring, j) $C_1$–$C_6$ perfluoroalkyl, k) $(R^{10})_2N$—$C(NR^{10})$—, l) $R^{10}OC(O)$—, m) $R^{11}OC(O)NR^{10}$—, n) CN, and o) $NO_2$; or $R^6$ and $R^7$ may be joined in a ring;

$R^8$ is independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{10}C(O)$—, $R^{10}OC(O)$—, $N_3$, —$N(R^{10})_2$, or $R^{10}OC(O)NH$—;

$R^9$ is selected from:

a) hydrogen, b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl, unsubstituted or substituted benzyl, unsubstituted or substituted aryl and unsubstituted or substituted heterocycle;

$R^{11}$ is independently selected from $C_1$–$C_6$ alkyl unsubstituted or substituted aryl and unsubstituted or substituted heterocycle;

$R^{12}$ is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond and O;

$A^2$ is selected from a bond, —$C(O)$—, —$C(O)NR^{10}$—, —$NR^{10}C(O)$—, O, —$N(R^{10})$—, —$S(O)_2N(R^{10})$—, —$N(R^{10})S(O)_2$—, $S(O)_m$ and —$C(R^{1d})_2$—;

W is imidazolyl;

V is phenyl;

X is independently selected from —$C(O)$—, —$C(O)NR^{10}$—, $NR^{10}C(O)$—, —$NR^{10}C(O)$—O—, —O—$C(O)$ NR$^{10}$—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$— and S(O)$_m$;

Z$^1$ is selected from unsubstituted or substituted phenyl and unsubstituted or substituted naphthyl, wherein the substituted phenyl or substituted naphthyl is substituted with one or more of:
1) C$_{1-8}$ alkyl, C$_{2-8}$ alkenyl or C$_{2-8}$ alkynyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$,
   g) —C(O)NR$^6$R$^7$,
   h) —Si(C$_{1-4}$ alkyl)$_3$, or
   i) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;

Z$^2$ is selected from a bond and unsubstituted or substituted phenyl wherein the substituted phenyl is substituted with one or more of:
1) C$_{1-8}$ alkyl, C$_{2-8}$ alkenyl or C$_{2-8}$ alkynyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$,
   g) —C(O)NR$^6$R$^7$,
   h) —Si(C$_{1-4}$ alkyl)$_3$, or
   i) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3;
t is 1, 2, 3 or 4; and
v is 2 to 6;

or a pharmaceutically acceptable salt or stereoisomer thereof.

2. The compound according to claim 1 of the formula A:

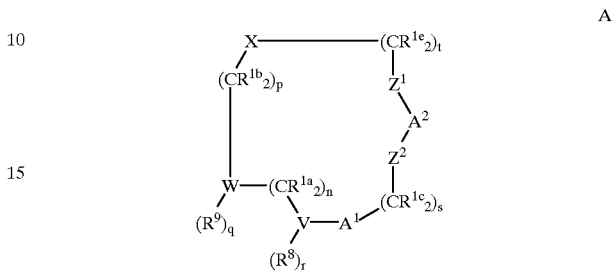

A wherein:
R$^{1a}$, R$^{1b}$, R$^{1c}$, R$^{1d}$ and R$^{1e}$ are independently selected from:
   a) hydrogen,
   b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$N—C(O)—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
   c) unsubstituted or substituted C$_1$–C$_6$ alkyl wherein the substitutent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

R$^4$ is selected from C$_{1-4}$ alkyl, C$_{3-6}$ cycloalkyl, heterocycle, aryl, unsubstituted or substituted with:
   a) C$_{1-4}$ alkoxy,
   b) aryl or heterocycle,
   c) halogen,
   d) HO,
   e) 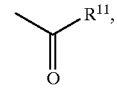
   f) —SO$_2$R$^{11}$, or
   g) N(R$^{10}$)$_2$;

R$^6$ and R$^7$ are independently selected from H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
   a) C$_{1-4}$ alkoxy,
   b) aryl or heterocycle,
   c) halogen,
   d) HO,
   e) 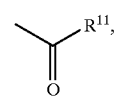
   f) —SO$_2$R$^{11}$, or
   g) N(R$^{10}$)$_2$; or $R^6$ and $R^7$ may be joined in a ring;

$R^8$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}{}_2N$—$C(NR^{10})$—, CN, $R^{10}C(O)$—, $R^{10}OC(O)$—, $N_3$, —$N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl, benzyl, unsubstituted or substituted aryl and unsubstituted or substituted heterocycle;

$R^{11}$ is independently selected from $C_1$–$C_6$ alkyl unsubstituted or substituted aryl and unsubstituted or substituted heterocycle;

$A^1$ is selected from a bond and O;

$A^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, S(O)$_m$ and —C(R$^{1d}$)$_2$—;

W is imidazolyl;

V is phenyl;

X is selected from —C(O)—, —C(O)NR$^{10}$—, —NR$^{10}$C(O)—, —NR$^{10}$C(O)—O—, —O—C(O)NR$^{10}$—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$— and S(O)$_m$;

$Z^1$ is selected from unsubstituted or substituted phenyl and unsubstituted or substituted naphthyl, wherein the substituted phenyl or substituted naphthyl is substituted with one or more of:
1) $C_{1-4}$ alkyl, unsubstituted or substituted with:
a) $C_{1-4}$ alkoxy,
b) NR$^6$R$^7$,
c) $C_{3-6}$ cycloalkyl,
d) aryl or heterocycle,
e) HO,
f) —S(O)$_m$R$^4$, or
g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) $C_3$–$C_6$ cycloalkyl;

$Z^2$ is selected from a bond and unsubstituted or substituted phenyl wherein the substituted phenyl is substituted with one or more of:
1) $C_{1-4}$ alkyl, unsubstituted or substituted with:
a) $C_{1-4}$ alkoxy,
b) NR$^6$R$^7$,
c) $C_{3-6}$ cycloalkyl,
d) aryl or heterocycle,
e) HO,
f) —S(O)$_m$R$^4$, or
g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
t is 1, 2, 3 or 4;
or a pharmaceutically acceptable salt or stereoisomer thereof.

3. The compound according to claim 1 of the formula B:

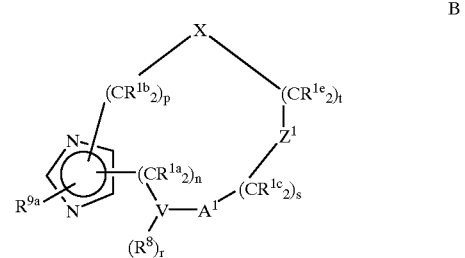

B wherein:

$R^{1a}$, $R^{1b}$ and $R^{1c}$ is independently selected from:
a) hydrogen,
b) aryl, heterocycle, cycloalkyl, $R^{10}O$—, —N(R$^{10}$)$_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —N(R$^{10}$)$_2$;

$R^{1e}$ is independently selected from:
a) hydrogen,
b) aryl, heterocycle, cycloalkyl, $R^{10}O$—, —N(R$^{10}$)$_2$ or $C_2$–$C_6$ alkenyl, and
c) $C_1$–$C_6$ alkyl unsubstituted or substituted by aryl, heterocycle, $R^{10}O$—, or —N(R$^{10}$)$_2$;

$R^4$ is selected from $C_{1-4}$ alkyl and $C_{3-6}$ cycloalkyl, unsubstituted or substituted with:

a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, heterocycle, aryl, aroyl, heteroaroyl, arylsulfonyl, heteroarylsulfonyl, unsubstituted or substituted with one or two:
a) $C_{1-4}$ alkoxy,
b) aryl or heterocycle,
c) halogen,
d) HO, e) 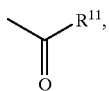

f) —$SO_2R^{11}$,
g) $N(R^{10})_2$,
h) $C_{3-6}$ cycloalkyl,
i) $C_6$–$C_{10}$ multicyclic alkyl ring; or $R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—C$(NR^{10})$—, $R^{10}C(O)$—, —$N(R^{10})_2$, or $R^{11}OC(O)NR^{10}$—, and
c) $C_1$–$C_6$ alkyl substituted by: unsubstituted or substituted aryl, $C_1$–$C_6$ perfluoroalkyl, $R^{10}O$—, $R^{10}C(O)NR^{10}$—, $(R^{10})_2N$—C$(NR^{10})$—, $R^{10}C(O)$—, —$N(R^{10})_2$, or $R^{11}OC(O)NR^{10}$—;

$R^{9a}$ is hydrogen or methyl;
$R^{10}$ is independently selected from hydrogen, $C_1$–$C_6$ alkyl, benzyl and unsubstituted or substituted aryl;
$R^{11}$ is independently selected from $C_1$–$C_6$ alkyl and unsubstituted or substituted aryl;
$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;
$A^1$ is O;
V is phenyl;
X is independently selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;
$Z^1$ is selected from unsubstituted or substituted phenyl and unsubstituted or substituted naphthyl, wherein the substituted phenyl or substituted naphthyl is substituted with one or more of:
1) $C_{1-8}$ alkyl, $C_{2-8}$ alkenyl or $C_{2-8}$ alkynyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) —$S(O)_mR^4$,
g) —$C(O)NR^6R^7$,
h) —$Si(C_{1-4}$ alkyl)3, or
i) $C_{1-4}$ perfluoroalkyl;
2) substituted or unsubstituted aryl or substituted or unsubstituted heterocycle, 3) halogen,
4) $OR^6$,
5) $NR^6R^7$,
6) CN,
7) $NO_2$,
8) $CF_3$,
9) —$S(O)_mR^4$,
10) —$OS(O)_2R^4$,
11) —$C(O)NR^6R^7$,
12) —$C(O)OR^6$, or
13) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;
or a pharmaceutically acceptable salt or stereoisomer thereof.

4. The compound according to claim 3 of the formula C-1:

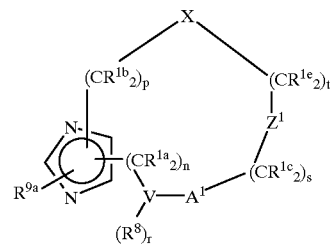

C-1 wherein:
$R^{1a}$, $R^{1b}$ and $R^{1c}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^{1e}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, $R^{10}O$—, or —$N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from:
a) hydrogen,
b) $C_1$–$C_6$ alkyl, $C_2$–$C_6$ alkenyl, $C_2$–$C_6$ alkynyl, $R^{10}C(O)$— or $R^{10}OC(O)$— and
c) $C_1$–$C_6$ alkyl substituted by $C_1$–$C_6$ perfluoroalkyl, $R^{10}O$—, $R^{10}C(O)NR^{10}$—, $(R^{10})_2N$—C$(NR^{10})$—, $R^{10}C(O)$—, $R^{10}OC(O)$—, —$N(R^{10})_2$, or $R^{11}OC(O)NR^{10}$—;

$R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O-$, $R^{10}C(O)NR^{10}-$, CN, NO$_2$, $(R^{10})_2N-C(NR^{10})-$, $R^{10}C(O)-$, $-N(R^{10})_2$, or $R^{11}OC(O)NR^{10}-$, and c) $C_1-C_6$ alkyl substituted by unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;

$R^{10}$ is independently selected from hydrogen, $C_1-C_6$ alkyl, benzyl and unsubstituted or substituted aryl;

$R^{11}$ is independently selected from $C_1-C_6$ alkyl and unsubstituted or substituted aryl;

$R^{12}$ is independently selected from hydrogen, $C_1-C_6$ alkyl, unsubstituted or substituted benzyl, unsubstituted or substituted aryl, unsubstituted or substituted heterocycle, and $C_1-C_6$ alkyl substituted with unsubstituted or substituted aryl or unsubstituted or substituted heterocycle;

$A^1$ is O;

V is phenyl;

X is independently selected from $-C(O)-$, $-C(O)NR^{10}-$, $-NR^{10}C(O)-$, $-NR^{10}C(O)NR^{10}-$, $-C(O)NR^{10}C(O)-$, O, $-N(R^{10})-$, $-S(O)_2N(R^{10})-$, $-N(R^{10})S(O)_2-$, and $S(O)_m$;

$Z^1$ is selected from unsubstituted or substituted phenyl and unsubstituted or substituted naphthyl, wherein the substituted phenyl or substituted naphthyl is substituted with one or more of:

1) $C_{1-4}$ alkyl, unsubstituted or substituted with:
   a) $C_{1-4}$ alkoxy,
   b) NR$^6$R$^7$,
   c) $C_{3-6}$ cycloalkyl,
   d) aryl or heterocycle,
   e) HO,
   f) $-S(O)_mR^4$, or
   g) $-C(O)NR^6R^7$,
2) aryl or heterocycle,
3) halogen,
4) OR$^6$,
5) NR$^6$R$^7$,
6) CN,
7) NO$_2$,
8) CF$_3$,
9) $-S(O)_mR^4$,
10) $-C(O)NR^6R^7$, or
11) $C_3-C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

5. The compound according to claim 4 of the formula D:

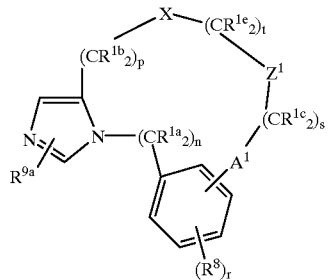

D wherein:

$R^{1a}$, $R^{1b}$ and $R^{1c}$ are independently selected from:
a) hydrogen,
b) aryl, heterocycle, cycloalkyl, $R^{10}O-$, $-N(R^{10})_2$ or $C_2-C_6$ alkenyl, and
c) $C_1-C_6$ alkyl unsubstituted or substituted by aryl, heterocycle, cycloalkyl, alkenyl, $R^{10}O-$, or $-NR^{10})_2$;

$R^{1e}$ is independently selected from:
a) hydrogen,
b) aryl, heterocycle, cycloalkyl, $R^{10}O-$, $-N(R^{10})_2$ or $C_2-C_6$ alkenyl, and
c) $C_1-C_6$ alkyl unsubstituted or substituted by aryl, heterocycle, $R^{10}O-$, or $-N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6-C_{10}$ multicyclic alkyl ring, aryl, aroyl, arylsulfonyl, unsubstituted or substituted with one or two:
a) $C_{1-4}$ alkoxy,
b) aryl,
c) halogen,
d) HO, e) 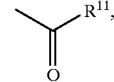

f) $-SO_2R^{11}$,
g) $N(R^{10})_2$,
h) $C_{3-6}$ cycloalkyl,
i) $C_6-C_{10}$ multicyclic alkyl ring; or $R^8$ is independently selected from:
a) hydrogen,
b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{12}O-$, $R^{10}C(O)NR^{10}-$, CN, NO$_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;

$R^{10}$ and $R^{12}$ are independently selected from hydrogen, $C_1-C_6$ alkyl, unsubstituted or substituted benzyl and unsubstituted or substituted aryl;

$R^{11}$ is independently selected from $C_1$–$C_6$ alkyl and unsubstituted or substituted aryl;

$A^1$ is O;

X is independently selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

$Z^1$ is selected from unsubstituted or substituted phenyl and unsubstituted or substituted naphthyl, wherein the substituted phenyl or substituted naphthyl is substituted with one or more of:

1) $C_{1-8}$ alkyl, $C_{2-8}$ alkenyl or $C_{2-8}$ alkynyl, unsubstituted or substituted with:
   a) $C_{1-4}$ alkoxy,
   b) NR$^6$R$^7$,
   c) $C_{3-6}$ cycloalkyl,
   d) aryl or heterocycle,
   e) HO,
   f) —S(O)$_m$R$^4$,
   g) —C(O)NR$^6$R$^7$,
   h) —Si(C$_{1-4}$ alkyl)$_3$, or
   i) $C_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

6. The compound according to claim 4 of the formula E:

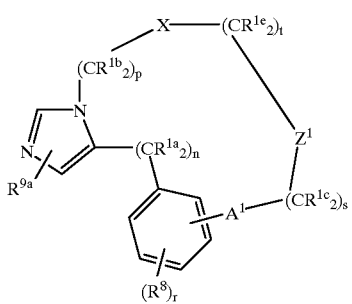

E wherein:

$R^{1a}$, $R^{1b}$ and $R^{1c}$ are independently selected from:
a) hydrogen,
b) aryl, heterocycle, cycloalkyl, R$^{10}$O—, —N(R$^{10}$)$_2$ or $C_2$–$C_6$ alkenyl, and
c) $C_1$–$C_6$ alkyl unsubstituted or substituted by aryl, heterocycle, cycloalkyl, alkenyl, R$^{10}$O—, or —N(R$^{10}$)$_2$;

$R^{1e}$ is independently selected from:
a) hydrogen,
b) aryl, heterocycle, cycloalkyl, R$^{10}$O—, —N(R$^{10}$)$_2$ or $C_2$–$C_6$ alkenyl, and
c) $C_1$–$C_6$ alkyl unsubstituted or substituted by aryl, heterocycle, R$^{10}$O—, or —N(R$^{10}$)$_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, aryl, aroyl, arylsulfonyl, unsubstituted or substituted with one or two:
a) $C_{1-4}$ alkoxy,
b) aryl,
c) halogen,
d) HO, e) 

f) —SO$_2$R$^{11}$,
g) N(R$^{10}$)$_2$,
h) $C_{3-6}$ cycloalkyl,
i) $C_6$–$C_{10}$ multicyclic alkyl ring; or $R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl substituted by unsubstituted or substituted aryl, $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

$R^{9a}$ is hydrogen or methyl;

$R^{10}$ and $R^{12}$ are independently selected from hydrogen, $C_1$–$C_6$ alkyl, unsubstituted or substituted benzyl and unsubstituted or substituted aryl;

$R^{11}$ is independently selected from $C_1$–$C_6$ alkyl and unsubstituted or substituted aryl;

$A^1$ is O;

X is independently selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

$Z^1$ is selected from unsubstituted or substituted phenyl and unsubstituted or substituted naphthyl, wherein the substituted phenyl or substituted naphthyl is substituted with one or more of:

1) $C_{1-8}$ alkyl, $C_{2-8}$ alkenyl or $C_{2-8}$ alkynyl, unsubstituted or substituted with:
   a) $C_{1-4}$ alkoxy,
   b) NR$^6$R$^7$,
   c) $C_{3-6}$ cycloalkyl,
   d) aryl or heterocycle,
   e) HO, f) —S(O)$_m$R$^4$,
g) —C(O)NR$^6$R$^7$,
h) —Si(C$_{1-4}$ alkyl)$_3$, or
i) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;

m is 0, 1 or 2;
n is 0, 1, 2, 3 or 4;
p is 2, 3 or 4;
r is 0 to 5;
s is independently 0, 1, 2 or 3; and
t is 1, 2, 3 or 4;
or a pharmaceutically acceptable salt or stereoisomer thereof.

7. A compound which is selected from:

18,19-dihydro-19-oxo-5H,17H-6,10:12,16-dimetheno-1H-imidazo[4,3-c][1,11,4]dioxaazacyclononadecine-9-carbonitrile (1),
17,18-dihydro-18-oxo-5H-6,10:12,16-dimetheno-12H,20H-imidazo[4,3-c][1,11,4]dioxaazacyclooctadecine-9-carbonitrile (2),
(±)-17,18,19,20-tetrahydro-19-phenyl-5H-6,10:12,16-dimetheno-21H-imidazo[3,4-h][1,8,11]oxadiazacyclononadecine-9-carbonitrile (3),
21,22-dihydro-5H-6,10:12,16-dimetheno-23H-benzo[g]imidazo[4,3-1][1,8,11]oxadiazacyclononadecine-9-carbonitrile (4),
22,23-dihydro-23-oxo-5H,21H-6,10:12,16-dimetheno-24H-benzo[g]imidazo[4,3-m][1,8,12]oxadiazaeicosine-9-carbonitrile (5),
22,23-dihydro-5H,21H-6,10:12,16-dimetheno-24H-benzo[g]imidazo[4,3-m][1,8,11]oxadiazaeicosine-9-carbonitrile (6),
22,23-dihydro-5H,21H-6,10:12,16-dimetheno-23-methyl-24H-benzo[g]imidazo[4,3-m][1,8,11]oxadiazaeicosine-9-carbonitrile (7),
(±)-5-hydroxy-5-methyl-24-oxo-21,22,23,24-tetrahydro-5H-6,10:12,16-dimetheno-25H-benzo[o]imidazo[4,3-h][1,9,12]oxadiaza-cycloheneicosine-9-carbonitrile (8),
17-Oxo-17,18,23,24-tetrahydro-5H-6,10:12,16-dimetheno-25H,26H-benzo[n]imidazo[3,4-h][1,8,12,16]oxatriaza-cyclodocosine-9-carbonitrile (9)
3-Methyl-17-oxo-17,18,23,24-tetrahydro-5H-6,10:12,16-dimetheno-25H,26H-benzo[n]imidazo[3,4-h][1,8,12,16]-oxatriazacyclodocosine-9-carbonitrile (10)
24-tert-Butoxycarbonyl-3-methyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (11)
24-tert-Butoxycarbonyl-18-ethyl-3-methyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (12)
18-Ethyl-3-methyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (13)
24-Acetyl-3-methyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (14)
3-methyl-24-methylsulfonylethyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (15)
3,24-Dimethyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (16)
17,18-Dihydro-15-iodo-3-methyl-17-oxo-5H-6,10:12,16-dimetheno-19H,20H-imidazo[3,4-h][1,8,12]oxadiazacyclooctadecine-9-carbonitrile (17)
17,18-Dihydro-3-methyl-17-oxo-15-phenyl-5H-6,10:12,16-dimetheno-19H,20H-imidazo[3,4-h][1,8,12]oxadiaza-cyclooctadecine-9-carbonitrile (18)
trans-15-[2-(3-Chlorophenyl)ethenyl]-17,18-dihydro-3-methyl-17-oxo-5H-6,10:12,16-dimetheno-19H,20H-imidazo[3,4-h][1,8,12]oxadiazacyclooctadecine-9-carbonitrile (19)
18-Benzyl-17,18-dihydro-15-iodo-3-methyl-17-oxo-5H-6,10:12,16-dimetheno-19H,20H-imidazo[3,4-h][1,8,12]oxadiaza-cyclooctadecine-9-carbonitrile (20)

or a pharmaceutically acceptable salt or stereoisomer thereof.

8. The compound according to claim 7 which is:

22,23-dihydro-23-oxo-5H,21H-6,10:12,16-dimetheno-24H-benzo[g]imidazo[4,3-m][1,8,12]oxadiazaeicosine-9-carbonitrile (5),

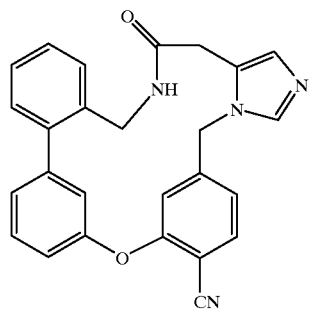

or a pharmaceutically acceptable salt or stereoisomer thereof.

9. The compound according to claim 7 which is:

22,23-dihydro-5H,21H-6,10:12,16-dimetheno-24H-benzo[g]imidazo[4,3-m][1,8,11]oxadiazaeicosine-9-carbonitrile (6),

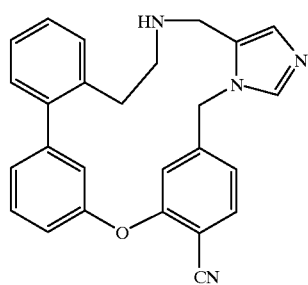

or a pharmaceutically acceptable salt or stereoisomer thereof.

10. The compound according to claim 7 which is:
17-Oxo-17,18,23,24-tetrahydro-5H-6,10:12,16-dimetheno-25H,26H-benzo[n]imidazo[3,4-h][1,8,12,16]oxatriaza-cyclodocosine-9-carbonitrile (9)

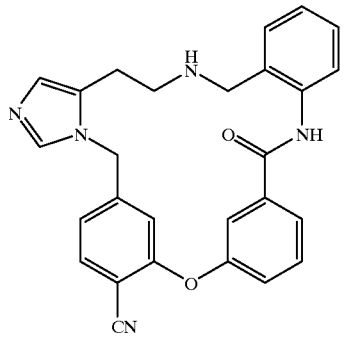

or a pharmaceutically acceptable salt or stereoisomer thereof.

11. The compound according to claim 7 which is:
18-Ethyl-3-methyl-17-oxo-17,18,23,24-tetrahydro-5H-6,10:12,16-dimetheno-25H,26H-benzo[n]imidazo[3,4-h][1,8,12,16]oxatriazacyclodocosine-9-carbonitrile (13)

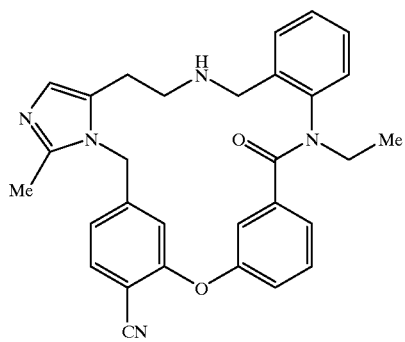

or a pharmaceutically acceptable salt or stereoisomer thereof.

12. The compound according to claim 7 which is:
17,18-Dihydro-15-iodo-3-methyl-17-oxo-5H-6,10:12,16-dimetheno-19H,20H-imidazo[3,4-h][1,8,12]oxadiazacyclooctadecine-9-carbonitrile (17)

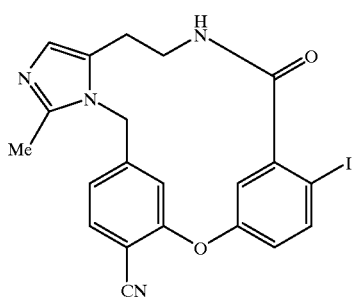

or a pharmaceutically acceptable salt or stereoisomer thereof.

13. A pharmaceutical composition comprising a pharmaceutical carrier, and dispersed therein, a therapeutically effective amount of a compound of claim 1.

14. A pharmaceutical composition comprising a pharmaceutical carrier, and dispersed therein, a therapeutically effective amount of a compound of claim 1.

15. A pharmaceutical composition comprising a pharmaceutical carrier, and dispersed therein, a therapeutically effective amount of a compound of claim 5.

16. A pharmaceutical composition comprising a pharmaceutical carrier, and dispersed therein, a therapeutically effective amount of a compound of claim 7.

17. A method for treating neurofibromin benign proliferative disorder which comprises administering to a mammal in need thereof a therapeutically effective amount of a composition of claim 13.

18. A method for treating blindness related to retinal vascularization which comprises administering to a mammal in need thereof a therapeutically effective amount of a composition of claim 13.

19. A method for treating infections from hepatitis delta and related viruses which comprises administering to a mammal in need thereof a therapeutically effective amount of a composition of claim 13.

20. A method for preventing restenosis which develops as a result of percutaneous transluminal coronary angioplasty which comprises administering to a mammal in need thereof a therapeutically effective amount of a composition of claim 13.

21. A method for treating polycystic kidney disease which comprises administering to a mammal in need thereof a therapeutically effective amount of a composition of claim 13.

22. A method of conferring radiation sensitivity on a tumor cell using a therapeutically effective amount of a composition of claim 13 in combination with radiation therapy.

23. A pharmaceutical composition made by combining the compound of claim 1 and a pharmaceutically acceptable carrier.

24. A process for making a pharmaceutical composition comprising combining a compound of claim 1 and a pharmaceutically acceptable carrier.

25. A method for treating cancer related to a mutation, which is selected from a mutation in the ras gene and a mutation in a protein that can regulate Ras activity, which comprises administering to a mammal in need thereof a therapeutically effective amount of a composition of claim 13.

26. A method for treating cancer related to a mutation, which is selected from a mutation in the ras gene and a mutation in a protein that can regulate Ras activity,b which comprises administering to a mammal in need thereof a therapeutically effective amount of a composition of claim 16.

* * * * *

UNITED STATES PATENT AND TRADEMARK OFFICE
CERTIFICATE OF CORRECTION

PATENT NO. : 6,358,985 B1
DATED : March 19, 2002
INVENTOR(S) : Neville J. Anthony, Ian M. Bell, Douglass C. Beshore, Terrence M. Ciccarone, S. Jane deSolms, Christopher J, Dinsmore and Gerald E. Stokker It is certified that error appears in the above-identified patent and that said Letters Patent is hereby corrected as shown below:

<u>Column 114,</u>
Line 59, should read as follows:
-- mutation in protein that can regulate Ras activity, which --.

Signed and Sealed this

Ninth Day of July, 2002

*Attest:*

*Attesting Officer*

JAMES E. ROGAN
*Director of the United States Patent and Trademark Office*